United States Patent [19]

Weidmann et al.

[11] Patent Number: 5,658,933
[45] Date of Patent: Aug. 19, 1997

[54] SUBSTITUTED HETEROCYCLIC CARBOXAMIDE ESTERS, THEIR PREPARATION AND THEIR USE AS PHARMACEUTICALS

[75] Inventors: Klaus Weidmann, Kronberg; Karl-Heinz Baringhaus, Wölfersheim; Georg Tschank, Klein-Winternheim; Martin Bickel, Bad Homburg, all of Germany

[73] Assignee: Hoechst Aktiengesellschaft, Frankfurt am Main, Germany

[21] Appl. No.: 332,824

[22] Filed: Oct. 31, 1994

[30] Foreign Application Priority Data

Nov. 2, 1993 [DE] Germany .................. 43 37 270.8
Sep. 26, 1994 [DE] Germany .................. 44 34 288.8

[51] Int. Cl.[6] .................. C07D 213/81; A61K 31/455
[52] U.S. Cl. .................. 514/350; 544/223; 544/235; 544/239; 546/141; 546/147; 546/143; 546/156; 546/161; 546/169; 546/298; 546/310; 546/323; 514/248; 514/252; 514/307; 514/309; 514/310; 514/311; 514/312; 514/313; 514/352; 514/354
[58] Field of Search .................. 544/223, 235, 544/239; 546/141, 147, 143, 156, 161, 169, 298, 310, 323; 514/248, 252, 307, 309, 310, 311, 312, 313, 350, 352, 354

[56] References Cited

U.S. PATENT DOCUMENTS

| | | | |
|---|---|---|---|
| 5,192,773 | 3/1993 | Armistead et al. | 514/315 |
| 5,204,338 | 4/1993 | Baader et al. | 514/183 |

FOREIGN PATENT DOCUMENTS

| | | | |
|---|---|---|---|
| 0 541 042 | 5/1993 | European Pat. Off. | 514/315 |
| 0 562 512 | 9/1993 | European Pat. Off. | 514/315 |

OTHER PUBLICATIONS

John T. Sheehan, 3–Hydroxypicolinic Acid and Some of Its Derivatives. Journal of Organic Chemistry, vol. 31, Feb. 1966, pp. 636–638.

Horst Kessler et al., 'Synthese des Benzylethers von Virginiamycin S1' Liebigs Annalen Der Chimie., Nr. 1, 1986, pp. 1–20.

*Primary Examiner*—Zinna Northington Davis
*Attorney, Agent, or Firm*—Finnegan, Henderson, Farabow, Garrett & Dunner, L.L.P.

[57] ABSTRACT

The invention relates to compounds of the formula I,

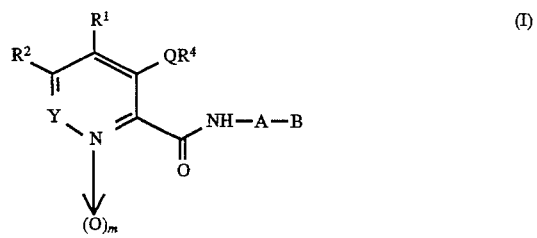

to a process for their preparation and to their use as pharmaceuticals. The compounds are employed, in particular, as ester prodrugs of prolyl hydroxylase inhibitors for inhibiting collagen biosynthesis and as fibrosuppressive agents.

16 Claims, No Drawings

SUBSTITUTED HETEROCYCLIC CARBOXAMIDE ESTERS, THEIR PREPARATION AND THEIR USE AS PHARMACEUTICALS

The invention relates to substituted heterocyclic carboxamide esters, to their preparation and to their use for inhibiting collagen biosynthesis, and to their use as pharmaceuticals for treating fibrotic diseases.

Compounds which inhibit the enzymes proline hydroxylase and lysine hydroxylase bring about a very selective inhibition of collagen biosynthesis by their influence on the collagen-specific hydroxylation reactions. In the course of these reactions, protein-bound proline or lysine is hydroxylated by the enzymes proline hydroxylase, or lysine hydroxylase, respectively. If this reaction is prevented by inhibitors, there then arises a non-functional, subhydroxylated collagen molecule which can only be secreted by the cells into the extracellular space in small quantities. Furthermore, the subhydroxylated collagen cannot be incorporated into the collagen matrix and is very readily degraded proteolytically. These effects result in a diminution of the overall quantity of collagen which is deposited extracellularly.

Inhibitors of prolyl hydroxylase are therefore suitable substances for use in the therapy of diseases in which the deposition of collagens makes a substantial contribution to the clinical picture. These diseases include, inter alia, fibroses of the lung, liver and skin (scleroderma and cicatrizations following burns, injuries and surgical intervention) and also atherosclerosis.

It is known that the enzyme proline hydroxylase is efficiently inhibited by pyridine-2,4-dicarboxylic acid and pyridine-2,5-dicarboxylic acid (K. Majamaa et al., Eur. J. Biochem. 138 (1984) 230–245). However, these compounds are only active as inhibitors in cell culture at very high concentrations (Tschank, G. et al., Biochem. J. 238 (1987) 625–633).

Prodrugs of pyridine-2,4(5)-dicarboxylates are also known. These are described in the relatively old German Applications P 42 33 124.2, P 42 38 506.7 and P 42 09 424.0.

N-Oxalylglycines which are inhibitors of prolyl-4-hydroxylase are disclosed in J. Med. Chem. 1992, 35, 2652–2658 (Cunliffe et al.) and EP-A-0 457 163.

Hydroxyisoquinolinecarboxylic acid glycyl amides and hydroxycinnolinecarboxylic acid glycyl amides are disclosed in Biochem. Soc. Trans. 1991, 19, 812–815 (Franklin et al.). 3-Benzyloxypyridine-2-carboxylic acid (L-threonyl methyl ester) amide, 3-benzyloxypyridine-2-carboxylic acid (L-threonyl(Fmoc-Phg) tert-butyl ester) amide, 3-benzyloxypyridine-2-carboxylic acid (L-threonyl tert-butyl ester) amide and 3-benzyloxypyridine-2-carboxylic acid (D-allothreonyl methyl ester) amide are disclosed in Liebigs Ann. Chem., 1986, 1–20, Kessler et al.

In addition, 3-benzyloxypyridine-2-carboxylic acid (glycyl ethyl ester) amide is described in J. Org. Chem. 31, 636–638 (1966).

It has now been found, surprisingly, that heterocyclic carboxamides of the formula I having an ether substituent, a thioether substituent or an amino substituent in the ortho position to the amide function have a strong inhibitory action on collagen biosynthesis in vivo.

The compounds are ester prodrugs of the corresponding carboxylic acids of the formula I in which B is a carboxyl group.

The compounds of the formula I are cleaved in the living organism (in vivo) and in cell cultures (in vitro) to form compounds of the formula I in which B is a carboxyl group or its salts.

Once the compounds of the formula I have been administered, they bring about the inhibition, which is to be observed in vivo and in vitro, of collagen biosynthesis by forming compounds of the formula I in which B is a carboxyl group or its salts. These compounds inhibit prolyl-4-hydroxylase and therefore lead to an inhibition of collagen biosynthesis.

The compounds according to the invention conform to the formula I

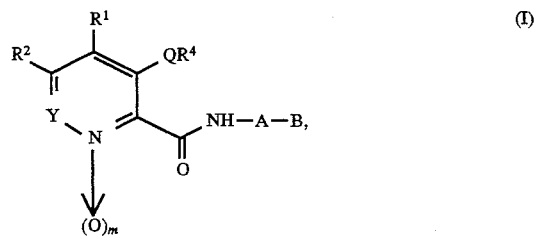

in which

Q is O, S, NR' or a bond,

X is O or S,

Y is C—$R^3$ or, if $R^1$ and $R^2$ form a cycle,

Y is N or $CR^3$, m is 0 or 1,

A is ($C_1$–$C_4$)-alkylene, which is optionally substituted by one or two substituents from the group halogen, cyano, nitro, trifluoromethyl, ($C_1$–$C_6$)-alkyl, ($C_1$–$C_6$)-hydroxyalkyl, ($C_1$–$C_6$)-alkoxy, —O—$[CH_2]_x$—$C_fH_{(2f+1-g)}Hal_g$, preferably ($C_1$–$C_6$)-fluoroalkoxy, ($C_1$–$C_8$)-fluoroalkenyloxy, ($C_1$–$C_8$)-fluoroalkynyloxy, —$OCF_2Cl$ or —O—$CF_2$—$CHFCl$, ($C_1$–$C_6$)-alkylmercapto, ($C_1$–$C_6$)-alkylsulfinyl, ($C_1$–$C_6$)-alkylsulfonyl, ($C_1$–$C_6$)-alkylcarbonyl, ($C_1$–$C_6$)-alkoxycarbonyl, carbamoyl, N-($C_1$–$C_4$)-alkylcarbamoyl, N,N-di-($C_1$–$C_4$)-alkylcarbamoyl, ($C_1$–$C_6$)-alkylcarbonyloxy, ($C_3$–$C_8$)-cycloalkyl, phenyl, benzyl, phenoxy, benzyloxy, anilino, N-methylanilino, phenylmercapto, phenylsulfonyl, phenylsulfinyl, sulfamoyl, N-($C_1$–$C_4$)-alkylsulfamoyl or N,N-di-($C_1$–$C_4$)-alkylsulfamoyl, or by a substituted ($C_6$–$C_{12}$)-aryloxy, ($C_7$–$C_{11}$)-aralkyloxy, ($C_6$–$C_{12}$)-aryl or ($C_7$–$C_{11}$)-aralkyl radical which carries in the aryl moiety 1, 2, 3, 4 or 5 identical or different substituents from the group halogen, cyano, nitro, trifluoromethyl, ($C_1$–$C_6$)-alkyl, ($C_1$–$C_6$)-alkoxy, —O—$[CH_2]_x$—$C_fH_{(2f+1-g)}Hal_g$, —$OCF_2Cl$, —O—$CF_2$—$CHFCl$, ($C_1$–$C_6$)-alkylmercapto, ($C_1$–$C_6$)-alkylsulfinyl, ($C_1$–$C_6$)-alkylsulfonyl, ($C_1$–$C_6$)-alkylcarbonyl, ($C_1$–$C_6$)-alkoxycarbonyl, carbamoyl, N-($C_1$–$C_4$)-alkylcarbamoyl, N,N-di-($C_1$–$C_4$)-alkylcarbamoyl, ($C_1$–$C_6$)-alkylcarbonyloxy, ($C_3$–$C_8$)-cycloalkyl, sulfamoyl, N-($C_1$–$C_4$)-alkylsulfamoyl or N,N-di-($C_1$–$C_4$)-alkylsulfamoyl, or by the substituents $R^5$ of the α-C atom of an α-amino acid, it being possible to use the natural L-amino acids and their D-isomers;

B is —$CO_2G$, where G is the radical of an alcohol GOH, $R^1$, $R^2$ and $R^3$ are identical or different and are hydrogen, hydroxyl, halogen, cyano, trifluoromethyl, nitro, carboxyl, ($C_1$–$C_{20}$)-alkyl, ($C_3$–$C_8$)-cycloalkyl, ($C_3$–$C_8$)-cycloalkyl-($C_1$–$C_{12}$)-alkyl, ($C_3$–$C_8$)-cycloalkoxy, ($C_3$–$C_8$)-cycloalkyl-($C_1$–$C_{12}$)-alkoxy, ($C_3$–$C_8$)-cycloalkyloxy-($C_1$–$C_{12}$)-alkyl, ($C_3$–$C_8$)-cycloalkyloxy-($C_1$–$C_{12}$)-alkoxy, ($C_3$–$C_8$)-cycloalkyl-($C_1$–$C_8$)-alkyl-($C_1$–$C_6$)-alkoxy, ($C_3$–$C_8$)-cycloalkyl- ($C_1$–$C_8$)-alkoxy-($C_1$–$C_6$)-alkyl, ($C_3$–$C_8$)-cycloalkyloxy-($C_1$–$C_8$)-alkoxy-($C_1$–$C_6$)-alkyl, ($C_3$–$C_8$)-cycloalkoxy-($C_1$–$C_8$)-alkoxy-($C_1$–$C_8$)-alkoxy, ($C_6$–$C_{12}$)-aryl, ($C_7$–$C_{16}$)-aralkyl, ($C_7$–$C_{16}$)-aralkenyl, ($C_7$–$C_{16}$)-aralkynyl, ($C_2$–$C_{20}$)-alkenyl, ($C_2$–$C_{20}$)-alkynyl, ($C_1$–$C_{20}$)-alkoxy, ($C_2$–$C_{20}$)-alkenyloxy, ($C_2$–$C_{20}$)-alkynyloxy, retinyloxy, ($C_1$–$C_{12}$)-alkoxy-($C_1$–$C_{12}$)-alkyl, ($C_1$–$C_{12}$)-alkoxy-($C_1$–$C_{12}$)-alkoxy, ($C_1$–$C_{12}$)-alkoxy-($C_1$–$C_8$)-alkoxy-($C_1$–$C_8$)-alkyl, ($C_6$–$C_{12}$)-aryloxy, ($C_7$–$C_{16}$)-aralkyloxy, ($C_6$–$C_{12}$)-aryloxy-($C_1$–$C_6$)-alkoxy, ($C_7$–$C_{16}$)-aralkoxy-($C_1$–$C_6$)-alkoxy, ($C_1$–$C_{16}$)-hydroxyalkyl, ($C_6$–$C_{16}$)-aryloxy-($C_1$–$C_8$)-alkyl, ($C_7$–$C_{16}$)-aralkoxy-($C_1$–$C_8$)-alkyl, ($C_6$–$C_{12}$)-aryloxy-($C_1$–$C_8$)-alkoxy-($C_1$–$C_6$)-alkyl, ($C_7$–$C_{12}$)-aralkyloxy-($C_1$–$C_8$)-alkoxy-($C_1$–$C_6$)-alkyl, ($C_2$–$C_{20}$)-alkenyloxy-($C_1$–$C_6$)-alkyl, ($C_2$–$C_{20}$)-alkynyloxy-($C_1$–$C_6$)-alkyl, retinyloxy-($C_1$–$C_6$)-alkyl, —O—[CH2,]$_x$—$C_fH_{(2f+1-g)}F_g$, —OCF$_2$Cl, —OCF$_2$—CHFCl, ($C_1$–$C_{20}$)-alkylcarbonyl, ($C_3$–$C_8$)-cycloalkylcarbonyl, ($C_6$–$C_{12}$)-arylcarbonyl, ($C_7$–$C_{16}$)-aralkylcarbonyl, cinnamoyl, ($C_2$–$C_{20}$)-alkenylcarbonyl, ($C_2$–$C_{20}$)-alkynylcarbonyl, ($C_1$–$C_{20}$)-alkoxycarbonyl, ($C_1$–$C_{12}$)-alkoxy-($C_1$–$C_{12}$)-alkoxycarbonyl, ($C_6$–$C_{12}$)-aryloxycarbonyl, ($C_7$–$C_{16}$)-aralkoxycarbonyl, ($C_3$–$C_8$)-cycloalkoxycarbonyl, ($C_2$–$C_{20}$)-alkenyloxycarbonyl, retinyloxycarbonyl, ($C_2$–$C_{20}$)-alkynyloxycarbonyl, ($C_6$–$C_{12}$)-aryloxy-($C_1$–$C_6$)-alkoxycarbonyl, ($C_7$–$C_{16}$)-aralkoxy-($C_1$–$C_6$)-alkoxycarbonyl, ($C_3$–$C_8$)-cycloalkyl-($C_1$–$C_6$)-alkoxycarbonyl, ($C_3$–$C_8$)-cycloalkoxy-($C_1$–$C_6$)-alkoxycarbonyl, ($C_1$–$C_{12}$)-alkylcarbonyloxy, ($C_3$–$C_8$)-cycloalkylcarbonyloxy, ($C_6$–$C_{12}$)-arylcarbonyloxy, ($C_7$–$C_{16}$)-aralkylcarbonyloxy, cinnamoyloxy, ($C_2$–$C_{12}$)-alkenylcarbonyloxy, ($C_2$–$C_{12}$)-alkynylcarbonyloxy, ($C_1$–$C_{12}$)-alkoxycarbonyloxy, ($C_1$–$C_{12}$)-alkoxy-($C_1$–$C_{12}$)-alkoxycarbonyloxy, ($C_6$–$C_{12}$)-aryloxycarbonyloxy, ($C_7$–$C_{16}$)-aralkyloxycarbonyloxy, ($C_3$–$C_8$)-cycloalkoxycarbonyloxy, ($C_2$–$C_{12}$)-alkenyloxycarbonyloxy, ($C_2$–$C_{12}$)-alkynyloxycarbonyloxy, carbamoyl, N-($C_1$–$C_{12}$)-alkylcarbamoyl, N,N-di-($C_1$–$C_{12}$)-alkylcarbamoyl, N-($C_3$–$C_8$)-cycloalkylcarbamoyl, N,N-dicyclo-($C_3$–$C_8$)-alkylcarbamoyl, N-($C_1$–$C_{10}$)-alkyl-N-($C_3$–$C_8$)-cycloalkylcarbamoyl, N-(($C_3$–$C_8$)-cycloalkyl-($C_1$–$C_6$)-alkyl)carbamoyl, N-($C_1$–$C_6$)-alkyl-N-(($C_3$–$C_8$)-cycloalkyl-($C_1$–$C_6$)-alkyl)carbamoyl, N-(+)-dehydroabietylcarbamoyl, N-($C_1$–$C_6$)-alkyl-N-(+)-dehydroabietylcarbamoyl, N-($C_6$–$C_{12}$)-arylcarbamoyl, N-($C_7$–$C_{16}$)-aralkylcarbamoyl, N-($C_1$–$C_{10}$)-alkyl-N-($C_6$–$C_{16}$)-arylcarbamoyl, N-($C_1$–$C_{10}$)-alkyl-N-($C_7$–$C_{16}$)-aralkylcarbamoyl, N-(($C_1$–$C_{18}$)-alkoxy-($C_1$–$C_{10}$)alkyl)carbamoyl, N-(($C_6$–$C_{16}$)-aryloxy-($C_1$–$C_{10}$)-alkyl)carbamoyl, N-(($C_7$–$C_{16}$)-aralkyloxy-($C_1$–$C_{10}$)-alkyl)carbamoyl, N-($C_1$–$C_{10}$)-alkyl-N-(($C_1$–$C_{10}$)-alkoxy-($C_1$–$C_{10}$)-alkyl)carbamoyl, N-($C_1$–$C_{10}$)-alkyl-N-(($C_6$–$C_{12}$)-aryloxy-($C_1$–$C_{10}$)-alkyl)carbamoyl, N-($C_1$–$C_{10}$)-alkyl-N-(($C_7$–$C_{16}$)-aralkyloxy-($C_1$–$C_{10}$)-alkyl)carbamoyl, or CON(CH$_2$)$_h$, in which a CH$_2$ group can be replaced by O, S, N-($C_1$–$C_8$)-alkylimino, N-($C_3$–$C_8$)-cycloalkylimino, N-($C_3$–$C_8$)-cycloalkyl-($C_1$–$C_4$)-alkylimino, N-($C_6$–$C_{12}$)-arylimino, N-($C_7$–$C_{16}$)-aralkylimino or N-($C_1$–$C_4$)-alkoxy-($C_1$–$C_6$)-alkylimino and h is from 3 to 7, a carbamoyl radical of the formula II

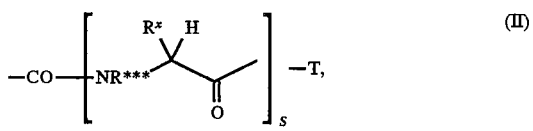

in which $R^*$ is the substituent of an α-amino acid to which the L- and D-amino acids belong, s is 1, 3, 4 or 5, and T is OH, OR or NR*R**, where $R^*$, $R^{}$ and $R^{*}$ are identical or different and are hydrogen, ($C_6$–$C_{12}$)-aryl, ($C_7$–$C_{11}$)-aralkyl, ($C_1$–$C_8$)-alkyl, ($C_3$–$C_8$)-cycloalkyl, (+)-dehydroabietyl, ($C_1$–$C_8$)-alkoxy-($C_1$–$C_8$)-alkyl, ($C_7$–$C_{12}$)-aralkoxy-($C_1$–$C_8$)-alkyl, ($C_6$–$C_{12}$)-aryloxy-($C_1$–$C_8$)-alkyl, ($C_1$–$C_{10}$)-alkanoyl, optionally substituted ($C_7$–$C_{16}$)-aralkanoyl or optionally substituted ($C_6$–$C_{12}$)-aroyl, or R* and R** together are —[CH$_2$]$_h$, in which a CH$_2$ group can be replaced by O, S, SO, SO$_2$, N-acylamino, N-($C_1$–$C_{10}$)-alkoxycarbonylamino, N-($C_1$–$C_8$)-alkylimino, N-($C_3$–$C_8$)-cycloalkylimino, N-($C_3$–$C_8$)-cycloalkyl-($C_1$–$C_4$)-alkylimino, N-($C_6$–$C_{12}$)-arylimino, N-($C_7$–$C_{16}$)-aralkylimino or N-($C_1$–$C_4$)-alkoxy-($C_1$–$C_6$)-alkylimino, and h is from 3 to 7, carbamoyloxy, N-($C_1$–$C_{12}$)-alkylcarbamoyloxy, N,N-di-($C_1$–$C_{12}$)-alkylcarbamoyloxy, N-($C_3$–$C_8$)-cycloalkylcarbamoyloxy, N-($C_6$–$C_{12}$)-arylcarbamoyloxy, N-($C_7$–$C_{16}$)-aralkylcarbamoyloxy, N-($C_1$–$C_{10}$)-alkyl-N-($C_6$–$C_{12}$)-arylcarbamoyloxy, N-($C_1$–$C_{10}$)-alkyl-N-($C_7$–$C_{16}$)-aralkylcarbamoyloxy, N-(($C_1$–$C_{10}$)-alkyl)carbamoyloxy, N-(($C_1$–$C_{12}$)-aryloxy-($C_1$–$C_{10}$)-alkyl)carbamoyloxy, N-(($C_7$–$C_{16}$)-aralkyloxy-($C_1$–$C_{10}$)-alkyl)carbamoyloxy, N-($C_1$–$C_{10}$)-alkyl-N-(($C_1$–$C_{10}$)-alkoxy-($C_1$–$C_{10}$)-alkyl)carbamoyloxy, N-($C_1$–$C_{10}$)-alkyl-N-(($C_6$–$C_{12}$)-aryloxy-($C_1$–$C_{10}$)-alkyl)carbamoyloxy, N-($C_1$–$C_{10}$)-alkyl-N-(($C_7$–$C_{16}$)-aralkyloxy-($C_1$–$C_{10}$)-alkyl) carbamoyloxy, amino, ($C_1$–$C_{12}$)-alkylamino, di-($C_1$–$C_{12}$)-alkylamino, ($C_3$–$C_8$)-cycloalkylamino, ($C_3$–$C_{12}$)-alkenylamino, ($C_3$–$C_{12}$)-alkynylamino, N-($C_1$–$C_{12}$)-arylamino, N-($C_7$–$C_{11}$)-aralkylamino, N-alkyl-aralkylamino, N-alkyl-arylamino, ($C_1$–$C_{12}$)-alkoxyamino, ($C_1$–$C_{12}$)-alkoxy-N-($C_1$–$C_{10}$)-alkylamino, ($C_1$–$C_{12}$)-alkanoylamino, ($C_3$–$C_8$)-cycloalkanoylamino, ($C_6$–$C_{12}$)-aroylamino, ($C_7$–$C_{16}$)-aralkanoylamino, ($C_1$–$C_{12}$)-alkanoyl-N-($C_1$–$C_{10}$)-alkylamino, ($C_3$–$C_8$)-cycloalkanoyl-N-($C_1$–$C_{10}$)-alkylamino, ($C_6$–$C_{12}$)-aroyl-N-($C_1$–$C_{10}$)-alkylamino, ($C_7$–$C_{11}$)-aralkanoyl-N-($C_1$–$C_{10}$)-alkylamino, ($C_1$–$C_{12}$)-alkanoylamino-($C_1$–$C_8$)-alkyl, ($C_3$–$C_8$)-cycloalkanoylamino-($C_1$–$C_8$)-alkyl, ($C_6$–$C_{12}$)-aroylamino-($C_1$–$C_8$)-alkyl, ($C_7$–$C_{16}$)-aralkanoylamino-($C_1$–$C_8$)-alkyl, amino-($C_1$–$C_{10}$)-alkyl, N-($C_1$–$C_{10}$)-alkylamino-($C_1$–$C_{10}$)-alkyl, N,N-di($C_1$–$C_{10}$)-alkylamino-($C_1$–$C_{10}$)-alkyl, ($C_3$–$C_8$)-cycloalkylamino-($C_1$–$C_{10}$)-alkyl, ($C_1$–$C_{20}$)-alkylmercapto, ($C_1$–$C_{20}$)-alkylsulfinyl, ($C_1$–$C_{20}$)-alkylsulfonyl, ($C_6$–$C_{12}$)-arylmercapto, ($C_6$–$C_{12}$)-arylsulfinyl, ($C_6$–$C_{12}$)-arylsulfonyl, ($C_7$–$C_{16}$)-aralkylmercapto, ($C_7$–$C_{16}$)-aralkylsulfinyl, ($C_7$–$C_{16}$)-aralkylsulfonyl, ($C_1$–$C_{12}$)-alkylmercapto-($C_1$–$C_6$)-alkyl, ($C_1$–$C_{12}$)-alkylsulfinyl-($C_1$–$C_6$)-alkyl, ($C_1$–$C_{12}$)-alkylsulfonyl-($C_1$–$C_6$)-alkyl, ($C_6$–$C_{12}$)-arylmercapto- $(C_1-C_6)$-alkyl, $(C_6-C_{12})$-arylsulfinyl -$(C_1-C_6)$-alkyl, $(C_6-C_{12})$-arylsulfonyl-$(C_1-C_6)$-alkyl, $(C_7-C_{16})$-aralkylmercapto-$(C_1-C_6)$-alkyl, $(C_7-C_{16})$-aralkylsulfinyl-$(C_1-C_6)$-alkyl, $(C_7-C_{16})$-aralkylsulfonyl-$(C_1-C_6)$-alkyl, sulfamoyl, N-$(C_1-C_{10})$-alkylsulfamoyl, N,N-di-$(C_1-C_{10})$-alkylsulfamoyl, $(C_3-C_8)$-cycloalkylsulfamoyl, N-$(C_6-C_{12})$-arylsulfamoyl, N-$(C_7-C_{16})$-aralkylsulfamoyl, N-$(C_1-C_{10})$-alkyl-N-$(C_6-C_{12})$-arylsulfamoyl, N-$(C_1-C_{10})$-alkyl-N-$(C_7-C_{16})$-aralkylsulfamoyl, $(C_1-C_{10})$-alkylsulfonamido, N-($(C_1-C_{10})$-alkyl)-$(C_1-C_{10})$-alkylsulfonamido, $(C_7-C_{16})$-aralkylsulfonamido or N-(($(C_1-C_{10})$-alkyl-$(C_7-C_{16})$-aralkylsulfonamido, where the radicals which contain an aryl radical can, for their part, be substituted on the aryl by from 1 to 5 identical or different radicals from the group:

hydroxyl, halogen, cyano, trifluoromethyl, nitro, carboxyl, $(C_1-C_{16})$-alkyl, $(C_3-C_8)$-cycloalkyl, $(C_3-C_8)$-cycloalkyl-$(C_1-C_{12})$-alkyl, $(C_3-C_8)$-cycloalkoxy, $(C_3-C_8)$-cycloalkyl-$(C_1-C_{12})$-alkoxy, $(C_3-C_8)$-cycloalkyloxy-$(C_1-C_{12})$-alkyl, $(C_3-C_8)$-cycloalkyloxy-$(C_1-C_{12})$-alkoxy, $(C_3-C_8)$-cycloalkyl-$(C_1-C_8)$-alkyl-$(C_1-C_6)$-alkoxy, $(C_3-C_8)$-cycloalkyl-$(C_1-C_8)$-alkoxy-$(C_1-C_6)$-alkyl, $(C_3-C_8)$-cycloalkyloxy-$(C_1-C_8)$-alkoxy-$(C_1-C_6)$-alkyl, $(C_3-C_8)$-cycloalkoxy-$(C_1-C_8)$alkoxy-$(C_1-C_8)$-alkoxy, $(C_6-C_{12})$-aryl, $(C_7-C_{16})$-aralkyl, $(C_2-C_{16})$-alkenyl, $(C_2-C_{12})$-alkynyl, $(C_1-C_{16})$-alkoxy, $(C_1-C_{16})$-alkenyloxy, $(C_1-C_{12})$-alkoxy-$(C_1-C_{12})$-alkyl, $(C_1-C_{12})$-alkoxy-$(C_1-C_{12})$-alkoxy, $(C_1-C_{12})$-alkoxy-$(C_1-C_8)$-alkoxy-$(C_1-C_8)$-alkyl, $(C_6-C_{12})$-aryloxy, $(C_7-C_{16})$-aralkyloxy, $(C_1-C_{12})$-aryloxy-$(C_1-C_6)$-alkoxy, $(C_7-C_{16})$-aralkoxy-$(C_1-C_6)$-alkoxy, $(C_1-C_8)$-hydroxyalkyl, $(C_6-C_{16})$-aryloxy-$(C_1-C_8)$-alkyl, $(C_7-C_{16})$-aralkoxy-$(C_1-C_8)$-alkyl, $(C_6-C_{12})$-aryloxy-$(C_1-C_8)$-alkoxy-$(C_1-C_6)$-alkyl, $(C_7-C_{12})$-aralkyloxy-$(C_1-C_8)$-alkoxy-$(C_1-C_6)$-alkyl, —O—[CH$_2$]$_x$—C$_f$H$_{(2f+1-g)}$F$_g$, —OCF$_2$Cl, —OCF$_2$—CHFCl, $(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_2-C_{12})$-alkenyloxycarbonyl, $(C_2-C_{12})$-alkynyloxycarbonyl, $(C_6-C_{12})$-aryloxy-$(C_1-C_6)$-alkoxycarbonyl, $(C_7-C_{16})$-aralkoxy-$(C_1-C_6)$-alkoxycarbonyl, $(C_3-C_8)$-cycloalkyl-$(C_1-C_6)$-alkoxycarbonyl, $(C_3-C_8)$-cycloalkoxy-$(C_1-C_6)$-alkoxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_2-C_{12})$-alkenylcarbonyloxy, $(C_2-C_{12})$-alkynylcarbonyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_2-C_{12})$-alkenyloxycarbonyloxy, $(C_2-C_{12})$-alkynyloxycarbonyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N,N-dicyclo-$(C_3-C_8)$-alkylcarbamoyl, N-$(C_1-C_{10})$-alkyl-N-$(C_3-C_8)$-cycloalkylcarbamoyl, N-(($(C_3-C_8)$-cycloalkyl-$(C_1-C_6)$-alkyl)carbamoyl, N-$(C_1-C_6)$-alkyl-N-(($(C_3-C_8)$-cycloalkyl-$(C_1-C_6)$-alkyl)carbamoyl, N-(+)-dehydroabietylcarbamoyl, N-$(C_1-C_6)$-alkyl-N-(+)-dehydroabietylcarbamoyl, N-$(C_6-C_{12})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-(($(C_1-C_{16})$-alkoxy-$(C_1-C_{10})$-alkyl)-carbamoyl, N-(($(C_6-C_{16})$-aryloxy-$(C_1-C_{10})$-alkyl)carbamoyl, N-(($(C_7-C_{16})$-aralkyloxy-$(C_1-C_{10})$-alkyl)carbamoyl, N-$(C_1-C_{10})$-alkyl-N-(($(C_1-C_{10})$-alkoxy-$(C_1-C_{10})$-alkyl)carbamoyl, N-$(C_1-C_{10})$-alkyl-N-(($(C_6-C_{12})$-aryloxy-$(C_1-C_{10})$-alkyl)carbamoyl, N-$(C_1-C_{10})$-alkyl-N-(($(C_7-C_{16})$-aralkyloxy-$(C_1-C_{10})$-alkyl)carbamoyl, CON(CH$_2$) h, in which a CH$_2$ group can be replaced by O, S, N-$(C_1-C_8)$-alkylimino, N-$(C_3-C_8)$-cycloalkylimino, N-$(C_3-C_8)$-cycloalkyl-$(C_1-C_4)$-alkylimino, N-$(C_6-C_{12})$-arylimino, N-$(C_7-C_{16})$-aralkylimino or N-$(C_1-C_4)$-alkoxy-$(C_1-C_6)$-alkylimino, and h is from 3 to 7, carbamoyloxy, N-$(C_1-C_{12})$-alkylcarbamoyloxy, N,N-di-$(C_1-C_{12})$-alkylcarbamoyloxy, N-$(C_3-C_8)$-cycloalkylcarbamoyloxy, N-$(C_6-C_{16})$-arylcarbamoyloxy, N-$(C_7-C_{16})$-aralkylcarbamoyloxy, N-$(C_1-C_{10})$-alkyl-N-$(C_6-C_{12})$-arylcarbamoyloxy, N-$(C_1-C_{10})$-alkyl-N-$(C_7-C_{16})$-aralkylcarbamoyloxy, N-(($(C_1-C_{10})$-alkyl)carbamoyloxy, N-(($(C_6-C_{12})$-aryloxy-$(C_1-C_{10})$-alkyl)carbamoyloxy, N-(($(C_7-C_{16})$-aralkyloxy-$(C_1-C_{10})$-alkyl)carbamoyloxy, N-$(C_1-C_{10})$-alkyl-N-(($(C_1-C_{10})$-alkoxy-$(C_1-C_{10})$-alkyl)carbamoyloxy, N-$(C_1-C_{10})$-alkyl-N-(($(C_6-C_{12})$-aryloxy-$(C_1-C_{10})$-alkyl)carbamoyloxy, N-$(C_1-C_{10})$-alkyl-N-(($(C_7-C_{16})$-aralkyloxy-$(C_1-C_{10})$-alkyl)carbamoyloxy, amino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N-$(C_6-C_{12})$-arylamino, N-$(C_7-C_{11})$-aralkylamino, N-alkyl-aralkylamino, N-alkyl-arylamino, $(C_1-C_{12})$-alkoxyamino, $(C_1-C_{12})$-alkoxy-N-$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N-$(C_1-C_{10})$-alkylamino, $(C_3-C_8)$-cycloalkanoyl-N-$(C_1-C_{10})$-alkylamino, $(C_1-C_{12})$-aroyl-N-$(C_1-C_{10})$-alkylamino, $(C_7-C_{11})$-aralkanoyl-N-$(C_1-C_{10})$-alkylamino, $(C_1-C_{12})$-alkanoylamino-$(C_1-C_8)$-alkyl, $(C_3-C_8)$-cycloalkanoylamino-$(C_1-C_8)$-alkyl, $(C_6-C_{12})$-aroylamino-$(C_1-C_8)$-alkyl, $(C_7-C_{16})$-aralkanoylamino-$(C_1-C_8)$-alkyl, amino-$(C_1-C_{10})$-alkyl, N-$(C_1-C_{10})$-alkylamino-$(C_1-C_{10})$-alkyl, N,N-di-$(C_1-C_{10})$-alkylamino-$(C_1-C_{10})$-alkyl, $(C_3-C_8)$-cycloalkylamino-$(C_1-C_{10})$-alkyl, $(C_1-C_{12})$-alkylmercapto, $(C_1-C_{12})$-alkylsulfinyl, $(C_1-C_{12})$-alkylsulfonyl, $(C_6-C_{16})$-arylmercapto, $(C_6-C_{16})$-arylsulfinyl, $(C_6-C_{16})$-arylsulfonyl, $(C_7-C_{16})$-aralkylmercapto, $(C_7-C_{16})$-aralkylsulfinyl or $(C_7-C_{16})$-aralkylsulfonyl, $R^1$ and $R^2$ or $R^2$ and $R^3$ forms chain [CH$_2$]$_o$ in which one or two CH$_2$ groups of the chain, which is saturated or unsaturated by a C=C double bond, are optionally replaced by O, S, SO, SO$_2$ or NR', and o is 3, 4 or 5, and R' is hydrogen, $(C_6-C_{12})$-aryl, $(C_1-C_8)$-alkyl, $(C_1-C_8)$-alkoxy-$(C_1-C_8)$-alkyl, $(C_7-C_{12})$-aralkoxy-$(C_1-C_8)$-alkyl, $(C_6-C_{12})$-aryloxy-$(C_1-C_8)$-alkyl, $(C_1-C_{10})$-alkanoyl, optionally substituted $(C_7-C_{16})$-aralkanoyl or optionally substituted ($C_6$–$C_{12}$)-aroyl, where the radicals $R^1$ and $R^2$ or $R^2$ and $R^3$, together with the pyridine or pyridazine carrying them, preferably form a 5, 6, 7, 8-tetrahydroisoquinoline ring, a 5, 6, 7, 8-tetrahydroquinoline ring or a 5, 6, 7, 8-tetrahydrocinnoline ring, or $R^1$ and $R^2$ or $R^2$ and $R^3$ form a carbocyclic or a heterocyclic, 5- or 6-membered aromatic ring, where the radicals $R^1$ and $R^2$ or $R^2$ and $R^3$, together with the pyridine or pyridazine carrying them, preferably form the following optionally substituted heterocyclic ring systems:

Thienopyridines,
Furanopyridines,
Pyridopyridines,
Pyrimidinopyridines,
Imidazopyridines,
Thiazolopyridines,
Oxazolopyridines,
Quinoline, isoquinoline and
Cinnoline, where quinoline, isoquinoline or cinnoline preferably satisfy the formulae 1a, 1b and 1c

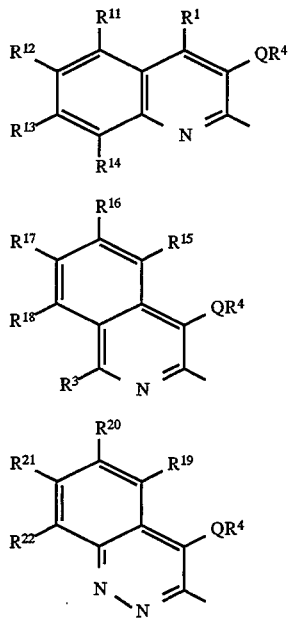

and the substituents $R^{11}$ to $R^{22}$, in each case independently of each other, have the meaning of $R^1$, $R^2$ and $R^3$, $R^4$ is, if Q is a bond, halogen, nitrile or trifluoromethyl, or, if Q is O, S or NR', a branched or unbranched ($C_1$–$C_{20}$)-alkyl radical, an unsubstituted, saturated fluoroalkyl radical of the formula $[CH_2]_x\text{—}C_fH_{(2f+1-g)}F_g$, a ($C_6$–$C_{16}$)-aryl radical, a ($C_7$–$C_{16}$)-aralkyl radical, a heteroaryl radical or a heteroaralkyl radical, where these radicals are substituted by one or more radicals from the group hydroxyl, halogen, cyano, trifluoromethyl, nitro, carboxyl, ($C_1$–$C_{12}$)-alkyl, ($C_3$–$C_8$)-cycloalkyl, ($C_3$–$C_8$)-cycloalkyl-($C_1$–$C_{12}$)-alkyl, ($C_3$–$C_8$)-cycloalkoxy, ($C_3$–$C_8$)-cycloalkyl-($C_1$–$C_{12}$)-alkoxy, ($C_3$–$C_8$)-cycloalkyloxy-($C_1$–$C_{12}$)-alkyl, ($C_3$–$C_8$)-cycloalkyloxy-($C_1$–$C_{12}$)-alkoxy, ($C_3$–$C_8$)-cycloalkyl-($C_1$–$C_8$)-alkyl-($C_1$–$C_6$)-alkoxy, ($C_3$–$C_8$)-cycloalkyl-($C_1$–$C_8$)-alkoxy-($C_1$–$C_6$)-alkyl, ($C_3$–$C_8$)-cycloalkyloxy-($C_1$–$C_8$)-alkoxy-($C_1$–$C_6$)-alkyl, ($C_3$–$C_a$)-cycloalkoxy-($C_1$–$C_8$)-alkoxy-($C_1$–$C_8$)-alkoxy, ($C_6$–$C_{12}$)-aryl, ($C_7$–$C_{16}$)-aralkyl, ($C_2$–$C_{12}$)-alkenyl, ($C_2$–$C_{12}$)-alkynyl, ($C_1$–$C_{12}$)-alkoxy, ($C_1$–$C_{12}$)-alkoxy-($C_1$–$C_{12}$)-alkyl, ($C_1$–$C_{12}$)-alkoxy-($C_1$–$C_{12}$)-alkoxy, ($C_1$–$C_{12}$)-alkoxy-($C_1$–$C_8$)-alkoxy-($C_1$–$C_8$)-alkyl, ($C_1$–$C_{12}$)-aryloxy, ($C_7$–$C_{16}$)-aralkyloxy, ($C_6$–$C_{12}$)-aryloxy-($C_1$–$C_6$)-alkoxy, ($C_7$–$C_{16}$)-aralkoxy-($C_1$–$C_6$)-alkoxy, ($C_1$–$C_8$)-hydroxyalkyl, ($C_6$–$C_{16}$)-aryloxy-($C_1$–$C_8$)-alkyl, ($C_1$–$C_{16}$)-aralkoxy-($C_1$–$C_8$)-alkyl, ($C_6$–$C_{12}$)-aryloxy-($C_1$–$C_8$)-alkoxy-($C_1$–$C_6$)-alkyl, ($C_7$–$C_{12}$)-aralkyloxy-($C_1$–$C_8$)-alkoxy-($C_1$–$C_6$)-alkyl, —O—$[CH_2\text{–}]_x$—$C_fH_{(2f+1-g)}F_g$, —$OCF_2Cl$, —$OCF_2$—$CHFCl$, ($C_1$–$C_{12}$)-alkylcarbonyl, ($C_3$–$C_8$)-cycloalkylcarbonyl, ($C_6$–$C_{12}$)-arylcarbonyl, ($C_7$–$C_{16}$)-aralkylcarbonyl, cinnamoyl, ($C_2$–$C_{12}$)-alkenylcarbonyl, ($C_2$–$C_{12}$)-aklynylcarbonyl, ($C_1$–$C_{12}$)-alkoxycarbonyl, ($C_1$–$C_{12}$)-alkoxy-($C_1$–$C_{12}$)-alkoxycarbonyl, ($C_6$–$C_{12}$)-aryloxycarbonyl, ($C_7$–$C_{16}$)-aralkoxycarbonyl, ($C_3$–$C_8$)-cycloalkoxycarbonyl, ($C_2$–$C_{12}$)-alkenyloxycarbonyl, ($C_2$–$C_{12}$)-alkynyloxycarbonyl, ($C_6$–$C_{12}$)-aryloxy-($C_1$–$C_6$)-alkoxycarbonyl, ($C_7$–$C_{16}$)-aralkoxy-($C_1$–$C_6$)-alkoxycarbonyl, ($C_3$–$C_8$)-cycloalkyl-($C_1$–$C_6$)-alkoxycarhonyl, ($C_3$–$C_8$)cycloalkoxy-($C_1$–$C_6$)-alkoxycarhonyl, ($C_1$–$C_{12}$)-alkylcarbonyloxy, ($C_3$–$C_8$-cycloalkylcarbonyloxy, ($C_6$–$C_{12}$)-arylcarbonyloxy, ($C_7$–$C_{16}$)-aralkylcarbonyloxy, cinnamoyloxy, ($C_2$–$C_{12}$)-alkenylcarbonyloxy, ($C_2$–$C_{12}$)-alkynylcarbonyloxy, ($C_1$–$C_{12}$)-alkoxycarbonyloxy, ($C_1$–$C_{12}$)-alkoxy-($C_1$–$C_{12}$)-alkoxycarbonyloxy, ($C_6$–$C_{12}$)-aryloxycarbonyloxy, ($C_7$–$C_{16}$)-aralkyloxycarbonyloxy, ($C_3$–$C_8$)-cycloalkoxycarbonyloxy, ($C_2$–$C_{12}$)-alkenyloxycarbonyloxy, ($C_2$–$C_{12}$)-alkynyloxycarbonyloxy, carbamoyl, N-($C_1$–$C_{12}$)-alkylcarbamoyl, N,N-di-($C_1$–$C_{12}$)-alkylcarbamoyl, N-($C_3$–$C_8$)-cycloalkylcarbamoyl, N,N-di-cyclo-($C_3$–$C_8$)-alkylcarbamoyl, N-($C_1$–$C_{10}$)-alkyl-N-($C_3$–$C_8$)-cycloalkylcarbamoyl, N-(($C_3$–$C_8$)-cycloalkyl-($C_1$–$C_6$)-alkyl)carbamoyl, N-($C_1$–$C_6$)-alkyl-N-(($C_3$–$C_8$)-cycloalkyl-($C_1$–$C_6$)-alkyl)carbamoyl, N-(+)-dehydroabietylcarbamoyl, N-($C_1$–$C_6$)-alkyl-N-(+)-dehydroabietylcarbamoyl, N-($C_6$–$C_{12}$)-arylcarbamoyl, N-($C_7$–$C_{16}$)-aralkylcarbamoyl, N-($C_1$–$C_{10}$)-alkyl-N-($C_6$–$C_{16}$)-arylcarbamoyl, N-($C_1$–$C_{10}$)-alkyl-N-($C_7$–$C_{16}$)-aralkylcarbamoyl, N(($C_1$–$C_{10}$)-alkoxy-($C_1$–$C_{10}$)-alkyl)carbamoyl, N-(($C_6$–$C_{16}$)-aryloxy-($C_1$–$C_{10}$)-alkyl)carbamoyl, N-(($C_7$–$C_{16}$)-aralkyloxy-($C_1$–$C_{10}$)-alkyl)carbamoyl, N-($C_1$–$C_{10}$)-alkyl-N(($C_1$–$C_{10}$)-alkoxy-($C_1$–$C_{10}$)-alkyl)carbamoyl, N-($C_1$–$C_{10}$)-alkyl-N-(($C_6$–$C_{12}$)-aryloxy-($C_1$–$C_{10}$)-alkyl)carbamoyl, N($C_1$–$C_{10}$)-alkyl-N-(($C_7$–$C_{16}$)-aralkyloxy-($C_1$–$C_{10}$)-alkyl)carbamoyl, $CON(CH_2)_h$, in which a $CH_2$ group can be replaced by O, S, N-($C_1$–$C_8$)-alkylimino, N-($C_3$–$C_8$)-cycloalkylimino, N-($C_3$–$C_8$)-cycloalkyl-($C_1$–$C_4$)-alkylimino, N-($C_6$–$C_{12}$)-arylimino, N-($C_7$–$C_{16}$)-aralkylimino or N-($C_1$–$C_4$)-alkoxy-($C_1$–$C_6$)-alkylimino, and h is from 3 to 7, or by a carbamoyl radical of the formula II

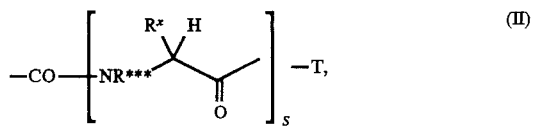

in which
R* is the substituent of an α-amino acid to which the L- and D-amino acids belong,
s is 1, 2, 3, 4 or 5, and
T is OH, OR or NR*R**, where
R*, R, and R* are identical or different and are hydrogen, $(C_6-C_{12})$-aryl, $(C_7-C_{11})$-aralkyl, $(C_1-C_8)$-alkyl, $(C_3-C_8)$-cycloalkyl, (+)-dehydroabietyl, $(C_1-C_8)$-alkoxy-$(C_1-C_8)$-alkyl, $(C_7-C_{12})$-aralkoxy-$(C_1-C_8)$-alkyl, $(C_6-C_{12})$-aryloxy-$(C_1-C_8)$-alkyl, $(C_1-C_{10})$-alkanoyl, optionally substituted $(C_7-C_{16})$-aralkanoyl or optionally substituted $(C_6-C_{12})$-aroyl, or
R* and R** together are $-[CH_2]_h$-, in which a $CH_2$ group can be replaced by O, S, SO, $SO_2$, N-acylamino, N-$(C_1-C_{10})$-alkoxycarbonylimino, N-$(C_1-C_8)$-alkylimino, N-$(C_3-C_8)$-cycloalkylimino, N-$(C_3-C_8)$-cycloalkyl-$(C_1-C_4)$-alkylimino, N-$(C_6-C_{12})$-arylimino, N-$(C_7-C_{16})$-aralkylimino or N-$(C_1-C_4)$-alkoxy-$(C_1-C_6)$-alkylimino, and h is from 3 to 7, or by carbamoyloxy, N-$(C_1-C_{12})$-alkylcarbamoyloxy, N,N-di-$(C_1-C_{12})$-alkylcarbamoyloxy, N-$(C_3-C_8)$-cycloalkylcarbamoyloxy, N-$(C_6-C_{12})$-arylcarbamoyloxy, N-$(C_7-C_{16})$-aralkylcarbamoyloxy, N-$(C_1-C_{10})$-alkyl-N-$(C_6-c12)$-arylcarbamoyloxy, N-$(C_1-C_{10})$-alkyl-N-$(C_7-C_{16})$-aralkylcarbamoyloxy, N-$((C_1-C_{10})$-alkyl)carbamoyloxy, N-$((C_6-C_{12})$-aryloxy-$(C_1-C_{10})$-alkyl)carbamoyloxy, N-$((C_7-C_{16})$-aralkyloxy-$(C_1-C_{10})$-alkyl)carbamoyloxy, N-$(C_1-C_{10})$-alkyl-N-$((C_1-C_{10})$-alkoxy-$(C_1-C_{10})$-alkyl)carbamoyloxy, N-$(C_1-C_{10})$-alkyl-N-$((C_6-C_{12})$-aryloxy-$(C_1-C_{10})$-alkyl)carbamoyloxy, N-$(C_1-C_{10})$-alkyl-N-$((C_7-C_{16})$-aralkyloxy-$(C_1-C_{10})$-alkyl)carbamoyloxy,
amino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N-$(C_6-C_{12})$-arylamino, N-$(C_7-C_{11})$-aralkylamino, N-alkyl-aralkylamino, N-alkyl-arylamino, $(C_1-C_{12})$-alkoxyamino, $(C_1-C_{12})$-alkoxy-N-$(C_1-C_{10})$-alkylamino,
$(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N-$(C_1-C_{10})$-alkylamino, $(C_3-C_8)$-cycloalkanoyl-N-$(C_1-C_{10})$-alkylamino, $(C_6-C_{12})$-aroyl-N-$(C_1-C_{10})$-alkylamino, $(C_7-C_{11})$-aralkanoyl-N-$(C_1-C_{10})$-alkylamino,
$(C_1-C_{12})$-alkanoylamino-$(C_1-C_8)$-alkyl, $(C_3-C_8)$-cycloalkanoylamino-$(C_1-C_8)$-alkyl, $(C_6-C_{12})$-aroylamino-$(C_1-C_8)$-alkyl, $(C_7-C_{16})$-aralkanoylamino-$(C_1-C_8)$-alkyl, amino-$(C_1-C_{10})$-alkyl, N-$(C_1-C_{10})$-alkylamino-$(C_1-C_{10})$-alkyl, N,N-di$(C_1-C_{10})$-alkylamino-$(C_1-C_{10})$-alkyl, $(C_3-C_8$-cycloalkylamino-$(C_1-C_{10})$-alkyl,
$(C_1-C_{12})$-alkylmercapto, $(C_1-C_{12})$-alkylsulfinyl, $(C_1-C_{12})$-alkylsulfonyl, $(C_6-C_{12})$-arylmercapto, $(C_6-C_2)$-arylsulfinyl, $(C_6-C_{12})$-arylsulfonyl, $(C_7-C_{16})$-aralkylmercapto, $(C_7-C_{16})$-aralkylsulfinyl, $(C_7-C_{16})$-aralkylsulfonyl,
sulfamoyl, N-$(C_1-C_{10})$-alkylsulfamoyl, N,N-di-$(C_1-C_{10})$-alkylsulfamoyl, $(C_3-C_8)$-cycloalkylsulfamoyl, N-$(C_6-C_{12})$-arylsulfamoyl, N-$(C_7-C_{16})$-aralkylsulfamoyl, N-$(C_1-C_{10})$-alkyl-N-$(C_6-C_{12})$-arylsulfamoyl, N-$(C_1-C_{10})$-alkyl-N-$(C_7-C_{16})$-aralkylsulfamoyl, $(C_1-C_{10})$-alkylsulfonamido, N-$((C_1-C_{10})$-alkyl)-$(C_1-C_{10})$-alkylsulfonamido, $(C_7-C_{16})$-aralkylsulfonamido or N-$((C_1-C_{10})$-alkyl-$(C_7-C_{16})$-aralkylsulfonamido, where the radicals which contain an aryl radical can, for their part, be substituted on the aryl by from 1 to 5 identical or different radicals from the group:
hydroxyl, halogen, cyano, trifluoromethyl, nitro, carboxyl, $(C_1-C_{12})$-alkyl, $(C_3-C_8)$-cycloalkyl, $(C_3-C_8)$-cycloalkyl-$(C_1-C_{12})$-alkyl, $(C_3-C_8)$-cycloalkoxy, $(C_3-C_8)$-cycloalkyl-$(C_1-C_{12})$-alkoxy, $(C_3-C_8)$-cycloalkyloxy-$(C_1-C_{12})$-alkyl, $(C_3-C_8)$-cycloalkyloxy-$(C_1-C_{12})$-alkoxy, $(C_3-C_8)$-cycloalkyl-$(C_1-C_8)$-alkyl-$(C_1-C_6)$-alkoxy, $(C_3-C_8)$-cycloalkyl-$(C_1-C_8)$-alkoxy-$(C_1-C_6)$-alkyl, $(C_3-C_8)$-cycloalkyloxy-$(C_1-C_8)$-alkoxy-$(C_1-C_6)$-alkyl, $(C_3-C_8)$-cycloalkoxy-$(C_1-C_8)$-alkoxy-$(C_1-C_8)$-alkoxy, $(C_6-C_{12})$-aryl, $(C_7-C_{16})$-aralkyl, $(C_2-C_{12})$-alkenyl, $(C_2-C_{12})$-alkynyl, $(C_1-C_{12})$-alkoxy, $(C_1-C_{12})$-alkoxy-$(C_1-C_{12})$-alkyl, $(C_1-C_{12})$-alkoxy-$(C_1-C_{12})$-alkoxy, $(C_1-C_{12})$-alkoxy-$(C_1-C_8)$-alkoxy-$(C_1-C_8)$-alkyl, $(C_6-C_{12})$-aryloxy, $(C_7-C_{16})$-aralkyloxy, $(C_6-C_{12})$-aryloxy-$(C_1-C_6)$-alkoxy, $(C_7-C_{16})$-aralkoxy-$(C_1-C_6)$-alkoxy, $(C_1-C_8)$-hydroxyalkyl, $(C_6-C_{16})$-aryloxy-$(C_1-C_8)$-alkyl, $(C_7-C_{16})$-aralkoxy-$(C_1-C_8)$-alkyl, $(C_6-C_{12})$-aryloxy-$(C_1-C_8)$-alkoxy-$(C_1-C_6)$-alkyl, $(C_7-C_{12})$-aralkyloxy-$(C_1-C_8)$-alkoxy-$(C_1-C_6)$-alkyl, $-O-[CH_2-]_x-C_fH_{(2f+1-g)}F_g$, $-OCF_2Cl$, $-OCF_2-$CHFCl,
$(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl,
$(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_2-C_{12})$-alkenyloxycarbonyl, $(C_2-C_{12})$-alkynyloxycarbonyl, $(C_6-C_{12})$-aryloxy-$(C_1-C_6)$-alkoxycarbonyl, $(C_7-C_{16})$-aralkoxy-$(C_1-C_6)$-alkoxycarbonyl, $(C_3-C_8)$-cycloalkyl-$(C_1-C_6)$-alkoxycarbonyl, $(C_3-C_8)$-cycloalkoxy-$(C_1-C_6)$-alkoxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_2-C_{12})$-alkenylcarbonyloxy, $(C_2-C_{12})$-alkynylcarbonyloxy,
$(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_2-C_{12})$-alkenyloxycarbonyloxy, $(C_2-C_{12})$-alkynyloxycarbonyloxy,
carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N,N-di-cyclo-$(C_3-C_8)$-alkylcarbamoyl, N-$(C_1-C_{10})$-alkyl-N-$(C_3-C_8)$-cycloalkylcarbamoyl, N-$((C_3-C_8)$-cycloalkyl-$(C_1-C_6)$-alkyl)carbamoyl, N-$(C_1-C_6)$-alkyl-N-$((C_3-C_8)$-cycloalkyl-$(C_1-C_6)$-alkyl)carbamoyl, N-(+)-dehydroabietylcarbamoyl, N-$(C_1-C_6)$-alkyl-N-(+)-dehydroabietylcarbamoyl, N-$(C_6-C_{12})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-$((C_1-C_{10})$-alkoxy-$(C_1-C_{10})$-alkyl)carbamoyl, N-$((C_6-C_{16})$-aryloxy-$(C_1-C_{10})$-alkyl)carbamoyl, N-$((C_7-C_{16})$-aralkyloxy-$(C_1-C_{10})$-alkyl)carbamoyl, N-$(C_1-C_{10})$-alkyl-N-( $(C_1-C_{10})$-alkoxy-$(C_1-C_{10})$-alkyl)carbamoyl, N-$(C_1-C_{10})$-alkyl-N-$((C_6-C_{12})$-aryloxy-$(C_1-C_{10})$-alkyl)carbamoyl, N-$(C_1-C_{10})$-alkyl-N-$((C_7-C_{16})$-aralkyloxy-$(C_1-C_{10})$-alkyl)carbamoyl, CON(CH$_2$)$_h$, in which a CH$_2$ group can be replaced by O, S, N-$(C_1-C_8)$-alkylimino, N-$(C_3-C_8)$-cycloalkylimino, N-$(C_3-C_8)$-cycloalkyl-$(C_1-C_4)$-alkylimino, N-$(C_6-C_{12})$-arylimino, N-$(C_7-C_{16})$-aralkylimino or N-$(C_1-C_4)$-alkoxy-$(C_1-C_6)$-alkylimino, and h is from 3 to 7, carbamoyloxy, N-$(C_1-C_{12})$-alkylcarbamoyloxy, N,N-di-$(C_1-C_{12})$-alkylcarbamoyloxy, N-$(C_3-C_8)$-cycloalkylcarbamoyloxy, N-$(C_6-C_{16})$-arylcarbamoyloxy, N-$(C_7-C_{16})$-aralkylcarbamoyloxy, N-$(C_1-C_{10})$-alkyl-N-$(C_6-C_{12})$-arylcarbamoyloxy, N-$(C_1-C_{10})$-alkyl-N-$(C_7-C_{16})$-aralkylcarbamoyloxy, N-$((C_1-C_{10})$-alkyl)carbamoyloxy, N-$((C_6-C_{12})$-aryloxy-$(C_1-C_{10})$-alkyl)carbamoyloxy, N-$((C_7-C_{16})$-aralkyloxy-$(C_1-C_{10})$-alkyl)carbamoyloxy, N-$(C_1-C_{10})$-alkyl-N-$((C_1-C_{10})$-alkoxy-$(C_1-C_{10})$-alkyl)carbamoyloxy, N-$(C_1-C_{10})$-alkyl-N-$((C_6-C_{12})$-aryloxy-$(C_1-C_{10})$-alkyl)carbamoyloxy, N-$(C_1-C_{10})$-alkyl-N-$((C_7-C_{16})$-aralkyloxy-$(C_1-C_{10})$-alkyl)carbamoyloxy, amino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N-$(C_6-C_{12})$-arylamino, N-$(C_7-C_{11})$-aralkylamino, N-alkyl-aralkylamino, N-alkyl-arylamino, $(C_1-C_{12})$-alkoxyamino, $(C_1-C_{12})$-alkoxy-N-$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N-$(C_1-C_{10})$-alkylamino, $(C_3-C_8)$-cycloalkanoyl-N-$(C_1-C_{10})$-alkylamino, $(C_6-C_{12})$-aroyl-N-$(C_1-C_{10})$-alkylamino, $(C_7-C_{11})$-aralkanoyl-N-$(C_1-C_{10})$-alkylamino, $(C_1-C_{12})$-alkanoylamino-$(C_1-C_8)$-alkyl, $(C_3-C_8)$-cycloalkanoylamino-$(C_1-C_8)$-alkyl, $(C_6-C_{12})$-aroylamino-$(C_1-C_8)$-alkyl, $(C_7-C_{16})$-aralkanoylamino-$(C_1-C_8)$-alkyl, amino-$(C_1-C_{10})$-alkyl, N-$(C_1-C_{10})$-alkylamino-$(C_1-C_{10})$-alkyl, N,N-di-$(C_1-C_{10})$-alkylamino-$(C_1-C_{10})$-alkyl, $(C_3-C_8)$-cycloalkylamino-$(C_1-C_{10})$-alkyl, $(C_1-C_{12})$-alkylmercapto, $(C_1-C_{12})$-alkylsulfinyl, $(C_1-C_{12})$-alkylsulfonyl, $(C_6-C_{16})$-arylmercapto, $(C_6-C_{16})$-arylsulfinyl, $(C_6-C_{16})$-arylsulfonyl, $(C_7-C_{16})$-aralkylmercapto, $(C_7-C_{16})$-aralkylsulfinyl or $(C_7-C_{16})$-aralkylsulfonyl, and R$^4$ is R", provided that Q has the meaning of NR', where R' and R" are identical or different and are hydrogen, $(C_6-C_{12})$-aryl, $(C_7-C_{11})$-aralkyl, $(C_1-C_8)$-alkyl, $(C_1-C_8)$-alkoxy-$(C_1-C_8)$-alkyl, $(C_7-C_{12})$-aralkoxy-$(C_1-C_8)$-alkyl, $(C_6-C_{12})$-aryloxy-$(C_1-C_8)$-alkyl, $(C_1-C_{10})$-alkanoyl, optionally substituted $(C_7-C_{16})$-aralkanoyl or optionally substituted $(C_6-C_{12})$-aroyl, or R' and R" together are —[CH$_2$]h, in which a CH$_2$ group can be replaced by O, S, N-acylimino or N-$(C_1-C_{10})$-alkoxycarbonylimino, and f is 1 to 8, g is 0 or 1 to (2f+1), x is 0 to 3, h is 3 to 7, including the physiologically active salts, where 3-benzyloxypyridine-2-carboxylic acid (L-threonyl methyl ester) amide, 3-benzyloxypyridine-2-carboxylic acid (L-threonyl(Fmoc-Phg) tert-butyl ester) amide, 3-benzyloxypyridine-2-carboxylic acid (L-threonyl tert-butyl ester) amide and 3-benzyloxypyridine-2-carboxylic acid (D-allothreonyl methyl ester) amide are excepted.

In general, aryl is understood to mean carbocyclic and heterocyclic aromatic ring systems. In particular, it is understood to include phenyl-substituted, biphenyl-substituted, naphthyl-substituted or unsubstituted 5- and 6-membered heteroaromatic rings having 1, 2 or 3 nitrogen and/or oxygen and/or sulfur atoms, such as derivatives of pyridyl, pyridazyl, pyrimidyl, pyrazyl, imidazolyl, triazolyl, thienyl, oxazolyl and thiazolyl, and their benzo-fused derivatives.

The invention also embraces salts of the compounds of the formula I.

The formation of salts with basic reagents can take place once, twice or three times on the acidic groups of the compounds of the formula I (i.e. radicals B, R$^1$, R$^2$, R$^3$ and R$^4$), in particular on the radical R$^2$.

Examples of reagents being used are alcoholates, hydroxides, carbonates, hydrogen carbonates, hydrogen phosphates, organometallic compounds of the alkali and alkaline earth elements, the elements of the third and fourth main groups of the periodic system, and the elements of the transition metals, amines, optionally substituted 1 to 3 times by $(C_1-C_8)$-hydroxyalkyl, $(C_1-C_4)$-alkoxy-$(C_1-C_8)$-alkyl, phenyl, benzyl or $(C_1-C_8)$-alkyl, which can be substituted 1 to 3 times by hydroxyl or $(C_1-C_4)$-alkoxy, for example tromethane (Tris buffer), 2-aminoethanol, 3-aminopropanol, hydroxylamine, dimethylhydroxylamine, 2-methoxyethylamine, 3-ethoxypropylamine, and basic amino acids and amino derivatives, such as amino acid esters, histidine, arginine and lysine, and their derivatives, and also pharmaceuticals which contain a basic group, such as, for example, ®Amiloride, ®Verapamil and beta blockers.

The invention also relates to the compounds according to Formula I, plus 3-benzyloxypyridine-2-carboxylic acid (L-threonyl methyl ester) amide, 3-benzyloxypyridine-2-carboxylic acid (L-threonyl(Fmoc-Phg) tert-butyl ester) amide, 3-benzyloxypyridine-2-carboxylic acid (L-threonyl tert-butyl ester) amide and 3-benzyloxypyridine-2-carboxylic acid (D-allothreonyl methyl ester) amide for use as pharmaceuticals.

Compounds of the formula I are of great interest, in which

Q is O, S, NR' or a bond,

X is O, is CR$^3$, or if R$^1$ and R$^2$ form a cycle,

Y is N or R$^3$, m is 0 or 1, and

G is the radical of an alcohol GOH.

Compounds of the formula I are very important in which

Q is O, NR' or a bond,

X is O, and

G is the radical of an alcohol GOH.

Compounds of the formula I are also very important in which Q is S, X is O and G is the radical of an alcohol GOH.

Compounds of the formula I are of particular importance in which

Q is O, NR' or a bond,

X is O,

Y is CR$^3$ or, if R$^1$ and R$^2$ form a cycle, N or CR$^3$, m is 0 or 1,

A is $(C_1-C_3)$-alkylene which is optionally substituted once by halogen, cyano, trifluoromethyl, $(C_1-C_6)$-alkyl, $(C_1-C_6)$-hydroxyalkyl, $(C_1-C_6)$-alkoxy or —O—[CH$_2$]$_x$—C$_f$H$_{(2f+1-g)}$F$_g$, or A is —CHR$^5$—, where R$^5$ is one of the substituents of the α-carbon atom of an α-amino acid, in particular of a natural L-amino acid and of its D-isomer, B is —CO$_2$G, where G is the radical of an alcohol GOH, in which G is a branched or unbranched, or cyclic, aliphatic (C$_1$–C$_{20}$)-alkyl radical, or a branched or unbranched, optionally cyclic, (C$_2$–C$_{20}$)-alkenyl radical, a retinyl radical, a (C$_2$–C$_{20}$)-alkynyl radical or a corresponding (C$_4$–C$_{20}$)-alkenynyl radical, where the radicals can in each case contain one or more multiple bonds, or a (C$_6$–C$_{16}$)-aryl radical, a (C$_7$–C$_{16}$)-aralkyl radical or a 5- or 6-membered, preferably nitrogen-containing, heteroaryl radical or a 5- or 6-membered, preferably nitrogen-containing, heteroaralkyl radical, where the above radicals are, in particular, one or more substituents from the group hydroxyl, halogen, cyano, trifluoromethyl, nitro, carboxyl, (C$_1$–C$_{12}$)-alkyl, (C$_3$–C$_8$)-cycloalkyl, (C$_5$–C$_8$)-cycloalkenyl, (C$_6$–C$_{12}$)-aryl, (C$_7$–C$_{16}$)-aralkyl, (C$_2$–C$_{12}$)-alkenyl, (C$_2$–C$_{12}$)-alkynyl, (C$_1$–C$_{12}$)-alkoxy, (C$_1$–C$_{12}$)-alkoxy-(C$_1$–C$_{12}$)alkyl, (C$_1$–C$_{12}$)-alkoxy-(C$_1$–C$_{12}$)alkoxy, (C$_6$–C$_{12}$)-aryloxy, (C$_7$–C$_{16}$)-aralkyloxy, (C$_1$–C$_8$)-hydroxyalkyl, —O—[CH$_2$–]$_x$—C$_f$H$_{(2f+1-g)}$F$_g$, —OCF$_2$Cl, —OCF$_2$—CHFCl, (C$_1$–C$_{12}$)-alkylcarbonyl, (C$_3$–C$_8$)-cycloalkylcarbonyl, (C$_6$–C$_{12}$)-arylcarbonyl, (C$_7$–C$_{16}$)-aralkylcarbonyl, cinnamoyl, (C$_2$–C$_{12}$)-alkenylcarbonyl, (C$_2$–C$_{12}$)-alkynylcarbonyl, (C$_1$–C$_{12}$)-alkoxycarbonyl, (C$_1$–C$_{12}$)-alkoxy-(C$_1$–C$_{12}$)-alkoxycarbonyl, (C$_6$–C$_{12}$)-aryloxycarbonyl, (C$_7$–C$_{16}$)-aralkoxycarbonyl, (C$_3$–C$_8$)-cycloalkoxycarbonyl, (C$_2$–C$_{12}$)-alkenyloxycarbonyl, (C$_2$–C$_{12}$)-alkynyloxycarbonyl, (C$_1$–C$_{12}$)-alkylcarbonyloxy, (C$_3$–C$_8$)-cycloalkylcarbonyloxy, (C$_6$–C$_{12}$)-arylcarbonyloxy, (C$_7$–C$_{16}$)-aralkylcarbonyloxy, cinnamoyloxy, (C$_2$–C$_{12}$)-alkenylcarbonyloxy, (C$_2$–C$_{12}$)-alkynylcarbonyloxy, (C$_1$–C$_{12}$)-alkoxycarbonyloxy, (C$_1$–C$_{12}$)-alkoxy-(C$_1$–C$_{12}$)-alkoxycarbonyloxy, (C$_6$–C$_{12}$)-aryloxycarbonyloxy, (C$_7$–C$_{16}$)-aralkyloxycarbonyloxy, (C$_3$–C$_8$)-cycloalkoxycarbonyloxy, (C$_2$–C$_{12}$)-alkenyloxycarbonyloxy, (C$_2$–C$_{12}$)-alkynyloxycarbonyloxy, carbamoyl, N-(C$_1$–C$_{12}$)-alkylcarbamoyl, N,N-di-(C$_1$–C$_{12}$)-alkylcarbamoyl, N-(C$_3$–C$_8$)-cycloalkylcarbamoyl, N-(C$_6$–C$_{16}$)-arylcarbamoyl, N-(C$_7$–C$_{16}$)-aralkylcarbamoyl, N-(C$_1$–C$_{10}$)-alkyl-N-(C$_6$–C$_{16}$) arylcarbamoyl, N-(C$_1$–C$_{10}$)-alkyl-N-(C$_7$–C$_{16}$)-aralkylcarbamoyl, N-((C$_1$–C$_{10}$)-alkoxy-(C$_1$–C$_{10}$)alkyl)carbamoyl, N-((C$_6$–C$_{12}$)-aryloxy-(C$_1$–C$_{10}$)alkyl)carbamoyl, N-((C$_7$–C$_{16}$)-aralkyloxy-(C$_1$–C$_{10}$)alkyl)carbamoyl, N-(C$_1$–C$_{10}$)-alkyl-N-((C$_1$–C$_{10}$)-alkoxy-(C$_1$–C$_{10}$)alkyl)carbamoyl, N-(C$_1$–C$_{10}$)-alkyl-N-((C$_6$–C$_{16}$)-aryloxy-(C$_1$–C$_{10}$)alkyl)carbamoyl, N-(C$_1$–C$_{10}$)-alkyl-N-((C$_7$–C$_{16}$)aralkyloxy-(C$_1$–C$_{10}$)alkyl)carbamoyl, carbamoyloxy, N-(C$_1$–C$_{12}$)-alkylcarbamoyloxy, N,N-di-(C$_1$–C$_{12}$)-alkylcarbamoyloxy, N-(C$_3$–C$_8$)-cycloalkylcarbamoyloxy, N-(C$_6$–C$_{12}$)-arylcarbamoyloxy, N-(C$_7$–C$_{16}$)-aralkylcarbamoyloxy, N-(C$_1$–C$_{10}$)-alkyl-N-(C$_6$–C$_{12}$) arylcarbamoyloxy, N-(C$_1$–C$_{10}$)-alkyl-N-(C$_7$–C$_{16}$)aralkylcarbamoyloxy, N-((C$_1$–C$_{10}$)alkyl)carbamoyloxy, N-((C$_6$–C$_{12}$)-aryloxy-(C$_1$–C$_{10}$)alkyl)carbamoyloxy, N-((C$_7$–C$_{16}$)-aralkyloxy-(C$_1$–C$_{10}$alkyl)carbamoyloxy, N-(C$_1$–C$_{10}$)-alkyl-N-((C$_1$–C$_{10}$)-alkoxy-(C$_1$–C$_{10}$alkyl)carbamoyloxy, N-(C$_1$–C$_{10}$)-alkyl-N-((C$_6$–C$_{12}$)-aryloxy-(C$_1$–C$_{10}$)alkyl)carbamoyloxy, N-(C$_1$–C$_{10}$)-alkyl-N-((C$_7$–C$_{16}$)-aralkyloxy-(C$_1$–C$_{10}$)-alkyl)carbamoyloxy, amino, (C$_1$–C$_{12}$)-alkylamino, di-(C$_1$–C$_{12}$)alkylamino, (C$_3$–C$_8$)-cycloalkylamino, (C$_2$–C$_{12}$)-alkenylamino, (C$_2$–C$_{12}$)-alkynylamino, N-(C$_6$–C$_{12}$)-arylamino, N-(C$_7$–C$_{11}$)-aralkylamino, N-alkyl-aralkylamino, N-alkyl-arylamino, (C$_1$–C$_{12}$)-alkoxyamino, (C$_1$–C$_{12}$)-alkoxy-N-(C$_1$–C$_{10}$)-alkylamino, (C$_1$–C$_{12}$)-alkanoylamino, (C$_3$–C$_8$)-cycloalkanoylamino, (C$_6$–C$_{12}$)-aroylamino, (C$_7$–C$_{16}$)-aralkanoylamino, (C$_1$–C$_{12}$)-alkanoyl-N-(C$_1$–C$_{10}$)-alkylamino, (C$_3$–C$_8$)-cycloalkanoyl-N-(C$_1$–C$_{10}$)-alkylamino, (C$_6$–C$_{12}$)-aroyl-N-(C$_1$–C$_{10}$)alkylamino, (C$_7$–C$_{11}$)-aralkanoyl-N-(C$_1$–C$_{10}$)-alkylamino, (C$_1$–C$_{12}$)-alkanoylamino-(C$_1$–C$_8$)-alkyl, (C$_3$–C$_8$)-cycloalkanoylamino-(C$_1$–C$_8$)alkyl, (C$_6$–C$_{12}$)-aroylamino-(C$_1$–C$_8$)-alkyl, (C$_7$–C$_{12}$)-aralkanoylamino-(C$_1$–C$_8$)-alkyl, amino-(C$_1$–C$_{10}$)-alkyl, N-(C$_1$–C$_{10}$)alkylamino-(C$_1$–C$_{10}$)-alkyl, N,N-di(C$_1$–C$_{10}$)-alkylamino-(C$_1$–C$_{10}$)alkyl, (C$_3$–C$_8$) cycloalkylamino-(C$_1$–C$_{10}$)alkyl, (C$_1$–C$_{12}$)-alkylmercapto, (C$_1$–C$_{12}$)-alkylsulfinyl, (C$_1$–C$_{12}$)-alkylsulfonyl, (C$_6$–C$_{16}$)-arylmercapto, (C$_6$–C$_{16}$)-arylsulfinyl, (C$_6$–C$_{12}$)-arylsulfonyl, (C$_7$–C$_{16}$)-aralkylmercapto, (C$_7$–C$_{16}$)-aralkylsulfinyl, (C$_7$–C$_{16}$)-aralkylsulfonyl, sulfamoyl, N-(C$_1$–C$_{10}$)-alkylsulfamoyl, N,N-di-(C$_1$–C$_{10}$)-alkylsulfamoyl, (C$_3$–C$_8$)-cycloalkylsulfamoyl, N-(C$_6$–C$_{12}$)-arylsulfamoyl, N-(C$_7$–C$_{16}$)-aralkylsulfamoyl, N-(C$_1$–C$_{10}$)-alkyl-N-(C$_6$–C$_{12}$)-arylsulfamoyl, N-(C$_1$–C$_{10}$)-alkyl-N-(C$_7$–C$_{16}$)-aralkylsulfamoyl, (Cl$_1$–C$_{10}$)-alkyl-sulfonamido, N-((C$_1$–C$_{10}$)alkyl)-(C$_1$–C$_{10}$)alkylsulfonamido, (C$_7$–C$_{16}$)-aralkylsulfonamido or N-((C$_1$–C$_{10}$)alkyl-(C$_7$–C$_{16}$)-aralkylsulfonamido, where the radicals which contain an aryl radical can, for their part, be substituted on the aryl by from 1 to 5 identical or different radicals from the group:

hydroxyl, halogen, cyano, trifluoromethyl, nitro, carboxyl, (C$_1$–C$_{12}$)-alkyl, (C$_3$–C$_8$-cycloalkyl, (C$_6$–C$_{12}$)-aryl, (C$_7$–C$_{16}$)-aralkyl, (C$_1$–C$_{12}$)-alkoxy, (C$_1$–C$_{12}$)-alkoxy-(C$_1$–C$_{12}$)alkyl, (C$_1$–C$_{12}$)-alkoxy-(C$_1$–C$_{12}$)-alkoxy, (C$_6$–C$_{12}$)-aryloxy, (C$_7$–C$_{16}$)-aralkyloxy, (C$_1$–C$_8$)-hydroxyalkyl, (C$_1$–C$_{12}$)-alkylcarbonyl, (C$_3$–C$_8$)-cycloalkylcarbonyl, (C$_1$–C$_{12}$)-arylcarbonyl, (C$_7$–C$_{16}$)-aralkylcarbonyl, (C$_1$–C$_{12}$)-alkoxycarhonyl, (C$_1$–C$_{12}$)-alkoxy-(C$_1$–C$_{12}$)-alkoxycarbonyl, (C$_6$–C$_{12}$)-aryloxycarbonyl, (C$_7$–C$_{16}$)-aralkoxycarbonyl, (C$_3$–C$_8$)-cycloalkoxycarbonyl, (C$_2$–C$_{12}$)-alkenyloxycarbonyl, (C$_2$–C$_{12}$)-alkynyloxycarbonyl, (C$_1$–C$_{12}$)-alkylcarbonyloxy, (C$_3$–C$_8$)-cycloalkylcarbonyloxy, (C$_6$–C$_{12}$)-arylcarbonyloxy, (C$_7$–C$_{16}$)-aralkylcarbonyloxy, cinnamoyloxy, (C$_2$–C$_{12}$)-alkenylcarbonyloxy, (C$_2$–C$_{12}$)-alkynylcarbonyloxy, (C$_1$–C$_{12}$)-alkoxycarbonyloxy, (C$_1$–C$_{12}$)-alkoxy-(C$_1$–C$_{12}$)-alkoxycarbonyloxy, (C$_6$–C$_{12}$)-aryloxycarbonyloxy, (C$_7$–C$_{16}$)-aralkyloxycarbonyloxy, (C$_3$–C$_8$)-cycloalkoxycarbonyloxy, (C$_2$–C$_{12}$)-alkenyloxycarbonyloxy, (C$_2$–C$_{12}$)-alkynyloxycarbonyloxy, carbamoyl, N-(C$_1$–C$_{12}$)-alkylcarbamoyl, N,N-di-(C$_1$–C$_{12}$)-alkylcarbamoyl, N-(C$_3$–C$_8$)-cycloalkylcarbamoyl, N-(C$_6$–C$_{12}$)-arylcarbamoyl, N-(C$_7$–C$_{16}$)-aralkylcarbamoyl, N-(C$_1$–C$_{10}$)-alkyl-N-(C$_6$–C$_{12}$)-arylcarbamoyl, N-(C$_1$–C$_{10}$)-alkyl-N-(C$_7$–C$_{16}$)-aralkylcarbamoyl, N-((C$_1$–C$_{10}$)-alkoxy-(C$_1$–C$_{10}$)alkyl)carbamoyl, N-((C$_6$–C$_{12}$)-aryloxy-(C$_1$–C$_{10}$)alkyl)carbamoyl, N-((C$_7$–C$_{16}$)-aralkyloxy-(C$_1$–C$_{10}$)alkyl)carbamoyl, N-(C$_1$–C$_{10}$)-alkyl-N-((C$_1$–C$_{10}$)-alkoxy-(C$_1$–C$_{10}$)alkyl)carbamoyl, N-(C$_1$–C$_{10}$)-alkyl-N-((C$_6$–C$_{12}$)-aryloxy-(C$_1$–C$_{10}$)

alkyl)carbamoyl, N-($C_1$-$C_{10}$)-alkyl-N-(($C_7$-$C_{16}$) aralkyloxy-($C_1$-$C_{10}$)alkyl)carbamoyl, carbamoyloxy, N-($C_1$-$C_{12}$)-alkylcarbamoyloxy, N,N-di-($C_1$-$C_{12}$)-alkylcarbamoyloxy, N-($C_3$-$C_8$)-cycloalkylcarbamoyloxy, N-($C_6$-$C_{12}$)-arylcarbamoyloxy, N-($C_7$-$C_{16}$)-aralkylcarbamoyloxy, N-($C_1$-$C_{10}$)-alkyl-N-($C_6$-$C_{12}$) arylcarbamoyloxy, N-($C_1$-$C_{10}$)-alkyl-N-($C_7$-$C_{16}$)-aralkylcarbamoyloxy, N-(($C_1$-$C_{10}$)alkyl)carbamoyloxy, N-(($C_6$-$C_{12}$)-aryloxy-($C_1$-$C_{10}$)alkyl)carbamoyloxy, N-(($C_7$-$C_{16}$)-aralkyloxy-($C_1$-$C_{10}$)alkyl)carbamoyloxy, N-($C_1$-$C_{10}$)-alkyl-N-(($C_1$-$C_{10}$)-alkoxy-($C_1$-$C_{10}$)alkyl) carbamoyloxy, N-($C_1$-$C_{10}$)-alkyl-N-(($C_6$-$C_{12}$)-aryloxy-($C_1$-$C_{10}$)alkyl)carbamoyloxy, N-($C_1$-$C_{10}$)-alkyl-N-(($C_7$-$C_{16}$)-aralkyloxy-($C_1$-$C_{10}$)-alkyl) carbamoyloxy, amino, ($C_1$-$C_{12}$)-alkylamino, di-($C_1$-$C_{12}$)alkylamino, ($C_3$-$C_8$)-cycloalkylamino, ($C_3$-$C_{12}$)-alkenylamino, ($C_3$-$C_{12}$)-alkynylamino, N-($C_6$-$C_{12}$)-arylamino, N-($C_7$-$C_{11}$)-aralkylamino, N-alkyl-aralkylamino, N-alkyl-arylamino, ($C_1$-$C_{12}$)-alkoxyamino, ($C_1$-$C_{12}$)-alkoxy-N-($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_{12}$)-alkanoyl-N-($C_1$-$C_{10}$)-alkylamino, ($C_3$-$C_8$)-cycloalkanoyl-N-($C_1$-$C_{10}$)-alkylamino, ($C_6$-$C_{12}$)-aroyl-N-($C_1$-$C_{10}$)-alkylamino, ($C_7$-$C_{11}$)-aralkanoyl-N-($C_1$-$C_{10}$)-alkylamino, ($C_1$-$C_{12}$)-alkanoylamino-($C_1$-$C_8$)-alkyl, ($C_3$-$C_8$)-cycloalkanoylamino-($C_1$-$C_8$)alkyl, ($C_6$-$C_{12}$)-aroylamino-($C_1$-$C_8$)-alkyl, ($C_7$-$C_{16}$)-aralkanoylamino-($C_1$-$C_8$)-alkyl, amino-($C_1$-$C_{10}$)-alkyl, N-($C_1$-$C_{10}$) alkylamino-($C_1$-$C_{10}$)-alkyl, N,N-di($C_1$-$C_{10}$)-alkylamino-($C_1$-$C_{10}$)alkyl, ($C_3$-$C_8$)-cycloalkylamino-($C_1$-$C_{10}$)alkyl, ($C_1$-$C_{12}$)-alkylmercapto, ($C_1$-$C_{12}$)-alkylsulfinyl, ($C_1$-$C_{12}$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{16}$)-aralkylmercapto, ($C_7$-$C_{16}$)-aralkylsulfinyl or ($C_7$-$C_{16}$)-aralkylsulfonyl, $R^2$ is hydrogen, ($C_1$-$C_{20}$)-alkyl, ($C_2$-$C_{20}$)-alkenyl, ($C_2$-$C_{20}$)-alkynyl, ($C_2$-$C_{20}$)-alkenyloxy, ($C_2$-$C_{20}$)-alkynyloxy, retinyloxy, ($C_1$-$C_{20}$)-alkoxy-($C_1$-$C_3$)-alkyl, ($C_2$-$C_{20}$)-alkenyloxy-($C_1$-$C_3$)-alkyl, retinyloxy-($C_1$-$C_3$)-alkyl, ($C_2$-$C_{20}$)-alkynyloxy-($C_1$-$C_3$)-alkyl, ($C_1$-$C_{20}$)-alkoxy, halogen, cyano, trifluoromethyl, ($C_1$-$C_8$)-hydroxyalkyl, ($C_1$-$C_{10}$)-alkanoyl, ($C_7$-$C_{12}$)-aralkanoyl, ($C_6$-$C_{12}$)-aroyl, —O—[$CH_2$]$_x$—$C_fH_{(2f+1-g)}F_g$, NR'R'', ($C_1$-$C_{10}$)-alkylmercapto, ($C_1$-$C_{10}$)-alkylsulfinyl, ($C_1$-$C_{10}$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{12}$)-aralkylmercapto, ($C_7$-$C_{12}$)-aralkylsulfinyl, ($C_7$-$C_{12}$)-aralkylsulfonyl, ($C_6$-$C_{12}$)-aryloxy, ($C_7$-$C_{16}$)-aralkyloxy, carboxyl, ($C_1$-$C_{20}$)-alkoxycarbonyl, ($C_1$-$C_{12}$)-alkoxy-($C_1$-$C_{12}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_2$-$C_{20}$)-alkenyloxycarbonyl, retinyloxycarbonyl, ($C_2$-$C_{20}$)-alkynyloxycarbonyl, ($C_3$-$C_8$)-cycloalkyl-($C_1$-$C_6$)-alkoxycarbonyl, ($C_3$-$C_8$)-cycloalkoxy-($C_1$-$C_6$)-alkoxycarbonyl, ($C_6$-$C_{12}$)-aryloxy-($C_1$-$C_6$)-alkoxycarbonyl, ($C_7$-$C_{16}$)-aralkoxy-($C_1$-$C_6$)-alkoxycarbonyl, carbamoyl, N-($C_1$-$C_{12}$)-alkylcarbamoyl, N,N-di-($C_1$-$C_{12}$)-alkylcarbamoyl, N-($C_3$-$C_8$)-cycloalkylcarbamoyl, N,N-dicyclo ($C_3$-$C_8$)-alkylcarbamoyl, N-($C_1$-$C_{10}$)-alkyl-N-($C_3$-$C_8$)-cycloalkylcarbamoyl, N-(($C_3$-$C_8$)-cycloalkyl-($C_1$-$C_6$)-alkyl)carbamoyl, N-($C_1$-$C_6$)-alkyl-N-(($C_3$-$C_8$)-cycloalkyl-($C_1$-$C_6$)-alkyl)carbamoyl, N-(+)-dehydroabietylcarbamoyl, N-($C_1$-$C_6$)-alkyl-N-(+)-dehydroabietylcarbamoyl, N-($C_6$-$C_{12}$)-arylcarbamoyl, N-($C_7$-$C_{16}$)-aralkylcarbamoyl, N-($C_1$-$C_{10}$)-alkyl-N-($C_6$-$C_{16}$)-arylcarbamoyl, N-($C_1$-$C_{10}$)-alkyl-N-($C_7$-$C_{16}$)-aralkylcarbamoyl, N-(($C_1$-$C_{12}$)-alkoxy-($C_1$-$C_{10}$)-alkyl)carbamoyl, N-(($C_6$-$C_{16}$)-aryloxy-($C_1$-$C_{10}$)-alkyl)carbamoyl, N-(($C_7$-$C_{16}$)-aralkyloxy-($C_1$-$C_{10}$)-alkyl)carbamoyl, N-($C_1$-$C_{10}$)-alkyl-N-(($C_1$-$C_{10}$)-alkoxy-($C_1$-$C_{10}$)-alkyl)carbamoyl, N-($C_1$-$C_{10}$)-alkyl-N-(($C_6$-$C_{12}$)-aryloxy-($C_1$-$C_{10}$)-alkyl)carbamoyl, N-($C_1$-$C_{10}$)-alkyl-N-(($C_7$-$C_{16}$)-aralkyloxy-($C_1$-$C_{10}$)-alkyl)carbamoyl, CON($CH_2$)$_h$, in which a $CH_2$ group can be replaced by O, S, N-($C_1$-$C_8$)-alkylimino, N-($C_3$-$C_8$)-cycloalkylimino, N-($C_3$-$C_8$)-cycloalkyl-($C_1$-$C_4$)-alkylimino, N-($C_6$-$C_{12}$)-arylimino, N-($C_7$-$C_{16}$)-aralkylimino or N-($C_1$-$C_4$)-alkoxy-($C_1$-$C_6$)-alkylimino, and h is from 3 to 7, where aryl is substituted in the manner as defined for $R^1$ and $R^3$, $R^1$ and $R^3$ are identical or different and are hydrogen, halogen, ($C_1$-$C_{12}$)-alkyl, ($C_1$-$C_{12}$)-alkoxy, —O—[$CH_2$]$_x$—$C_fH_{(2f+1-g)}Hal_g$, ($C_1$-$C_{12}$)-alkoxy-($C_1$-$C_{12}$)-alkyl, ($C_1$-$C_8$)-alkoxy-($C_1$-$C_{12}$)-alkoxy, ($C_1$-$C_{12}$)-alkoxy-($C_1$-$C_8$)-alkoxy-($C_2$-$C_6$)-alkyl, ($C_7$-$C_{11}$)-aralkyloxy, ($C_3$-$C_8$)-cycloalkyl, ($C_3$-$C_8$)-cycloalkyl-($C_1$-$C_8$)-alkyl, ($C_3$-$C_8$)-cycloalkyloxy, ($C_3$-$C_8$)-cycloalkyl-($C_1$-$C_8$)-alkoxy, ($C_3$-$C_8$)-cycloalkyloxy-($C_1$-$C_8$)-alkyl, ($C_3$-$C_8$)-cycloalkyloxy-($C_1$-$C_8$)-alkoxy, ($C_3$-$C_8$-cycloalkyl-($C_1$-$C_6$)-alkyl-($C_1$-$C_6$)-alkoxy, ($C_3$-$C_8$)-cycloalkyl-($C_1$-$C_6$)-alkoxy-($C_1$-$C_6$)-alkyl, ($C_3$-$C_8$)-cycloalkoxy-($C_1$-$C_6$)-alkoxy-($C_1$-$C_6$)-alkyl, $NR^YR^Z$, ($C_1$-$C_8$)-alkylmercapto, ($C_1$-$C_8$)-alkylsulfinyl or ($C_1$-$C_8$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{12}$)-aralkylmercapto, ($C_7$-$C_{11}$)-aralkylsulfinyl, ($C_7$-$C_{11}$)-aralkylsulfonyl, substituted ($C_6$-$C_{12}$)-aryloxy-($C_1$-$C_6$)-alkyl, ($C_7$-$C_{11}$)-aralkoxy-($C_1$-$C_6$)-alkyl, ($C_6$-$C_{12}$)-aryloxy-($C_1$-$C_6$)-alkoxy-($C_1$-$C_6$)-alkyl, ($C_7$-$C_{11}$)-aralkyloxy-($C_1$-$C_6$)-alkoxy-($C_1$-$C_6$)-alkyl, ($C_6$-$C_{12}$)-aryloxy, ($C_7$-$C_{11}$)-aralkyloxy, ($C_6$-$C_{12}$)-aryloxy-($C_1$-$C_6$)-alkoxy or ($C_7$-$C_{11}$)-aralkoxy-($C_1$-$C_6$)-alkoxy, where an aromatic radical carries by 1, 2, 3, 4 or 5 identical or different substituents from the group hydrogen, halogen, cyano, nitro, trifluoromethyl, ($C_1$-$C_{16}$)-alkyl, ($C_1$-$C_{16}$)-alkenyl, ($C_1$-$C_6$)-hydroxyalkyl, ($C_1$-$C_{16}$)-alkoxy, ($C_1$-$C_{16}$)-alkenyloxy, —O—[$CH_2$]$_x$—$C_fH_{(2f+1-g)}F_g$, —$OCF_2Cl$, —O—$CF_2$—$CHFCl$, ($C_1$-$C_6$)-alkylmercapto, ($C_1$-$C_6$)-alkylsulfinyl, ($C_1$-$C_6$)-alkylsulfonyl, ($C_1$-$C_6$)-alkylcarbonyl, ($C_1$-$C_6$)-alkoxycarbonyl, carbamoyl, N-($C_1$-$C_4$)-alkylcarbamoyl, N,N-di-($C_1$-$C_4$)-alkylcarbamoyl, ($C_1$-$C_6$)-alkylcarbonyloxy, ($C_3$-$C_8$)-cycloalkylcarbamoyl, phenyl, benzyl, phenoxy, benzyloxy, $NR^YR^Z$, phenylmercapto, phenylsulfonyl, phenylsulfinyl, sulfamoyl, N-($C_1$-$C_4$)-alkylsulfamoyl or N,N-di-($C_1$-$C_4$)-alkylsulfamoyl, or optionally carries up to 3 of the abovementioned identical or different substituents, and two adjacent carbon atoms of the aralkyloxy radical together carry a chain —[$CH_2$] and/or —CH═CH—CH═CH—, where a $CH_2$ group of the chain is optionally replaced by O, S, SO, $SO_2$ or NR', $R^1$ and $R^2$ or $R^2$ and $R^3$ form a chain [$CH_2$]$_o$, where o is 3, 4 or 5, or form, together with the pyridine or pyridazine carrying them, a cinnoline ring, a quinoline ring or an isoquinoline ring, $R^4$ is, if Q is a bond, fluorine, chlorine or bromine, or, if Q is O or NR', a branched or unbranched $(C_1-C_{20})$-alkyl radical, which can contain up to 3 C—C multiple bonds, an unsubstituted saturated fluoroalkyl radical of the formula $[CH_2]_x$—$C_fH_{(2f+1-g)}F_g$, a $(C_6-C_{16})$-aryl radical or a $(C_7-C_{16})$-aralkyl radical, which can contain up to 2 C—C multiple bonds in the alkyl chain, or an heteroaryl radical or an heteroaryl alkyl radical, where these radicals are substituted by one or more radicals from the group hydroxyl, fluorine, chlorine, cyano, trifluoromethyl, carboxyl, $(C_1-C_{12})$-alkyl, $(C_3-C_8)$-cycloalkyl, $(C_3-C_8)$-cycloalkyl-$(C_1-C_{12})$-alkyl, $(C_3-C_8)$-cycloalkoxy, $(C_3-C_8)$-cycloalkyl-$(C_1-C_{12})$-alkoxy, $(C_3-C_8)$-cycloalkyloxy-$(C_1-C_{12})$-alkyl, $(C_3-C_8)$-cycloalkyloxy-$(C_1-C_{12})$-alkoxy, $(C_3-C_8)$-cycloalkyl-$(C_1-C_8)$-alkyl-$(C_1-C_6)$-alkoxy, $(C_3-C_8)$-cycloalkoxy-$(C_1-C_8)$-alkoxy-$(C_1-C_8)$-alkoxy, $(C_6-C_{12})$-aryl, $(C_7-C_{16})$-aralkyl, $(C_2-C_{12})$-alkenyl, $(C_2-C_{12})$-alkynyl, $(C_1-C_{12})$-alkoxy, $(C_1-C_{12})$-alkoxy-$(C_1-C_{12})$-alkoxy, $(C_1-C_{12})$-alkoxy-$(C_1-C_8)$-alkoxy-$(C_1-C_8)$-alkyl, $(C_6-C_{12})$-aryloxy, $(C_7-C_{16})$-aralkyloxy, $(C_6-C_{12})$-aryloxy-$(C_1-C_6)$-alkoxy, $(C_7-C_{16})$-aralkoxy-$(C_1-C_6)$-alkoxy, $(C_1-C_8)$-hydroxyalkyl, —O—$[CH_2]_x$—$C_fH_{(2f+1-g)}F_g$,
$(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_2-C_{12})$-alkenyloxycarbonyl, $(C_2-C_{12})$-alkynyloxycarbonyl, $(C_3-C_8)$-cycloalkyl-$(C_1-C_6)$-alkoxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N,N-dicyclo-$(C_3-C_8)$-alkylcarbamoyl, N-$(C_1-C_{10})$-alkyl-N-$(C_3-C_8)$-cycloalkylcarbamoyl, N-(($C_3-C_8$)-cycloalkyl-$(C_1-C_6)$-alkyl)carbamoyl, N-$(C_1-C_6)$-alkyl-N-(($C_3-C_8$)-cycloalkyl-$(C_1-C_6)$-alkyl)carbamoyl, N-(+)-dehydroabietylcarbamoyl, N-$(C_1-C_6)$-alkyl-N-(+)-dehydroabietylcarbamoyl, N-$(C_6-C_{12})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-(($C_1-C_{10}$)-alkoxy-$(C_1-C_{10})$-alkyl)carbamoyl, N-(($C_6-C_{16}$)-aryloxy-$(C_1-C_{10})$-alkyl)carbamoyl, N-(($C_7-C_{16}$)-aralkyloxy-$(C_1-C_{10})$-alkyl)carbamoyl, CON(OH2) h in which a $CH_2$ group can be replaced by O, N-$(C_1-C_8)$-alkylimino, N-$(C_3-C_8)$-cycloalkylimino, N-$(C_3-C_8)$-cycloalkyl-$(C_1-C_4)$-alkylimino, N-$(C_6-C_{12})$-arylimino or N-$(C_7-C_{16})$-aralkylimino, and h is from 3 to 6,
where the radicals which contain an aryl radical can, for their part, be substituted on the aryl by from 1 to 5 identical or different radicals from the group:
hydroxyl, fluorine, chlorine, cyano, trifluoromethyl, carboxyl, $(C_1-C_{12})$-alkyl, $(C_3-C_8)$-cycloalkyl,$(C_1-C_6)$-alkoxy, $(C_3-C_8$-cycloalkoxy, $(C_1-C_{12})$-alkoxycarbonyl, N-$(C_1-C_6)$-alkylcarbamoyl, N,N-di-$(C_1-C_6)$-alkylcarbamoyl or N-$(C_3-C_8)$-cycloalkylcarbamoyl, and $R^4$ is R'', provided Q has the meaning of NR', where R' and R'' are identical or different and are hydrogen, $(C_1-C_8)$-alkyl, or $(C_7-C_{11})$-aralkyl which is optionally substituted once by fluorine, chlorine or $(C_1-C_4)$-alkoxy, $R^Y$ and $R^Z$ are identical or different and are hydrogen, $(C_6-C_{12})$-aryl, $(C_1-C_{10})$-alkyl, $(C_3-C_{10})$-cycloalkyl, $(C_1-C_8)$-alkoxy-$(C_1-C_8)$-alkyl, $(C_7-C_{12})$-aralkoxy-$(C_1-C_8)$-alkyl, $(C_6-C_{12})$-aryloxy-$(C_1-C_8)$-alkyl, $(C_1-C_{10})$-alkanoyl, optionally substituted $(C_7-C_{16})$-aralkanoyl or optionally substituted $(C_6-C_{12})$-aroyl, or $R^Y$ and $R^Z$ together are —$[CH_2]_h$—, in which a $CH_2$ group can be replaced by O, S, N-$(C_1-C_4)$-alkanoylimino or N-$(C_1-C_4)$-alkoxycarbonylimino, and f is 1 to 8, g is 0 or 1 to (2f+1), h is 3 to 6, x is 0 to 3, and n is 3 or 4.

Compounds of the formula I are preferred in which

Q is O, NR' or a bond,

X is O,

Y is $CR^3$ or, if $R^1$ and $R^2$ form a cycle, N or $CR^3$, m is 0,

A is $(C_1-C_3)$-alkylene which is optionally substituted once by halogen, cyano, trifluoromethyl, $(C_1-C_6)$-alkyl, $(C_1-C_6)$-hydroxyalkyl, $(C_1-C_6)$-alkoxy or —O—$[CH_2]_x$—$C_fH_{(2f+1-g)}F_g$ or A is —$CHR^5$—, where $R^5$ is one of the substituents of the α-carbon atom of an α-amino acid, in particular of a natural L-amino acid and of its D-isomer, B is $CO_2G$, where G is a branched or unbranched, or cyclic, aliphatic $(C_1-C_{20})$-alkyl radical, a retinyl radical or a branched or unbranched $(C_2-C_{20})$-alkenyl radical or a $(C_2-C_{20})$-alkynyl radical which can in each case contain one or more C—C multiple bonds, or a $(C_6-C_{12})$-aryl radical, a $(C_7-C_{11})$-aralkyl radical or a heteroaryl or heteroaralkyl radical, where the above radicals can carry one or two substituents from the group $(C_1-C_8)$-alkyl, $(C_3-C_8)$-cycloalkyl, fluorine, chlorine, hydroxyl, $(C_1-C_6)$-alkoxy, $(C_1-C_6)$-alkoxy-$(C_1-C_6)$-alkoxy, $(C_6-C_{12})$-aryloxy, $(C_7-C_{12})$-aralkyloxy, $(C_1-C_8)$-alkylcarbonyl, $(C_3-C_8)$-cycloalkylcarbonyl, $(C_6-C_{12})$-arylcarbonyl, $(C_7-C_{12})$-aralkylcarbonyl, $(C_1-C_8)$-alkoxycarbonyl, $(C_1-C_6)$-alkoxy-$(C_1-C_6)$-alkoxycarbonyl, $(C_6-C_{12})$-aryloxycarbonyl, $(C_7-C_{12})$-aralkoxycarbonyl, $(C_3-C_8)$-cycloalkoxycarbonyl, $(C_1-C_{20})$-alkylcarbonyloxy, $(C_3-C_8)$-cycloalkylcarbonyloxy, $(C_6-C_{12})$-arylcarbonyloxy, $(C_7-C_{12})$-aralkylcarbonyloxy, $(C_1-C_8)$-alkoxycarbonyloxy, $(C_1-C_8)$-alkoxy-$(C_1-C_6)$-alkoxycarbonyloxy, $(C_6-C_{12})$-aryloxycarbonyloxy, $(C_7-C_{12})$-aralkyloxycarbonyloxy, $(C_3-C_8)$-cycloalkoxycarbonyloxy, carbamoyl, N-$(C_1-C_8)$-alkylcarbamoyl, N,N-di-$(C_1-C_8)$-alkylcarbamoyl, N-$(C_3-C_8)$-cycloalkylcarbamoyl, N-(($C_1-C_6$)-alkoxy-$(C_1-C_6)$-alkyl)carbamoyl, amino, $(C_1-C_6)$-alkylamino, di-$(C_1-C_6)$-alkylamino, $(C_3-C_8)$-cycloalkylamino, N-$(C_6-C_{12})$-arylamino, N-$(C_7-C_{11})$-aralkylamino, N-$(C_1-C_5)$-alkyl-$(C_6-C_{12})$-arylamino, $(C_1-C_8)$-alkanoylamino, $(C_3-C_8)$-cycloalkanoylamino, $(C_6-C_{12})$-aroylamino, $(C_7-C_{12})$-aralkanoylamino, $(C_1-C_8)$-alkanoyl-N-$(C_1-C_6)$-alkylamino, $(C_3-C_8)$-cycloalkanoyl-N-$(C_1-C_6)$-alkylamino, $(C_6-C_{12})$-aroyl-N-$(C_1-C_6)$-alkylamino or $(C_7-C_{11})$-aralkanoyl-N-$(C_1-C_6)$-alkylamino, and where the radicals which contain an aryl radical are substituted, in particular, by up to 3 substituents from the group hydroxyl, fluorine, chlorine, cyano, trifluoromethyl, $(C_1-C_6)$-alkyl, $(C_3-C_8)$-cycloalkyl, $(C_1-C_8)$-alkoxy, $(C_1-C_6)$-alkylcarbonyl, $(C_3-C_8)$-cycloalkylcarbonyl, $(C_1-C_6)$-alkoxycarbonyl, $(C_3-C_8)$-cycloalkoxycarbonyl, $(C_1-C_6)$-alkylcarbonyloxy, $(C_3-C_8)$-cycloalkylcarbonyloxy, $(C_1-C_6)$- alkoxycarbonyloxy, $(C_3-C_8)$-cycloalkoxycarbonyloxy, carbamoyl, N-$(C_1-C_6)$-alkylcarbamoyl, N,N-di-$(C_1-C_6)$-alkylcarbamoyl, N-$(C_3-C_8)$-cycloalkylcarbamoyl, N-($(C_1-C_6)$-alkoxy-$(C_1-C_6)$alkyl)carbamoyl, N-$(C_1-C_6)$-alkyl-N-(($(C_1-C_6)$-alkoxy-$(C_1-C_6)$alkyl)carbamoyl, carbamoyloxy, N-$(C_1-C_6)$-alkylcarbamoyloxy, N,N-di-$(C_1-C_6)$-alkylcarbamoyloxy, N-$(C_3-C_8)$-cycloalkylcarbamoyloxy, $(C_1-C_6)$-alkanoylamino, $(C_3-C_8)$-cycloalkanoylamino, $(C_1-C_6)$alkylmercapto, $(C_1-C_6)$-alkylsulfinyl, $(C_1-C_6)$-alkylsulfonyl, and $R^2$ is hydrogen, $(C_1-C_{20})$-alkyl, $(C_2-C_{20})$-alkenyl, $(C_2-C_{20})$-alkenyloxy, $(C_2-C_{20})$-alkynyloxy, retinyloxy, $(C_1-C_{20})$-alkoxy-$(C_1-C_3)$-alkyl, $(C_1-C_{20})$-alkoxy-$(C_1-C_3)$-alkyl, $(C_2-C_{20})$-alkenyloxy-$(C_1-C_3)$-alkyl, retinyloxy-$(C_1-C_3)$-alkyl, $(C_2-C_{20})$-alkynyloxy-$(C_1-C_3)$-alkyl, $(C_1-C_{20})$-alkoxy, halogen, cyano, trifluoromethyl, $(C_1-C_8)$-hydroxyalkyl, $(C_1-C_{10})$-alkanoyl, $(C_7$-alkylsulfinyl, $(C_1-C_{10})$-alkylsulfonyl, $(C_6-C_{12})$-aralkanoyl, $(C_6-C_{12})$-aroyl, —O—$[CH_2]_x$—$C_fH_{(2f+1-g)}F_g$, NR'R'', $(C_1-C_{10})$-alkylmercapto, $(C_1-C_{10})$-mercapto, $(C_6-C_{12})$-arylsulfinyl, $(C_6-C_{12})$-arylsulfonyl, $(C_7-C_{12})$-aralkylmercapto, $(C_7-C_{12})$-aralkylsulfinyl, $(C_7-C_{12})$-aralkylsulfonyl, $(C_6-C_{12})$-aryloxy, $(C_7-C_{16})$-aralkyloxy, carboxyl, $(C_1-C_{20})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_2-C_{20})$-alkenyloxycarbonyl, retinyloxycarbonyl, $(C_2-C_{20})$-alkynyloxycarbonyl, $(C_3-C_8)$-cycloalkyl-$(C_1-C_6)$-alkoxycarbonyl, $(C_3-C_8)$-cycloalkoxy-$(C_1-C_6)$-alkoxycarbonyl, $(C_6-C_{12})$-aryloxy-$(C_1-C_6)$-alkoxycarbonyl, $(C_7-C_{16})$-aralkoxy-$(C_1-C_6)$-alkoxycarbonyl, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N,N-dicyclo $(C_3-C_8)$-alkylcarbamoyl, N-$(C_1-C_{10})$-alkyl-N-$(C_3-C_8)$-cycloalkylcarbamoyl, N-(($(C_3-C_8)$-cycloalkyl-$(C_1-C_6)$-alkyl)carbamoyl, N-$(C_1-C_6)$-alkyl-N-(($(C_3-C_8)$-cycloalkyl-$(C_1-C_6)$-alkyl)carbamoyl, N-(+)-dehydroabietylcarbamoyl, N-$(C_1-C_6)$-alkyl-N-(+)-dehydroabietylcarbamoyl, N-$(C_6-C_{12})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{12})$-aralkylcarbamoyl, N-(($(C_1-C_{12})$-alkoxy-$(C_1-C_{10})$-alkyl)carbamoyl, N-(($(C_6-C_{16})$-aryloxy-$(C_1-C_{10})$-alkyl)carbamoyl, N-(($(C_7-C_{16})$-aralkyloxy-$(C_1-C_{10})$-alkyl)carbamoyl, N-$(C_1-C_{10})$-alkyl-N-($(C_1-C_{10})$-alkoxy-$(C_1-C_{10})$-alkyl)carbamoyl, N-$(C_1-C_{10})$-alkyl-N-(($(C_6-C_{12})$-aryloxy-$(C_1-C_{10})$-alkyl)carbamoyl, N-$(C_1-C_{10})$-alkyl-N-(($(C_7-C_{16})$-aralkyloxy-$(C_1-C_{10})$-alkyl)carbamoyl, or $CON(CH_2)_h$, in which a $CH_2$ group can be replaced by O, S, N-$(C_1-C_8)$-alkylimino, N-$(C_3-C_8)$-cycloalkylimino, N-$(C_3-C_8)$-cycloalkyl-$(C_1-C_4)$-alkylimino, N-$(C_6-C_{12})$-arylimino, N-$(C_7-C_{16})$-aralkylimino or N-$(C_1-C_4)$-alkoxy-$(C_1-C_6)$-alkylimino, and h is from 3 to 6, where aryl is substituted in the manner as defined for $R^1$ and $R^3$, $R^2$ and $R^3$ are identical or different and are hydrogen, halogen, $(C_1-C_{12})$-alkyl, $(C_1-C_{12})$-alkoxy, —O—$[CH_2]_x$—$C_fH_{(2f+1-g)}Hal_g$, $(C_1-C_{12})$-alkoxy-$(C_1-C_{12})$-alkyl, $(C_1-C_8)$-alkoxy-$(C_1-C_{12})$-alkoxy, $(C_1-C_{12})$-alkoxy-$(C_1-C_8)$-alkoxy-$(C_2-C_6)$-alkyl, $(C_7-C_{11})$-aralkyloxy, $(C_3-C_8)$-cycloalkyl, $(C_3-C_8)$-cycloalkyl-$(C_1-C_8)$-alkyl, $(C_3-C_8)$-alkyloxy, $(C_3-C_8)$-cycloalkyl-$(C_1-C_8)$-alkoxy, $(C_3-C_8)$-cycloalkyloxy-$(C_1-C_8)$-alkyl, $(C_3-C_8)$-cycloalkyloxy-$(C_1-C_8)$-alkoxy, $(C_3-C_8)$-cycloalkyl-$(C_1-C_6)$-alkyl-$(C_1-C_6)$-alkoxy, $(C_3-C_8)$-cycloalkyl-$(C_1-C_6)$-alkoxy-$(C_1-C_6)$-alkyl, $(C_3-C_8)$-cycloalkoxy-$(C_1-C_6)$-alkoxy-$(C_1-C_6)$-alkyl, $NR^YR^Z$, $(C_1-C_8)$-alkylmercapto, $(C_1-C_8)$-alkylsulfinyl or $(C_1-C_8)$-alkylsulfonyl, $(C_6-C_{12})$-arylmercapto, $(C_6-C_{12})$-arylsulfinyl, $(C_6-C_{12})$-arylsulfonyl, $(C_7-C_{12})$-aralkylmercapto, $(C_7-C_{11})$-aralkylsulfinyl, $(C_7-C_{11})$-aralkylsulfonyl, substituted $(C_6-C_{12})$-aryloxy-$(C_1-C_6)$-alkyl, $(C_7-C_{11})$-aralkoxy-$(C_1-C_6)$-alkyl, $(C_6-C_{12})$-aryloxy-$(C_1-C_6)$-alkoxy-$(C_1-C_6)$-alkyl, $(C_7-C_{11})$-aralkyloxy-$(C_1-C_6)$-alkoxy-$(C_1-C_6)$-alkyl, $(C_6-C_{12})$-aryloxy, $(C_7-C_{11})$-aralkyloxy, $(C_6-C_{12})$-aryloxy-$(C_1-C_6)$-alkoxy or $(C_7-C_{11})$-aralkoxy-$(C_1-C_6)$-alkoxy, where an aromatic radical carries by 1, 2, 3, 4 or 5 identical or different substituents from the group hydrogen, halogen, cyano, nitro, trifluoromethyl, $(C_1-C_{12})$-alkyl, $(C_1-C_{12})$-alkenyl, $(C_1-C_6)$-hydroxyalkyl, $(C_1-C_{12})$-alkoxy, $(C_1-C_{12})$-alkenyloxy, —O—$[CH_2]_x$—$C_fH_{(2f+1-g)}F_g$, —$OCF_2Cl$, —O—$CF_2$—$CHFCl$, $(C_1-C_6)$-alkylmercapto, $(C_1-C_6)$-alkylsulfinyl, $(C_1-C_6)$-alkylsulfonyl, $(C_1-C_6)$-alkylcarbonyl, $(C_1-C_6)$-alkoxycarbonyl, carbamoyl, N-$(C_1-C_4)$-alkylcarbamoyl, N,N-di-$(C_1-C_4)$-alkylcarbamoyl, $(C_1-C_6)$-alkylcarbonyloxy, $(C_3-C_8)$-cycloalkylcarbamoyl, phenyl, benzyl, phenoxy, benzyloxy, $NR^YR^Z$, phenylmercapto, phenylsulfonyl, phenylsulfinyl, sulfamoyl, N-$(C_1-C_4)$-alkyl, sulfamoyl or N,N-di-$(C_1-C_4)$-alkylsulfamoyl, or optionally carries up to 3 of the abovementioned identical or different substituents, and two adjacent carbon atoms of the aralkyloxy radical together carry a chain —$[CH_2-]$— and/or —CH=CH—CH=CH—, where a $CH_2$ group of the chain is optionally replaced by O, S, SO, $SO_2$ or $NR^Y$, $R^1$ and $R^2$ or $R^2$ and $R^3$ can form a chain $[CH_2]_o$, where o is 3, 4 or 5, and $R^4$, provided Q is a bond, is chlorine or, if Q is O or NR', is a branched or unbranched $(C_1-C_{10})$-alkyl radical, which can contain one or two C—C multiple bonds, or an unsubstituted fluoroalkyl radical of the formula —$[CH_2]_x$—$C_fH_{(2f+1-g)}F_9$ or $(C_1-C_8)$-alkoxy-$(C_1-C_6)$-alkyl, $(C_1-C_6)$-alkoxy-$(C_1-C_4)$-alkoxy-$(C_1-C_4)$-alkyl or a radical of the formula Z, $$—[CH_2]_v—[O]_w—[CH_2]_t—E \quad (Z),$$

where E is a substituted phenyl radical of the formula F

(F)

or a $(C_3-C_8)$-cycloalkyl radical, where v is 0, 1, 2, 3, 4, 5 or 6, w is 0 or 1, and t is 0, 1, 2 or 3, with the restriction that v is not equal to 0 if w is 1, and $R^6$, $R^7$, $R^8$, $R^9$ and $R^{10}$ are identical or different and are hydrogen, halogen, cyano, nitro, trifluoromethyl, $(C_1-C_6)$-alkyl, $(C_3-C_8)$-cycloalkyl, $(C_1-C_6)$-alkoxy, —O—$[CH_2-]_x$—$C_fH_{(2f+1-g)}F_g$, —$OCF_2Cl$, —O—$CF_2$—$CHFCl$, $(C_1-C_6)$-alkylmercapto, $(C_1-C_6)$-hydroxyalkyl, $(C_1-C_6)$-alkoxy-$(C_1-C_6)$-alkoxy, $(C_1-C_6)$-alkoxy-$(C_1-C_6)$-alkyl, $(C_1-C_6)$-alkylsulfinyl, $(C_1-C_6)$-alkylsulfonyl, $(C_1-C_6)$-alkylcarbonyl, $(C_1-C_8)$-alkoxycarbonyl, carbamoyl, N-$(C_1-C_8)$-alkylcarbamoyl, N,N-di-$(C_1-C_8)$-alkylcarbamoyl, $(C_7-C_{11})$-aralkylcarbamoyl which is optionally substituted by fluorine, chlorine, bromine, trifluoromethyl or $(C_1-C_6)$-alkoxy, N-$(C_3-C_8)$-cycloalkylcarbamoyl, N-$(C_3-C_8)$-cycloalkyl-$(C_1-C_4)$-alkylcarbamoyl, $(C_1-C_6)$-alkylcarbonyloxy, phenyl, benzyl, phenoxy, benzyloxy, $NR^Y R^Z$, such as amino, anilino, N-methylanilino, phenylmercapto, phenylsulfonyl, phenylsulfinyl, sulfamoyl, N-$(C_1-C_8)$-alkylsulfamoyl or N,N-di-$(C_1-C_8)$-alkylsulfamoyl, or two adjacent substituents together are a chain $-[CH_{2-}]_n$ or $-CH=CH-CH=CH-$, where a $CH_2$ group of the chain is optionally replaced by O, S, SO, $SO_2$ or $NR^Y$, and where a heteroaryl radical can carry1, 2 or 3 substituents, and a cycloalkyl radical one substituent, from the above group, and $R^4$ is R", provided Q has the meaning of NR', where R' is hydrogen or methyl, and R" is benzyl, and if $R^1$ and/or $R^3$ have the meaning of $(C_6-C_{12})$-aryloxy, $(C_7-C_{11})$-aralkyloxy, $(C_6-C_{12})$-aryloxy-$(C_1-C_6)$-alkoxy, $(C_7-C_{11})$-aralkoxy-$(C_1-C_6)$-alkoxy or a corresponding radical containing terminal cycloalkyl groups, this radical is preferably then a radical of the formula D $$OZ \qquad (D),$$

or if $R^1$ and/or $R^3$ have the meaning of $(C_7-C_{11})$-aralkyl, $(C_6-C_{12})$-aryloxy-$(C_1-C_6)$-alkyl, $(C_7-C_{11})$-aralkoxy-$(C_1-C_6)$-alkyl or a corresponding radical containing terminal cycloalkyl groups, this radical is preferably then a radical of the formula Z, $R^Y$ and $R^Z$ are identical or different and are hydrogen, $(C_6-C_{12})$-aryl, $(C_1-C_{10})$-alkyl, $(C_3-C_{10})$-cycloalkyl, $(C_1-C_8)$-alkoxy-$(C_1-C_8)$-alkyl, $(C_7-C_{12})$-aralkoxy-$(C_1-C_8)$-alkyl, $(C_6-C_{12})$-aryloxy-$(C_1-C_8)$-alkyl, $(C_1-C_{10})$-alkanoyl, optionally substituted $(C_7-C_{16})$-aralkanoyl or optionally substituted $(C_6-C_{12})$-aroyl, or $R^Y$ and $R^Z$ are together $-[CH_2]_h-$, in which a $CH_2$ group can be replaced by O, S, N-$(C_1-C_4)$-alkanoylimino or N-$(C_1-C_4)$-alkoxycarbonylimino, and f is 1 to 8, g is 0 or 1 to (2f+1), h is 3 to 6, x is 0 to 3, and n is 3 or 4.

Compounds of the formula I are particularly preferred in which

Q is O,

X is O,

Y is $CR^3$ and, additionally, N if $R^1$ and $R^2$ form cycle, m is 0,

A is $-CHR^5-$, where $R^5$ is the substituent of the α-carbon atom of an α-amino acid, in particular of natural L-amino acid or its D-isomer, B is $CO_2G$, where G is a branched or unbranched, or cyclic, aliphatic $(C_1-C_{18})$-alkyl radical, a $(C_3-C_8)$-cycloalkyl-$(C_1-C_8)$-alkyl radical, a branched or unbranched $(C_2-C_{18})$-alkenyl radical, such as, for example, a geranyl or farnesyl radical, or a retinyl radical, or $(C_2-C_{18})$-alkynyl radical, a phenyl radical, benzyl radical, phenethyl radical, phenylpropyl radical or phenylbutyl radical, where the above radicals contain a substituent from the group hydroxyl, $(C_1-C_4)$-alkoxy, acyloxy, $(C_1-C_6)$-alkylcarbonyloxy, $(C_3-C_8)$-cycloalkylcarbonyloxy, benzoyloxy, $(C_7-C_{16})$-phenylalkylcarbonyloxy or $(C_3-C_8)$-cycloalkoxycarbonyloxy, $R^2$ is hydrogen, bromine, chlorine, cyano, $(C_1-C_{18})$-alkyl, $(C_1-C_8)$-alkoxy, $(C_1-C_{18})$-alkoxymethyl, $(C_2-C_{18})$-alkenyloxymethyl, $(C_2-C_{18})$-alkynlyloxymethyl, carbamoyl, N-$(C_1-C_{10})$-alkylcarbamoyl, N-$((C_1-C_{12})$-alkoxy-$(C_1-C_4)$-alkyl)carbamoyl, N,N-di-$(C_1-C_8)$-alkylcarbamoyl, N-$(C_3-C_8)$-cycloalkylcarbamoyl, N-$(C_6-C_{12})$-phenylcarbamoyl, N-$(C_7-C_{12})$-phenylalkylcarbamoyl, N-$(C_1-C_6)$-alkyl-N-$(C_6-C_{12})$phenylcarbamoyl, N-$(C_1-C_6)$-alkyl-N-$(C_7-C_{12})$-phenylalkylcarbamoyl, N-$((C_1-C_6)$-alkoxy-$(C_1-C_6)$-alkyl)carbamoyl, carboxyl, $(C_1-C_{20})$-alkoxycarbonyl, $(C_2-C_{20})$-alkenyloxycarbonyl, retinyloxycarbonyl, $(C_3-C_8)$-cycloalkoxycarbonyl, $(C_3-C_8)$-cycloalkyl-$(C_1-C_6)$-alkoxycarbonyl, $(C_3-C_8)$-cycloalkoxy-$(C_1-C_6)$-alkoxycarbonyl, phenyl-$(C_1-C_6)$-alkoxycarbonyl, phenoxy-$(C_1-C_6)$-alkoxycarbonyl or benzyloxy-$(C_1-C_6)$-alkoxycarbonyl, where a phenyl radical is substituted in the manner as defined for $R^1$ and $R^3$, and one of the radicals $R^2$ or $R^3$ is hydrogen and the other a radical from the group hydrogen, fluorine, chlorine, $(C_1-C_8)$-alkyl, $(C_1-C_{10})$-alkoxy, $(C_5-C_6)$-cycloalkyl, $(C_5-C_6)$-cycloalkyl-$(C_1-C_6)$-alkyl, $(C_5-C_6)$-cycloalkyloxy, $(C_5-C_6)$-cycloalkyl-$(C_1-C_6)$-alkoxy, $(C_5-C_6)$-cycloalkyloxy-$(C_1-C_6)$-alkyl, $(C_5-C_6)$-cycloalkyloxy-$(C_1-C_6)$-alkoxy, $(C_5-C_6)$-cycloalkyl-$(C_1-C_4)$-alkyl-$(C_1-C_4)$-alkoxy, $(C_5-C_6)$-cycloalkyl-$(C_1-C_4)$-alkoxy-$(C_1-C_2)$-alkyl, $(C_5-C_6)$-cycloalkoxy-$(C_1-C_4)$-alkoxy-$(C_1-C_2)$-alkyl, $-O-[CH_2]_x-C_fH_{(2f+1-g)}F_g$, $(C_1-C_6)$-alkoxy-$(C_1-C_6)$-alkyl, $(C_1-C_6)$-alkoxy-$(C_1-C_6)$-alkoxy, $(C_1-C_6)$-alkoxy-$(C_1-C_4)$-alkoxy-$(C_1-C_2)$-alkyl, substituted $(C_6-C_{12})$-phenoxy, $(C_7-C_{11})$-phenylalkyloxy, $(C_6-C_{12})$-phenoxy-$(C_1-C_6)$-alkoxy or $(C_7-C_{11})$-phenylalkoxy-$(C_1-C_6)$-alkoxy, phenoxy-$(C_1-C_4)$-alkyl, $(C_7-C_{11})$-phenylalkyloxy-$(C_1-C_4)$-alkyl, phenoxy-$(C_1-C_4)$-alkoxy-$(C_1-C_2)$-alkyl or $(C_7-C_{11})$-phenylalkyloxy-$(C_1-C_4)$-alkoxy-$(C_1-C_2)$-alkyl, where an aromatic radical is substituted by 1, 2 or 3 identical or different substitutuents from the group fluorine, chlorine, cyano, trifluoromethyl, $(C_1-C_{12})$-alkyl, $(C_2-C_{12})$-alkenyl, $(C_2-C_{12})$-alkenyloxy or $(C_1-C_{12})$-alkoxy, $R^1$ and $R^2$, with the pyridine carrying them, form a 5,6,7,8-tetrahydroisoquinoline ring, $R^4$ is a branched or unbranched $(C_1-C_{10})$-alkyl radical, $(C_1-C_4)$-alkoxy-$(C_1-C_4)$-alkyl or a radical of the formula Z, $$-[CH_2]_v-[O]_w-[CH_2]_t-E \qquad (Z),$$

where E is a substituted phenyl radical of the formula F

or a ($C_3$-$C_8$-cycloalkyl radical, where v is 0, 1, 2 or 3, w is 0, and t can be 0 or 1, and in which $R^6$, $R^7$, $R^8$, $R^9$ and $R^{10}$ are identical or different and are hydrogen, fluorine, chlorine, cyano, trifluoromethyl, ($C_1$-$C_6$)-alkyl, ($C_1$-$C_6$)-alkoxy, —O—$[CH_2]_x$—$C_fH_{(2f+1-g)}F_g$, N-($C_1$-$C_8$)-alkylcarbamoyl, N,N-di-($C_1$-$C_6$)-alkylcarbamoyl, N-($C_3$-$C_6$)-cycloalkylcarbamoyl, N-(+)-dehydroabietylaminocarbonyl, or ($C_7$-$C_{11}$)-phenylalkylcarbamoyl, which is optionally substituted by fluorine, chlorine, trifluoromethyl or ($C_1$-$C_6$)-alkoxy, or where $R^6$ and $R^7$ or $R^7$ and $R^8$, together with the phenyl ring carrying them, form naphthalene derivatives.

If $R^1$ or $R^3$ has the meaning of ($C_6$-$C_{12}$)-phenoxy, ($C_7$-$C_{11}$)-phenylalkyloxy, ($C_6$-$C_{12}$)-phenoxy-($C_1$-$C_6$)-alkoxy, ($C_7$-$C_{11}$)-phenylalkoxy-($C_1$-$C_6$)-alkoxy, ($C_5$-$C_6$)-cycloalkyloxy, ($C_5$-$C_6$)-cycloalkyl-($C_1$-$C_6$)-alkoxy, ($C_5$-$C_6$)-cycloalkoxy-($C_1$-$C_6$)-alkoxy or ($C_5$-$C_6$)-cycloalkyl-($C_1$-$C_4$)-alkyl-($C_1$-$C_4$)-alkoxy, this radical is then, especially, a radical of the formula D

or if $R^1$ or $R^3$ has the meaning of phenyl, phenoxy-($C_1$-$C_6$)-alkyl, ($C_7$-$C_{11}$)-phenylalkyl, ($C_7$-$C_{11}$)-phenylalkyloxy-($C_1$-$C_4$)-alkyl, ($C_5$-$C_6$)-cycloalkyl, ($C_5$-$C_6$)-cycloalkyl-($C_1$-$C_6$)-alkyl, ($C_5$-$C_6$)-cycloalkoxy-($C_1$-$C_4$)-alkyl, ($C_5$-$C_6$)-cycloalkyl-($C_1$-$C_4$)-alkoxy-($C_1$-$C_2$)-alkyl or ($C_5$-$C_6$)-cycloalkoxy-($C_1$-$C_4$)-alkoxy-($C_1$-$C_2$)-alkyl, this radical is then, especially, a radical of the formula Z in which, in both cases, v is 1, 2, 3 or 4, w is 0 and t is 0, or v is 1, 2, 3 or 4, w is 1 and t is 0, or v is 1, 2, 3 or 4, w is 1, t is 1, and f is 1 to 4, g is 0 or 1 to (2f+1), x is 0 or 1.

Compounds of the formula I are very particularly preferred in which

Q is O,

X is O,

Y is $CR^3$, m is 0,

A is a —$CH_2$— group which can be substituted by a methyl group,

B is —$CO_2G$, where

G is a branched or unbranched, or cyclic, aliphatic ($C_1$-$C_{18}$)-alkyl radical, a ($C_3$-$C_8$-cycloalkyl-($C_1$-$C_4$)-alkyl radical or a branched or unbranched ($C_2$-$C_{18}$)-alkenyl radical, where the above radicals can contain a substituent from the group hydroxyl, ($C_1$-$C_4$)-alkoxy, acyloxy, ($C_1$-$C_6$)-alkylcarbonyloxy, ($C_3$-$C_8$)-cycloalkylcarbonyloxy, benzoyloxy, ($C_7$-$C_{16}$)-phenylalkylcarbonyloxy or ($C_3$-$C_8$)-cycloalkoxycarbonyloxy, or G is a phenol radical, benzyl radical, phenethyl radical, phenylpropyl radical or phenylbutyl radical, $R^2$ is hydrogen, ($C_1$-$C_8$)-alkoxy, ($C_1$-$C_{16}$)-alkoxymethyl, ($C_2$-$C_{16}$)-alkenyloxymethyl, retinyloxymethyl, N-($C_1$-$C_{10}$)-alkylcarbamoyl, N-(($C_1$-$C_{12}$)-alkoxy-($C_1$-$C_3$)-alkyl)carbamoyl, N,N-di-($C_1$-$C_8$)-alkylcarbamoyl, N-($C_5$-$C_6$)-cycloalkylcarbamoyl, N-phenylcarbamoyl, N-phenyl-($C_1$-$C_4$)-alkylcarbamoyl, carboxyl, ($C_1$-$C_{16}$)-alkoxycarbonyl, ($C_2$-$C_{16}$)-alkenyloxycarbonyl, retinyloxycarbonyl, ($C_5$-$C_6$)-cycloalkoxycarbonyl, ($C_5$-$C_6$)-cycloalkyl-($C_1$-$C_6$)-alkoxycarbonyl or phenyl-($C_1$-$C_6$)-alkoxycarbonyl, where a phenol radical is substituted in the manner as defined for $R^1$ and $R^2$, and one of the radicals $R^1$ or $R^3$ is hydrogen and the other radical is a radical from the group hydrogen, ($C_1$-$C_{10}$)-alkoxy, ($C_5$-$C_6$)-cycloalkyloxy, ($C_5$-$C_6$)-cycloalkyl-($C_1$-$C_2$)-alkoxy, —O—$[CH_2]_x$—$C_fH_{(2f+1-g)}F_g$, ($C_1$-$C_4$)-alkoxy-($C_1$-$C_4$)-alkoxy, substituted ($C_6$-$C_{12}$)-phenoxy, ($C_7$-$C_{11}$)-phenylalkyloxy, ($C_6$-$C_{12}$)-phenoxy-($C_1$-$C_4$)-alkoxy or ($C_7$-$C_{11}$)-phenylalkoxy-($C_1$-$C_4$)-alkoxy, where an aromatic radical is substituted by 1, 2 or 3 identical or different substituents from the group fluorine, chlorine, cyano, trifluoromethyl, ($C_1$-$C_{10}$)-alkyl, ($C_1$-$C_{10}$)-alkoxy or ($C_1$-$C_{10}$)-alkenyloxy, end $R^4$ is a branched or unbranched ($C_1$-$C_8$)-alkyl radical or a radical of the formula Z,

where E is a substituted phenyl radical of the formula F

or a ($C_3$-$C_8$)-cycloalkyl radical, where v is 0, 1, 2 or 3, w is 0, and t can be 0 or 1, and in which $R^6$, $R^6$, $R^7$, $R^9$ and $R^{10}$ are identical or different and are hydrogen, fluorine, chlorine, cyano, trifluoromethyl, ($C_1$-$C_6$)-alkyl, ($C_1$-$C_6$)-alkoxy, —O—$[CH_{2-}]_x$—$C_fH_{(2f+1-g)}F_g$, N-($C_1$-$C_8$)-alkylcarbamoyl, N,N-di-($C_1$-$C_6$)-alkylcarbamoyl, N-($C_3$-$C_6$)-cycloalkylcarbamoyl, N-(+)-dehydroabietylaminocarbonyl substituted benzyl radical, and f is 1 to 4, g is 0 or 1 to (2f+1) and x is 0 or 1.

Compounds of the formula I are particularly preferred in which

Q is O,

X is O,

Y is $CR^3$, m is 0,

B is —$CO_2G$, where

G is a branched or unbranched aliphatic ($C_1$-$C_{16}$)-alkyl radical, a 2-cyclohexylethyl radical, a ($C_1$-$C_4$)-alkoxy-($C_1$-$C_2$)-alkyl radical, a branched or unbranched ($C_2$-$C_{10}$)-alkenyl radical, a phenyl radical, benzyl radical, phenethyl radical, phenylpropyl radical or phenylbutyl radical, A is a —$CH_2$-group, $R^1$ is hydrogen, ($C_1$-$C_6$)-alkoxy or —O—$[CH_2]_x$—$C_fH_{(2f+1-g)}F_g$, R² is hydrogen, N-(C₁-C₁₀)-alkylcarbamoyl, N-((C₁-C₁₂)-alkoxy-(C₁-C₃)-alkyl)carbamoyl, N,N-di-(C₁-C₈)-alkylcarbamoyl, N-(C₅-C₆)-cycloalkylcarbamoyl, N-phenylcarbamoyl, N-phenyl-(C₁-C₄)-alkylcarbamoyl, carboxyl, (C₁-C₁₆)-alkoxycarbonyl, (C₂-C₁₆)-alkenyloxycarbonyl, retinyloxycarbonyl, (C₅-C₆)-cycloalkoxycarbonyl, (C₅-C₆)-cycloalkyl-(C₁-C₆)-alkoxycarbonyl or phenyl-(C₁-C₆)-alkoxycarbonyl, where a phenyl radical is substituted by 1 or 2 identical or different substituents from the group fluorine, chlorine, cyano, trifluoromethyl, (C₁-C₁₀)-alkyl, (C₁-C₁₀)-alkenyloxy or (C₁-C₁₀)-alkoxy, and R³ is hydrogen, (C₁-C₅)-alkoxy or (C₅-C₆)-cycloalkyl-(C₁-C₂)-alkoxy, where one of the substituents R¹ and R³ is hydrogen, R⁴ is a branched or unbranched (C₁-C₆)-alkyl radical, or a 2-phenylethyl radical, or a benzyl radical substituted by 1 or 2 radicals from the group fluorine, chlorine, cyano, trifluoromethyl, (C₁-C₆)-alkyl, (C₁-C₆)-alkoxy, —O—[CH₂₋]ₓ—C_fH_{(2f+1-g)}F_g, N-(C₁-C₈)-alkylcarbamoyl, N,N-di-(C₁-C₆)-alkylcarbamoyl, N-(C₃-C₆)-cycloalkylcarbamoyl or N-(+)-dehydroabietylaminocarbonyl, and f is 1 to 4, g is 0 or 1 to (2f+1) and x is 1.

Compounds of the formula I are preferred to the highest degree in which

Q is O,

X is O,

Y is CR³, m is 0,

A is a —CH₂-group,

B is —CO₂G, where

G is a branched or unbranched aliphatic (C₁-C₁₆)-alkyl radical or a benzyl radical, R¹ is hydrogen, R² is hydrogen, N-(C₁-C₁₀)-alkylcarbamoyl, N-((C₁-C₁₂)-alkoxy-(C₁-C₃)-alkyl)carbamoyl, N-cyclohexylcarbamoyl, N-phenylcarbamoyl, N-(phenyl-(C₁-C₂)-alkyl)carbamoyl, where, in the last two cases, the phenyl radical can carry a fluorine substituent, (C₁-C₁₀)-alkyl substituent or (C₁-C₁₀)-alkoxy substituent, carboxyl, (C₁-C₁₆)-alkoxycarbonyl, (C₂-C₁₆)-alkenyloxycarbonyl, retinyloxycarbonyl, (C₅-C₆)-cycloalkoxycarbonyl or benzyloxycarbonyl, R³ hydrogen, (C₁-C₅)-alkoxy or 2-(cyclohexyl)ethyloxy, where one of the substituents R² and R³ is hydrogen, R⁴ is a branched or unbranched (C₁-C₄)-alkyl radical or a benzyl radical which is substituted once by fluorine, chlorine, trifluoromethyl, (C₁-C₄)-alkyl or (C₁-C₃)-alkoxy.

Compounds of the formula I are also preferred to the highest degree in which

Q is S,

X is O,

Y is CR³, m is 0,

A is a —CH₂— group,

B is —CO₂G, where

G is a branched or unbranched aliphatic (C₁-C₁₆)-alkyl radical or a benzyl radical, R¹ is hydrogen, R² is hydrogen, N-(C₁-C₁₀)-alkylcarbamoyl, N-((C₁-C₁₂)-alkoxy-(C₁-C₃)alkyl)carbamoyl, N-cyclohexylcarbamoyl, N-phenylcarbamoyl, N-(phenyl-(C₁-C₂)alkyl)carbamoyl, where, in the last two cases, the phenyl radical can carry a fluorine substituent, (C₁-C₁₀)-alkyl substituent or (C₁-C₁₀)-alkoxy substituent, carboxyl, (C₁-C₁₆)-alkoxycarbonyl, (C₂-C₁₆)-alkenyloxycarbonyl, retinyloxycarbonyl, (C₅-C₆)-cycloalkoxycarbonyl or benzyloxycarbonyl, R³ is hydrogen, (C₁-C₅)-alkoxy or 2-(cyclohexyl) ethyloxy, where one of the substituents R² and R³ is hydrogen, and R⁴ is a branched or unbranched (C₁-C₄)-alkyl radical or a benzyl radical which is substituted once by fluorine, chlorine, trifluoromethyl, (C₁-C₄)-alkyl or (C₁-C₃)-alkoxy.

The compounds of the formula I are also preferred to the highest degree in which Q is S, X is O, Y is CR³, m is 0, A is a —CH₂— group, B is —CO₂G, where G is a branched or unbranched aliphatic (C₁-C₁₆)-alkyl radical or a benzyl radical, R¹ is hydrogen, R² is carboxyl or (C₁-C₁₆)-alkoxycarbonyl, R³ is hydrogen, and R⁴ is a branched or unbranched (C₁-C₄)-alkyl radical.

Compounds of the formula I are also preferred to the highest degree in which

Q is O,

X is O,

Y is CR³, where R³ is hydrogen, m is 0,

A is a —CH₂— group,

B is —CO₂G, where

G is a branched or unbranched aliphatic (C₁-C₁₆)-alkyl radical or a benzyl radical, R¹ and R², together with the pyridine carrying them, form an isoquinoline ring having an unsubstituted benzo-moiety, and R⁴ is methyl.

Compounds of the formula I are also preferred to the highest degree in which

Q is O, is O,

Y is CR³, m is 0,

A is a —CH₂— group,

B is —CO₂G, where

G is a branched or unbranched aliphatic (C₁-C₁₆)-alkyl radical or a benzyl radical, R¹ is hydrogen, R² and R³, together with the pyridine carrying them, form a quinoline ring having an unsubstituted benzo-moiety, and R⁴ is methyl.

The invention relates to the use of compounds of the formula I, and also the physiologically tolerated salts, for inhibiting collagen biosynthesis.

The invention relates to the use of Compounds of the formula I, and also the physiologically tolerated salts, for inhibiting prolyl-4-hydroxylase in vivo.

The invention also relates to the use of compounds of the formula I, and also the physiologically tolerated salts, for producing a pharmaceutical against fibrotic diseases.

The invention also relates to the use of compounds of the formula I, and also the physiologically tolerated salts, for producing a pharmaceutical against fibrotic diseases of the liver, the lung and the skin.

Finally, the invention relates to the compounds of the formula I for use as pharmaceuticals.

The invention relates, in particular, to the compounds of the formula I for use as fibrosuppressive agents.

The invention also relates to a process for preparing compounds of the formula I.

The compounds of the formula I, in which A is a substituted alkylene moiety, B is $CO_2G$, Y is $CR^3$ and m is 0 or 1, are prepared by i1.) reacting pyridine-2-carboxylic acids of the formula II ($R^{23}$ is H) with the amino esters of the formula III to form the amide esters of the formula I, or i2.) reacting pyridine-2-carboxylic esters of the formula II ($R^{23}$ is ($C_1$-$C_{16}$)-alkyl) to form the compounds of the formula I under the conditions of aminolysis; or ii) esterifying the compounds of the formula IV with the alcohol GOH; or iii) alkylating the compounds of the formula V with $R^4X$, and, where appropriate, iv) converting the compounds of the formula I, provided Q is O or NR', into their pyridine N-oxides (Formula I').

compounds of the formula II are prepared in situ and then reacted with the amide derivatives of the formula III.

An example of a suitable condensing agent is the combination of N,N'-dicyclohexylcarbodiimide/N-hydroxy-1H-benzotriazole and N-ethylmorpholine.

Suitable solvents are dichloromethane, tetrachloromethane, butyl acetate, ethyl acetate, toluene, tetrahydrofuran, dimethoxyethane, 1,4-dioxane, acetonitrile, N,N-dimethylformamide, N,N-dimethylacetamide, dimethylsulfoxide, nitromethane and/or pyridine.

The compounds of the formula I, in which $R^1$ and $R^3$ are hydrogen and $R^2$ is a carboxyl substituent, a carbamoyl substituent or an ester substituent, were prepared as outlined in schemes 1, 2 and 3.

Scheme 2 illustrates the preparation of the compounds of the formula II in which $R^2$ is a carboxylic acid substituent, or its derivative, and $R^1$ and $R^3$ are hydrogen.

The 3-substituted 5-carboxypyridine-2-carboxylic esters of the formula XI and their isomers of the formula XII are prepared from the pyridine-2,5-dicarboxylic diesters of the formula VII.

The oxidation of the pyridine-2,4-dicarboxylates of the formula VII is described in J. Chem. Soc. Perkin Trans. 2, 1978, 34–38 and in J. Org. Chem. 25 (1960) 565 to 568 (M. L. Peterson).

The halogenation (chlorination) of the pyridine N-oxides of the formula VIII with thionyl chloride and the reaction of the 3-chloropyridine-2,5-dicarboxylic diester (Formula IX) with alcoholates (Q is O or S) can be carried out in analogy with the process described in the patent specification CH 658 651 (LONZA), where M is a singly charged or doubly charged metal ion, preferably from the first or second main group of the periodic system.

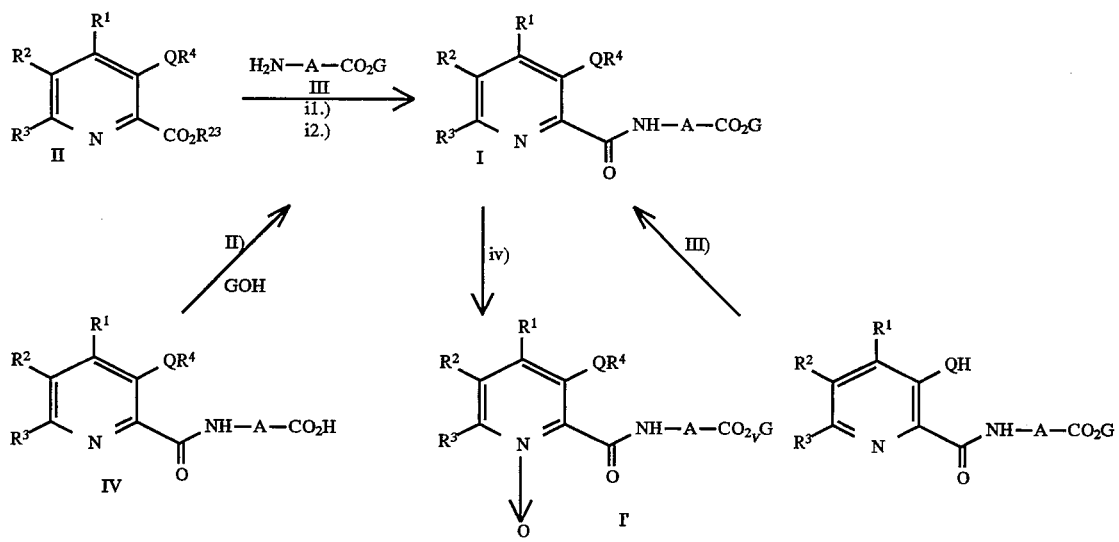

Scheme 1

$R^{23}$ is H or ($C_1$-$C_{16}$)-alkyl,

X is a leaving group, in particular: halogen, $OSO_2Me$ or $OSO_2phenyl$, inter alia.

The methods of carboxyl activation and the condensation reactions known from peptide chemistry are suitable processes for the amide formation (reaction i1).

The substances which are known to the person skilled in the art, such as thionyl chloride, oxalyl chloride, pivaloyl chloride, chloroformate derivatives, or N,N'-carbonyldiimidazole, can be used as reagents for the carboxylic acid activation. The activated derivatives of the In analogy with the known literature (CA: vol. 68, 1968, 68 840 h), the monoesters of the formula XII are prepared, under hydrolysis conditions, from the substituted pyridine-2,5-dicarboxylic diesters of the formula Xb.

Selective hydrolysis using Cu(II) salts, J. Delarge in Pharmaceutica Acta Helvetiae 44, 637–643, 1969, represents another process for preparing the compounds of the formula XII from the diesters of the formula Xb.

The compounds of the formula XII thus obtained are reacted with the amino esters of the formula III to form the compounds of the formula IV (Scheme 2).

The pyridine-2-carboxylic acid ester-5-carboxylates of the formula XI can be prepared, under esterification conditions, from substituted pyridine-2,5-dicarboxylic acids of the formula Xa (see CA: vol. 68, 1968, 68840 h). Suitable conditions are, for example, esterification with methanol in the presence of sulfuric acid, it being necessary to choose the reaction time so that complete esterification to form the diester product only takes place to a secondary extent, or so that the diester products can be separated off as by-products.

The compounds of the formula XI are converted with amines or alcohols into the 5-carboxylic acid derivatives of the formula XIV (Scheme 3).

These are then hydrolysed to form the compounds of the formula II ($R^{23}$ is H), which compounds are subsequently reacted in analogy with Scheme 1.

The 2-hydroxymethylpyridines of the formula VIa, which are disclosed in EP-A-0 304 732, EP-A-0 321 385 and EP-A-0 208 452, can be used as intermediates for preparing derivatives ($R^1$) which are substituted in the 4 position.

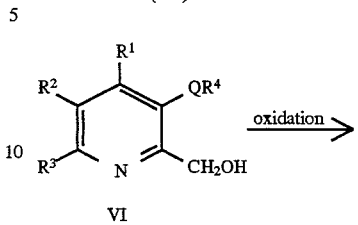

VI

Scheme 2

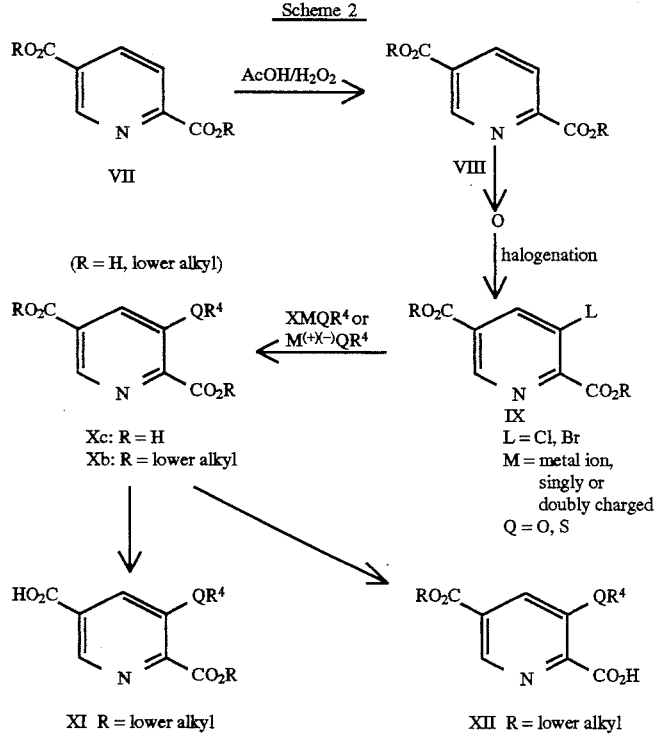

Scheme 3

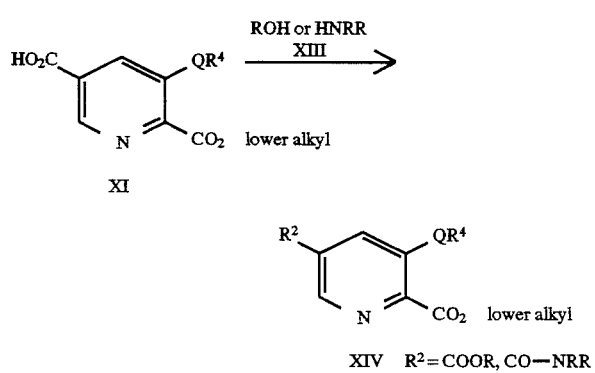

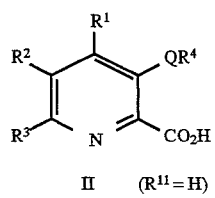

II    ($R^{11}$ = H)

VIa/IIa: $QR^4$ = OMe (Me = methyl)
VIb/IIb: $QR^4$ = OBn (Bn = benzyl)

The 3—O-benzyl derivatives of the formula VIb were also obtained in an analogous manner, as described in these documents.

The compounds of the formulae VIa and VIb were reacted with an oxidizing agent, preferably with $KMnO_4$ in aqueous alkaline medium, to form the pyridine-2-carboxylic acid derivatives of the formula II.

The preparation of substituted pyridine-2-carboxylic acids is, for example, disclosed in DE-A-353 046, and for 3-(3-chlorophenoxy)pyridine-2-carboxylic acid and 3-(3-methylphenoxy)pyridine-2-carboxylic acid in J. Med. Chem. 1975, 18, pp. 1–8, Villani et al.; for 3,5-diethoxypyridine- 2-carboxylic acid in J. Med. Chem. 1974, 17, pp. 172–181, French et al.; and for 3-methylthiopyridine-1-carboxylic acid and 3-benzylthiopyridine-2-carboxylic acid in J. Med. Chem. 1974, 17, pp. 1065–1071, Blank et al.; and for 3-methoxypyridine-2,5-dicarboxylic acid in CH-PS 658 651.

The novel compounds of the formula I possess valuable pharmacological properties and exhibit, in particular, antifibrotic activity.

The antifibrotic effect can be determined using the model of carbon tetrachloride-induced hepatic fibrosis. For this, rats are treated twice a week with $CCl_4$ (1 ml/kg)—dissolved in olive oil. The substance under test is administered daily, where appropriate even twice a day, per os, or intraperitoneally—dissolved in a suitable tolerated solvent. The extent of the hepatic fibrosis is determined by histology, and the proportion of collagen in the liver is analyzed by means of determining hydroxyproline—as described in Kivirikko et al. (Anal. Biochem. 19, 249 f. 1967)). The fibrogenic activity can be measured by the radioimmunological determination of collagen fragments and procollagen peptides in the serum. In this model, the novel compounds are active at a concentration of from 1 to 100 mg/kg.

The fibrogenic activity can be measured by radioimmunological determination of the N-terminal propeptide of collagen type III or of the N-terminal or C-terminal crosslinking domain of collagen type IV (7s collagen or type IV collagen $NC_1$) in the serum.

For this purpose, measurements were made of the concentrations of hydroxyproline, procollagen III peptide, 7s collagen and type IV collagen NC in the liver of a) untreated rats (control)
b) rats which were administered carbon tetrachloride ($CCl_4$ control)
c) rats which were first administered $CCl_4$ and then a novel compound (this test method is described by Rouiller, C., Experimental toxic injury of the liver; in The Liver, C. Rouiller, vol. 2, 5. 335 to 476, New York, Academic Press, 1964).

The novel compounds can also be demonstrated to be active in the following systems.

Inhibition of hepatic prolyl-4-hydroxylase in vivo:

This model is used to demonstrate the acute inhibition of prolyl-4-hydroxylase in vivo. For this, rats of both sexes (healthy or with induced hepatic fibrosis) are administered (intraperitoneally, intravenously or per os) the substance under test or the corresponding vehicle and, after this, are given $^{14}$C-L-proline (250 μCi/kg of body weight), which is administered intraperitoneally. There then follows a second intraperitoneal administration of $^{14}$C-L-proline (250 μCi/kg of body weight). Finally, the animals are exsanguinated under pentobarbital anesthesia and the livers removed. The hepatic collagen was purified by digestion with pepsin and fractional ammonium sulfate precipitation in conformity with published protocols (Ref. 1 and 2). The purified liver collagen was hydrolyzed and the content of $^{14}$C-hydroxyproline and $^{14}$C-proline was determined by means of amino acid analysis using ion exchange chromatography. Inhibition of prolyl-4-hydroxylase is shown by a decrease in the quotient $^{14}$C-hydroxyproline/[$^{14}$C-hydroxyproline+$^{14}$C-proline]. 2,2'-Dipyridyl is used as the reference substance.

(1: Chojkier, M. 1986, Hepatocyte collagen production in vivo in normal rats, J. Clin. Invest. 78: 333–339 and 2: Ogata I., et al. 1991, Minor contribution of hepatocytes to collagen production in normal and early fibrotic livers, Hepatology 14: 361–367).

Inhibition of prolyl-4-hydroxylase in cell cultures: The following cell types are used for testing inhibitors of prolyl-4-hydroxylase in cell cultures:

Normal human skin fibroblasts, (NHDF), rat liver epithelial cells (ref. 1) and primary fat storing cells from rat liver (ref. 2). For this, the cells are cultivated in the presence of inhibitors. At the same time, the collagen which is newly synthesized during this period is metabolically labelled with 4-$^3$H-L-proline and $^{14}$C-proline. The influence of the test substances on the degree of hydroxylation of the collagen is then determined in accordance with the method of Chojkier et al (ref. 3). 2,2'-Dipyridyl is employed as the reference substance. (1.: Schrode, W., Mecke, D., Gebhard, R. 1990, Induction of glutamine synthetase in periportal hepatocytes by co-cultivation with a liver epithelial cell line, Eur. J. Cell. Biol. 53: 35–41; 2. Blomhoff, R., Berg T. 1990, Isolation and cultivation of rat liver stellate cells, Methods Enzymol. 190: 59–71; and 3.: Chojkier, M. Peterkofsky, B. Bateman, J. 1980, A new method for determining the extent of proline hydroxylation by measuring changes in the ration of [4-$^3$H]:[$^{14}$C]proline in collagenase digests, Anal. Biochem. 108: 385–393).

The compounds of the formula I may be used as medicaments in the form of pharmaceutical preparations, which contain the compounds, where appropriate together with tolerated pharmaceutical excipients. The compounds can be used as medicines, for example in the form of pharmaceutical preparations which contain these compounds in a mixture together with a pharmaceutical, organic or inorganic excipient which is suitable for enteral, percutaneous or parenteral administration, such as, for example, water, gum arabic, gelatin, lactose, starch, magnesium stearate, talc, vegetable oils, polyalkylene glycols, vaseline, etc.

For this purpose, they can be administered orally in doses of from 0.1 to 23 mg/kg/day, preferably of from 1 to 5 mg/kg/day, or parenterally in doses of from 0.01 to 5 mg/kg/day, preferably of from 0.01 to 2.5 mg/kg/day, in particular of from 0.5 to 1.0 mg/kg/day. The dosage can also be increased in severe cases. In many cases, however, smaller doses are also Sufficient. These data refer to an adult of about 75 kg in weight.

The novel compounds of the formula I are designated substituted heterocyclic carboxylic acid (amino acid ester) amides, preferably pyridine-2-carboxylic acid (glycyl ester) amides, in the examples described below. This mode of designation is understood to mean, for example, substituted pyridine-2-carboxylic acid N-((alkoxycarbonyl)methyl) amides.

Another option is to classify them as substituted N-(pyridyl-2-carbonyl)glycines.

EXAMPLE 1

3-Methoxy-4-(2,2,2-trifluoroethyloxy)pyridine-2-carboxylic acid (glycyl ethyl ester) amide a) 2-Methyl-3-methoxy-4-chloropyridine N-oxide 11.2 g (80.5 mmol) of 3-methoxy-2-methyl-4(1H)-pyridone were heated under reflux for 10 hours in 100 ml of phosphorus oxychloride. Subsequently, the mixture was concentrated and 30 ml of toluene were added to each 2 ml volume; concentration then took place once again and the residue was taken up in 150 ml of water, with the pH of the mixture then being adjusted to 11 with $K_2CO_3$; this mixture was then extracted with dichloromethane and the organic phase was washed with water, dried and freed from solvent.

8 g of the product were obtained, under standard conditions, from the pale brown oil (9 g) using m-chloroperbenzoic acid in dichloromethane, m.p. 88°–89° C. (from petroleum ether).

b) 2-Methyl-3-methoxy-4-(2,2,2-trifluoroethoxy)pyridine N-oxide 6.7 g of potassium tert-butoxide were added in portions, at −20° C., while stirring and under a nitrogen atmosphere, 5 to 20 ml of trifluoroethanol. After the mixture had been warmed to 0° C., 5.2 g (30 mmol) of 2-methyl-3-methoxy-4-chloropyridine N-oxide were added in portions. The mixture was heated under reflux for 3 hours, and then left to cool down to room temperature; a further 3.45 g of potassium tert-butoxide were then added and the mixture was heated under reflux for 2 hours. After it had cooled down, 40 ml of water were added to the reaction mixture, which was then extracted with dichloromethane; the extract was then dried over $MgSO_4$ and freed from the solvent in vacuo. The resulting oily product was subjected to further reaction.

c) 3-Methoxy-4-(2,2,2-trifluoroethoxy)-2-hydroxymethylpyridine 8 g (33.8 mmol) of the above compound were dissolved in 16 ml of glacial acetic acid, and 24 ml of acetic anhydride were added, at 80° C. and while stirring, to this mixture. The reaction mixture was heated at 110° C. for 2 hours and then cooled down to 80° C.; 40 ml of methanol were then added to it dropwise. Subsequently, the mixture was concentrated in vacuo, and the oily residue added to 75 ml of 2N methanolic NaOH, with this mixture being stirred for 30 minutes. Following treatment with active charcoal, and filtration, the mixture was concentrated in vacuo and 50 ml of water were added to the residue after which extraction took place with dichloromethane; the extract was dried ($MgSO_4$) and concentrated, and the residue was treated with diisopropyl ether. 3.9 g of the product were obtained in the form of colorless crystals, m.p. 107°–108° C.

d) 3-Methoxy-4-(2,2,2-trifluoroethyloxy)pyridine-2-carboxylic acid 0.8 g (3.3 mmol) of the above alcohol was dissolved in a solution composed of 0.3 g of potassium hydroxide and 5 25 ml of water, and 1.6 g of potassium permanganate were added in portions at 100° C. and while stirring. After decolorization, the manganese dioxide which had formed was filtered off with suction from the hot mixture and washed twice with hot water; the filtrate was concentrated in vacuo to ⅓ of the volume, adjusted to pH 1 with conc. aqueous hydrochloric acid, and concentrated in vacuo; the residue was treated with anhydrous ethanol and the undissolved material was filtered off. 0.73 g of product, m.p. 157°, was obtained from the filtrate.

e) To prepare the title compound, 0.58 g (2.3 mmol) of the above carboxylic acid was suspended in 100 ml of anhydrous tetrahydrofuran, after which 322 mg (2.3 mmol) of glycine ethyl ester hydrochloride, 0.64ml (5 mmol) of N-ethylmorpholine, 350 mg (2.6 mmol) of 1-hydroxy-1H-benzotriazole and 537 mg (2.6mmol) of N,N'-dicyclohexylcarbodiimide were added, at 20° C. and while stirring, and the mixture was then stirred at 20° C. for 48 h. Undissolved material was then filtered off and the filtrate was concentrated in vacuo; the residue was taken up in ethyl acetate and undissolved material was filtered off; the filtrate was stirred together with 100 ml of a saturated, aqueous solution of Na bicarbonate, and the organic phase was dried and concentrated in vacuo; the residue was crystallized using diisopropyl ether. 0.45 g was obtained of the colorless crystalline product, m.p. 80°–82° C.

EXAMPLE 2

4-Chloro-3-methoxypyridine-2-carboxylic acid (glycyl ethyl ester) amide a) 4-Chloro-2-hydroxymethyl-3-methoxypyridine 30 g (173mmol) of 4-chloro-3-methoxy-2-methylpyridine N-oxide (cf. Example 1a) were dissolved in 100 ml of glacial acetic acid, after which 150 ml of acetic anhydride were added dropwise, at 80° C. and while stirring, and the mixture was then stirred at 110° C. for 2 h. The mixture was then cooled down to 80° C. and 200 ml of methanol were added dropwise; the mixture was then heated to boiling for 15 min. and, after having been cooled down, concentrated in vacuo; the residue was taken up in methanol and this mixture was allowed to flow into 300 ml of 1.5N methanolic sodium hydroxide solution, with this mixture then being stirred at 20° C. for 30 min. and concentrated in vacuo; the residue was taken up in water, and this mixture extracted three times with dichloromethane, with the organic phase being dried and concentrated; the residue was crystallized using petroleum ether. 23 g of product were obtained, m.p. 64°–66° C.

b) 4-Chloro-3-methoxypyridine-2-carboxylic acid 8.65 g (50 mmol) of the above alcohol were dissolved in a mixture composed of 0.8 g of potassium hydroxide and 60 ml of water, after which potassium permanganate was added in portions, at 60° C. and while stirring, until no more discoloration could be seen (12 g, 75 mmol). After 1 h at 60° C., the manganese dioxide was filtered off with suction and then washed with hot water; the filtrate was concentrated in vacuo to 200 ml and adjusted, while cooling, to pH 1 with aqueous conc. HCl. After grinding, the product crystallizes out in association with cooling. Additional product can be obtained from the mother liquor by treatment with petroleum ether. Total quantity 4.2 g, m.p. 116°–117° C. (with gas evolution).

c) To prepare the title compound, 4.7 g (25 mmol) of the above carboxylic acid were suspended in 200 ml of anhydrous dichloromethane, and after that 3.5 g (25 mmol) of glycine ethyl ester hydrochloride, 6.4 ml (50 mmol) of N-ethylmorpholine, 3.8 g (28 mmol) of 1-hydroxy-(1H)-benzotriazole and 5.15 g (25 mmol) of N,N'-dicyclohexyl carbodiimide were added sequentially, at 20° C. and while stirring, and the mixture was then stirred at 20° C. for 20 h. Undissolved material was then filtered off and the organic phase was shaken with a saturated, aqueous solution of sodium carbonate, dried and concentrated in vacuo; the residue (6 g of oil) was chromatographed on silica gel using ethyl acetate and 5.4 g of oily product were obtained.

EXAMPLE 3

4-Butyloxy-3-methoxypyridine-2-carboxylic acid (glycyl ethyl ester) amide

EXAMPLE 4

3,4-Dimethoxypyridine-2-carboxylic acid (glycyl ethyl ester) amide

EXAMPLE 5

3-Ethyloxy-4-(3-methoxybenzyloxy)pyridine-2-carboxylic acid (glycyl ethyl ester) amide

EXAMPLE 6

4-Hexyloxy-3-methoxypyridine-2-carboxylic acid (glycyl ethyl ester) amide

EXAMPLE 7

3-Methoxy-4-(3-methylbutyloxy)pyridine-2-carboxylic acid (glycyl ethyl ester) amide

EXAMPLE 8

4-(4-Fluorobenzyloxy)-3-methoxypyridine-2-carboxylic acid (glycyl ethyl ester) amide

EXAMPLE 9

3-Methoxy-4-(4-trifluoromethylbenzyloxy)pyridine-2-carboxylic acid (glycyl ethyl ester) amide

EXAMPLE 10

3-Methoxy-4-(2,2,3,3,3-pentafluoropropyloxy)pyridine-2-carboxylic acid (glycol ethyl ester) amide

EXAMPLE 11

4-(2,2,3,3,4,4,4-Heptafluorobutyloxy)-3-methoxypyridine-2-carboxylic acid (glycyl ethyl ester) amide

EXAMPLE 12

4-(3-Methoxybenzyloxy)-3-methoxypyridine-2-carboxylic acid (glycyl ethyl ester) amide

EXAMPLE 13

3-Ethyloxy-4-(2,2,2-trifluoroethyloxy)pyridine-2-carboxylic acid (glycyl ethyl ester) amide

EXAMPLE 14

4-Butyloxy-3-ethyloxypyridine-2-carboxylic acid (glycyl ethyl ester) amide

EXAMPLE 15

3-Methoxy-4-((2-phenoxyethyl)oxy)pyridine-2-carboxylic acid (glycyl ethyl ester) amide

EXAMPLE 16

3-Ethyloxy-4-benzyloxypyridine-2-carboxylic acid (glycyl ethyl ester) amide

EXAMPLE 17

3,6-Dimethoxypyridine-2-carboxylic acid (glycyl ethyl ester) amide a) 3,6-Dimethoxy-2-methylpyridine N-oxide 1.15 g (50 mmol) of sodium were dissolved in 100 ml of anhydrous methanol, and after that 7.4 g (40 mmol) of 3-methoxy-2-methyl-6-nitropyridine N-oxide were added at 20° C. and while stirring. The mixture was then heated to reflux for 3 h and, after having been cooled down, concentrated in vacuo; the residue was taken up in water and this mixture was extracted with dichloromethane; the organic phase was dried and concentrated and the residue was crystallized using diisopropyl ether. 7 g of product were obtained, m.p. 63°–65° C.

b) 3,6-Dimethoxy-2-hydroxymethylpyridine 7 g (41.4 mmol) of the above compound were reacted with glacial acetic acid/acetic anhydride in analogy with Example 1c) and the resulting acetate was hydrolyzed using 1.5N methanolic sodium hydroxide solution. 5.6 g were obtained of oily product which was subjected to further reaction under c).

c) 3,6-Dimethoxypyridine-2-carboxylic acid 5.6 g (33 mmol) of the above compound and 2.4 g of potassium hydroxide were dissolved in 150 ml of water, and after that 15 g (100 mmol) of potassium permanganate were added in portions at 60° C. and while stirring. The manganese dioxide which had formed was then filtered off with suction and washed twice with hot water; the combined water phase was concentrated to 100 ml, adjusted to pH 1 with conc. aqueous hydrochloric acid while being cooled with ice, and concentrated in vacuo; the residue was treated with ethyl acetate and ethanol, and undissolved material was filtered off from this mixture, with the filtrate being concentrated in vacuo. The residue was crystallized using diethyl ether. 4 g of product were obtained, m.p. 131°–132° C. (with gas evolution).

d) To prepare the title compound, 2.2 g (12 mmol) of the above carboxylic acid were suspended in 300 ml of anhydrous dichloromethane, and after that 1.68 g (12 mmol) of glycine ethyl ester hydrochloride, 3.25 ml (25 mmol) of N-ethylmorpholine, 1.62 g (12 mmol) of 1-hydroxy-1H-benzotriazole and 5.2 g (12 mmol) of N-cyclohexyl-N'-(2-morpholinoethyl)carbodiimide methyl-p-toluenesulfonate were added, while stirring, and the mixture was then stirred at 20° C. for 20 h. The small amount of undissolved material was then filtered off and the filtrate was shaken once with water and then with a saturated, aqueous soluton of Na bicarbonate; the organic phase was dried and concentrated in vacuo and the residue was crystallized using diisopropyl ether. 2 g of product were obtained, m.p. 93°–95° C.

EXAMPLE 18

3,5-Diethoxypyridine-2-carboxylic acid (glycyl ethyl ester) amide

EXAMPLE 19

3-Methoxy-6-(3-methylbutyloxy)pyridine-2-carboxylic acid (glycyl ethyl ester) amide

EXAMPLE 20

3-Benzyloxy-4-(3-ethyloxypropyloxy)pyridine-2-carboxylic acid (glycyl ethyl ester) amide

EXAMPLE 21

3-Benzyloxy-4-hexyloxypyridine-2-carboxylic acid (glycyl ethyl ester) amide

EXAMPLE 22

6-(2-Butoxyethyloxy)-3-methoxypyridine-2-carboxylic acid (glycyl ethyl ester) amide

EXAMPLE 23

6-Butyloxy-3-methoxypyridine-2-carboxylic acid (glycyl ethyl ester) snide

EXAMPLE 24

3-Ethyloxy-6-methylpyridine-2-carboxylic (glycyl ethyl ester) amide

EXAMPLE 25

6-Benzyloxy-3-methoxypyridine-2-carboxylic acid (glycyl ethyl ester) amide

EXAMPLE 26

3-Benzyloxypyridine-2-carboxylic acid (glycyl ethyl ester) amide

EXAMPLE 27

3-Methoxypyridine-2-carboxylic acid (glycyl ethyl ester) amide hydrochloride

M.p. 141°–142° C. (with gas evolution, from diethyl ether)

This ethyl ester was obtained by catalytic hydrogenation of 4-chloro-3-methoxypyridine-2-carboxylic acid (glycyl ethyl ester) amide (see Example 2c), which was obtained from 4-chloro-3-methoxypyridine-2-carboxylic acid (m.p. 119°–120° C., from 4-chloro-3-methoxy-2-methypyridine N-oxide by reaction with acetic anhydride/glacial acetic acid and subsequent oxidation of the 2-hydroxymethylpyridine derivative) (see Example 2a and b) and glycine ethyl ester hydrochloride.

EXAMPLE 28

3-Ethoxypyridine-2-carboxylic acid (glycyl ethyl ester) amide

EXAMPLE 29

3-Propyloxypyridine-2-carboxylic acid (glycyl ethyl ester) amide

EXAMPLE 30

3-Butyloxypyridine-2-carboxylic acid (glycyl ethyl ester) amide a) 3-n-Butyloxypyridine-2-carboxylic acid 6 g (150-mmol) of NaH (60%, in mineral oil) were added in portions, at 20° C. and while stirring, to 9.8 g (70 mmol) of 3-hydroxypyridine-2-carboxylic acid in 5 150 ml of N,N-dimethylacetamide. After 30 min., 15 ml (140 mmol) of butyl bromide were added dropwise and the mixture was heated at between 95° C. and 125° C. for 2.5 h. After having been cooled down, the mixture was concentrated in vacuo, treated with an aqueous solution of Na bicarbonate and extracted with dichloromethane; after drying, the residue was purified by chromatography on silica gel using ethyl acetate. The 13 g of oily product thus obtained were introduced into 250 ml of 1.5N methanolic sodium hydroxide solution, and the mixture was then stirred at 20° C. for 30 min and concentrated in vacuo; the residue was taken up in 200 ml of water and this mixture was extracted with dichloromethane and the aqueous phase was adjusted to pH 1 with conc. aqueous hydrochloric acid; concentration took place in vacuo and the residue was treated with ethyl acetate and then with anhydrous ethanol. The resulting solutions were concentrated and the residue was crystallized using acetone. 9.3 g were obtained of product (m.p. 93°–95° C.) which, according to $^1$H NMR, still contained approximately 20% of 3-hydroxypyridine-2-carboxylic acid.

b) 2.8 g (20 mmol) of glycine ethyl ester hydrochloride, 5.2 ml (40 mmol) of N-ethylmorpholine, 2.7 g (20 mmol) of 1-hydroxy-1H-benzotriazole and 3.0 ml (20 mmol) of N,N'-diisopropylcarbodiimide were added, at 20° C. and while stirring, to 4 g (20 mmol) of the above product in 200 ml of anhydrous tetrahydrofuran and 100 ml of anhydrous acetonitrile, and the mixture was then stirred at 20° C. for 20 h. After working up (treatment with Na bicarbonate solution, removal of precipitated diisopropylurea), 3.5 g of oily product, which still contained N,N'-diisopropylurea, were obtained following chromatography on silica gel (ethyl acetate/n-heptane 1:1; then pure ethylacetate).

EXAMPLE 31

3-(4-Chlorobenzyloxy)pyridine-2-carboxylic acid (glycyl ethyl ester) amide a) 4-Chlorobenzyl 3-(4-chlorobenzyloxy)pyridine-2-carboxylate 8.4 g (60 mmol) of 3-hydroxypyridine-2-carboxylic acid were alkylated (3 h, 110° C.) with 5.2 g (approximately 130 mmol, 60%) of sodium hydride and 19.3 g (120 mmol) of 4-chlorobenzyl chloride in N,N-dimethylacetamide in analogy with Example 30a). After concentration in vacuo and extraction with Na bicarbonate solution, the residue was purified on silica gel using heptane/ethyl acetate (1:1), and 14.8 g of the product were crystallized from appropriate fractions using diisopropyl ether, m.p. 92°–94° C.

b) 3-(4-Chlorobenzyloxy)pyridine-2-carboxylic acid 9.7 g (25 mmol) of the above ester were hydrolyzed with 200 ml of 1.5N methanolic sodium hydroxide solution (24 h, 20° C.). After working up (concentration, taking up of the residue in water, extraction with dichloromethane and acidification), 6.5 g of product were obtained, m.p. 144° C. (from water, decomposition).

c) To prepare the title compound, 3.2 g (12 mmol) of the above pyridine-2-carboxylic acid were reacted, in analogy with example 17d), with 1.7 g (12 mmol) of glycine ethyl ester hydrochloride, 1.62 g (12 mmol) of 1-hydroxy-(1H)-benzotriazole, 3.3 ml (25 mmol) of N-ethylmorpholine and 5.2 g (12 mmol) of N-cyclohexyl-N'-(2-morpholinoethyl) carbodiimide methyl-p-toluenesulfonate. After working up, 3.0 g of the product were crystallized using diisopropyl ether, m.p. 106°–108° C.

EXAMPLE 32

3-(3-Methoxybenzyloxy)pyridine-2-carboxylic acid (glycyl ethyl ester) amide a) 3-Methoxybenzyl 3-(3-methoxybenzyloxy)pyridine-2-carboxylate In analogy with Example 38a), 10 g of the product were obtained, as a colorless oil which was subjected to further reaction, from 8.4 g (60 mmol) of 3-hydroxypyridine-2-carboxylic acid and 3-methoxybenzyl chloride following chromatography on silica gel.

b) 3-(3-Methoxybenzyloxy)pyridine-2-carboxylic acid 10 g of the above ester were hydrolyzed in 300 ml of 1.5N methanolic sodium hydroxide Solution. 7.5 g of product were obtained, m.p. 147° C. (decomposition, from aqueous hydrochloric acid)

c) To prepare the title compound, 3.2 g (12 mmol) of the above carboxylic acid were reacted in analogy with Example 31c). 3.6 g of oily crude product were isolated which, according to the $^1$H NMR spectrum, still contained N-ethylmorpholine. The pure substance, m.p. 135°–137° C., was obtained from this crude product (from diisopropyl ether/ethyl acetate).

EXAMPLE 33

3-(2-Phenylethyloxy)pyridine-2-carboxylic acid (glycyl ethyl ester) amide a) 3-((2-Phenylethyloxy)pyridine-2-carboxylic acid In analogy with Example 30a), 8.4 g (60 mmol) of 3-hydroxypyridine-2-carboxylic acid were alkylated with NaH/2-phenylethyl bromide in N,N-dimethylacetamide. The 10 g of oily product obtained after purification by column chromatography were hydrolyzed with methanolic sodium hydroxide solution in Analogy with Example 30a). 3 g of product were obtained (m.p. 145° C. (with foaming, from acetone)) which, according to the 1b NMR spectrum, contains approximately 25% of 3-hydroxypicolinic acid.

b) To prepare the title compound, 2.9 g of the above compound were reacted, in analogy with Example 30b), with glycine ethyl ester hydrochloride, N-ethylmorpholine, 1-hydroxy-1H-benzotriazole and N,N-dicyclohexylcarbodiimide. After working up, the crude product was chromatographed on silica gel using ethyl acetate. 3-Hydroxypyridine-2-carboxylic acid (glycyl ethyl ester) amide was initially eluted as a by-product and crystallized from appropriate fractions using petroleum ether; 1.1 g (m.p. 86°–88° C., strong fluorescence in UV light). The product was then crystallized from appropriate fractions using diisopropyl ether, and 1.7 g of the product were obtained, m.p. 73°–75° C.

EXAMPLE 34

3-(4-Trifluoromethylbenzyloxy)pyridine-2-carboxylic acid (glycyl ethyl ester) amide M.p. 107°–109° C.

EXAMPLE 35

3-(4-(2-Propyl)benzyloxy)pyridine-2-carboxylic acid (glycyl ethyl ester) amide, colorless oil

EXAMPLE 36

3-(4-Fluorobenzyloxy)pyridine-2-carboxylic acid (glycyl ethyl ester) amide

M.p.: 97°–99° C. (from diisopropyl ether)

EXAMPLE 37

3-(4-(2-(4-Methoxyphenyl)ethylamino)carbonyl) benzyloxy)pyridine-2-carboxylic acid (glycyl ethyl ester) amide M.p. 141°–143° C. (from diethyl ether/ethyl acetate (9:1)).

Example Nos 38–64 below were prepared in an analogous manner.

EXAMPLE 38

3-(2,4-Dichlorobenzyloxy)pyridine-2-carboxylic acid (glycyl ethyl ester) amide

EXAMPLE 39

3-(3-Fluorobenzyloxy)pyridine-2-carboxylic acid (glycyl ethyl ester) amide

EXAMPLE 40

3-(3–Chlorobenzyloxy)pyridine-2-carboxylic acid (glycyl ethyl ester) amide

EXAMPLE 41

3-(3,4-Dichlorobenzyloxy)pyridine-2-carboxylic acid (glycyl ethyl ester) amide

EXAMPLE 42

3-(3-Trifluoromethylbenzyloxy)pyridine-2-carboxylic acid (glycyl ethyl ester) amide

EXAMPLE 43

3-(4-Trifluoromethoxybenzyloxy)pyridine-2-carboxylic acid (glycyl ethyl ester) amide

EXAMPLE 44

3-(3-Ethoxybenzyloxy)pyridine-2-carboxylic acid (glycyl ethyl ester) amide

EXAMPLE 45

3-(4-Cyanobenzyloxy)pyridine-2-carboxylic acid (glycyl ethyl ester) amide

EXAMPLE 46

3-((2-Pyridylmethyl)oxy)pyridine-2-carboxylic acid (glycyl ethyl ester) amide hydrochloride

EXAMPLE 47

3-((3-Pyridylmethyl)oxy)pyridine-2-carboxylic acid (glycyl ethyl ester) amide hydrochloride

EXAMPLE 48

3-((4-Pyridylmethyl)oxy)pyridine-2-carboxylic acid (glycyl ethyl ester) amide hydrochloride

EXAMPLE 49

3-(2-Thienylmethyl)oxy)pyridine-2-carboxylic acid (glycyl ethyl ester) amide

EXAMPLE 50

3-(3,5-Dimethoxybenzyloxy)pyridine-2-carboxylic acid (glycyl ethyl ester)

EXAMPLE 51

3-Cyclohexyloxypyridine-2-carboxylic acid (glycol ethyl ester) amide

EXAMPLE 52

3-(3-Phenylpropyloxy)pyridine-2-carboxylic acid (glycyl ethyl ester) amide

EXAMPLE 53

3-(4-Phenylbutyloxy)pyridine-2-carboxylic acid (glycyl ethyl ester) amide

EXAMPLE 54

3-(((4-Methoxy-2-pyridyl)methyl)oxy)pyridine-2-carboxylic acid (glycyl ethyl ester) amide

EXAMPLE 55

3-(((4-Ethoxy-2-pyridyl)methyl)oxy)pyridine-2-carboxylic acid (glycyl ethyl ester) amide

EXAMPLE 56

3-Methylthiopyridine-2-carboxylic acid (glycyl ethyl ester) amide

EXAMPLE 57

3-Benzylthiopyridine-2-carboxylic acid (glycyl ethyl ester) amide

EXAMPLE 58

3-(3–Chlorophenoxy)pyridine-2-carboxylic acid (glycyl ethyl ester) amide

EXAMPLE 59

3-(3-Methoxyphenoxy)pyridine-2-carboxylic acid (glycyl ethyl ester) amide

EXAMPLE 60

3-Phenoxypyridine-2-carboxylic acid (glycyl ethyl ester) amide

EXAMPLE 61

3-Butyloxypyridine-2-carboxylic acid (L-alanyl ethyl ester) amide

EXAMPLE 62

3-Butyloxypyridine-2-carboxylic acid (D-alanyl ethyl ester) amide

EXAMPLE 63

3-Benzyloxypyridine-2-carboxylic acid (β-alanyl ethyl ester) amide

EXAMPLE 64

3-(3-Methylbutyloxy)pyridine-2-carboxylic acid (L-leucyl ethyl ester) amide

EXAMPLE 65

4-Methoxyisoquinoline-3-carboxylic acid (glycyl methyl ester) amide a) Methyl 1,2-dihydro-4-hydroxy-1-oxoisoquinoline-3-carboxylate, was prepared as described (M. Suzuki et al., Synthesis 1978, 461).

b) Methyl 1,2-dihydro-4-methoxy-1-oxoisoquinoline-3-carboxylate, from a) using (trimethylsilyl)diazomethane in methanol/acetonitrile, m.p. 177° to 179° C. (ethyl acetate/heptane).

c) Methyl 1-chloro-4-methoxyisoquinoline-3-carboxylate, from b) using phosphorus oxychloride, m.p. 108° C. (ethyl acetate).

d) Methyl 4-methoxyisoquinoline-3-carboxylate, from c) using hydrogen/Pd/C, m.p. 129° C. (from methyl tert-butyl ether).

e) 4-Methoxyisoquinoline-3-carboxylic acid, by hydrolysis of d), m.p. 185° to 189° C. (from aqueous hydrochloric acid).

f) The title compound was obtained from the above compound and glycine methyl ester hydrochloride using DCC, HOBT, THF and NEM; oily substance. $^1$H NMR (CDCl$_3$): δ=4.33 (d, CH$_2$-glycine).

Examples 66 to 76 were obtained in an analogous manner from the corresponding isoquinoline-3-carboxylic acids or the 4,6,7,8-tetrahydro derivatives, respectively;

EXAMPLE 66

4-Ethoxyisoquinoline-3-carboxylic acid (glycyl ethyl ester) amide

EXAMPLE 67

4-Propyloxyquinoline-3-carboxylic acid (glycyl ethyl ester) amide

EXAMPLE 68

4-(3-Methylbutyloxy) isoquinoline-3-carboxylic acid (glycyl ethyl ester) amide

EXAMPLE 69

4-Methoxy-5,6,7,8-tetrahydroisoquinoline-3-carboxylic acid (glycyl ethyl ester) amide

EXAMPLE 70

4-(3-Methylbutyloxy)-5,6,7,8-tetrahydroisoquinoline-3-carboxylic acid (glycyl ethyl ester) amide

EXAMPLE 71

4-Ethoxy-5,6,7,8-tetrahydroisoquinoline-3-carboxylic acid (glycyl ethyl ester) amide

EXAMPLE 72

4-Benzyloxy-5,6,7,8-tetrahydroisoquinoline-3-carboxylic acid (glycyl ethyl ester) amide

EXAMPLE 73

4-Benzyloxyisoquinoline-3-carboxylic acid (glycyl ethyl ester) amide

EXAMPLE 74

4-(3-Methoxybenzyloxy)-5,6,7,8-tetrahydroisoquinoline-3-carboxylic acid (glycyl ethyl ester) amide

EXAMPLE 75

7-Bromo-4-methoxyisoquinoline-3-carboxylic acid (glycyl ethyl ester) amide

EXAMPLE 76

7-Methoxy-4-methoxyisoquinoline-3-carboxylic acid (glycyl ethyl ester) amide

EXAMPLE 77

3-Methoxy-6-((3-methylbutyloxy)methyl)pyridine-2-carboxylic acid (glycyl ethyl ester) amide

EXAMPLE 78

3-Methoxy-6-((cyclohexyloxy)methyl)pyridine-2-carboxylic acid (glycyl ethyl ester) amide

EXAMPLE 79

3-Methoxy-6-benzyloxymethylpyridine-2-carboxylic acid (glycyl ethyl ester) amide

EXAMPLE 80

5-Carboxy-3-methoxypyridine-2-carboxylic acid (glycyl ethyl ester) amide

EXAMPLE 81

5-Methoxycarbonyl-3-methoxypyridine-2-carboxylic acid (glycyl benzyl ester) amide a) 5-Methoxycarbonylpyridine-2-carboxylic acid 1-oxide 12 g (60 mmol) of dimethyl pyridine-2,5-dicarboxylate were suspended in 30 ml of glacial acetic acid, and after that 13 ml of hydrogen peroxide (35%) were added at and while stirring. The mixture was then heated to 100° C. (internal temperature), while stirring, with a clear solution being formed at 50° C. After the mixture had been stirred at 100° C. for 90 minutes, it was allowed to cool down to 20° C. and the crystalline precipitate was filtered off with suction and washed with water; after drying, 7.5 g of product were obtained, m.p. 160° C. (decomp.).

b) Dimethyl 3-chloropyridine-2,5-dicarboxylate 17 ml of thionyl chloride, 35 ml of anhydrous chloroform and 1.5 ml of N,N-dimethylformamide were heated to 60° C., while stirring, and 7.5 g of the above product were then added in portions at this temperature. The mixture was then stirred at 60° C. for a further 60 minutes, and, after cooling, the solvent and excess reagent were distilled off in vacuo; dichloromethane was added to the residue, and the N,N-dimethylformamide×HCl complex was filtered off with suction and washed with dichloromethane. Approximately 15 ml of triethylamine and 10 ml of methanol were added, while cooling, to the mother liquor and the mixture was stirred for 30 minutes. After concentrating by evaporation in vacuo, the residue was dissolved in 50 ml of water and this mixture was then extracted 3 x with dichloromethane; the organic phase was dried and concentrated, and the residue was chromatographed on silica gel using n-heptane and n-heptane:ethyl acetate (3:1). 5.3 g of product were crystallized, using petroleum ether, from appropriate fractions, m.p. 36 to 38° C.

c) 3-Methoxypyridine-2,5-dicarboxylic acid 53 g (0.231 mol) of the above diester were dissolved in 500 ml of methanol, and after that 150 ml (0.81 mol) of sodium methoxide solution (30% in methanol) were added, at 20° C. and while stirring, whereupon the temperature rose to 30° C. The mixture was heated under reflux for 4.5 hours, 300 ml of water were added at 20° C., and the mixture was then stirred at 35° for 30 minutes. The excess methanol was distilled off in vacuo and the aqueous phase was adjusted to pH 2, while cooling, with half-concentrated aqueous hydrochloric acid; the colorless crystalline product was filtered off with suction and dried. 49 g were obtained, m.p. 185° C. (gas evolution); 255° C. (decomp.).

d) Dimethyl 3-methoxypyridine-2,5-dicarboxylate, (cf. Example 90a)

e) 5-Methoxycarbonyl-3-methoxypyridine-2-carboxylic acid

The compound was obtained, as a mixture with the isomeric monomethyl ester (cf. Example 90a)), from 3.4 g (15 mmol) of the above diester by hydrolysis with dilute methanolic sodium hydroxide solution (0.54 g of NaOH (13.5 mmol)). 1.8 g of monoester mixture, m.p. 152° C., was obtained in addition to 0.8 g of unreacted diester.

f) 1.8 g of the above mixture were condensed, in analogy with Example 90b), with 2.9 g (8.6 mmol) of glycine benzyl ester tosylate in the presence of N-ethylmorpholine, 1-hydroxy-1H-benzotriazole and CMC. After working up, 2.3 g of oily mixture were chromatographed on silica gel using dichloromethane (with the addition of up to 2% methanol). 0.82 g of product was obtained, m.p. 108° C. 0.6 g of the oily isomer was also isolated.

Exmaple 82

5-(3-Pentyloxy)carbonyl-3-methoxypyridine-2-carboxylic acid (glycyl ethyl ester) amide

EXAMPLE 83

5-Cyclohexyloxycarbonyl-3-methoxypyridine-2-carboxylic acid (glycyl ethyl ester) amide

EXAMPLE 84

5-(n-Butylaminocarbonyl)-3-methoxypyridine-2-carboxylic acid (glycyl ethyl ester) amide

EXAMPLE 85

5-(2-Methyl-2-butylaminocarbonyl)-3-methoxypyridine-2-carboxylic acid (glycyl ethyl ester) amide

EXAMPLE 86

5-(Cyclohexylaminocarbonyl)-3-methoxypyridine-2-carboxylic acid (glycyl ethyl ester) amide a) 5-(Cyclohexylaminocarbonyl)-3-methoxypyridine-2-carboxylic acid The product was obtained, in analogy with Example 90b), from 5-carboxy-3-methoxypyridine-2-carboxylic acid and cyclohexylamine, m.p. 155° C. (sintering at 80° C., from aqueous hydrochloric acid).

b) The title compound was obtained, in analogy with Example 90c), from the above compound, m.p. 187° to 188° C. (from diethyl ether)

EXAMPLE 87

5-(Cyclohexylaminocarbonyl)-3-ethyloxypyridine-2-carboxylic acid (glycyl ethyl ester) amide

EXAMPLE 88

5-((2-Phenylethyl)aminocarbonyl)-3-methoxypyridine-2-carboxylic acid (glycyl ethyl ester) amide

EXAMPLE 89

5-((+)-Dehydroabietylaminocarbonyl)-3-methoxypyridine-2-carboxylic acid (glycyl ethyl ester)

a) 5-((+)-Dehydroabietylaminocarbonyl)-3-methoxypyridine-2-carboxylic acid

The resinous product was obtained, in analogy with Example 90a), from methyl 5-carboxy-3-methoxypyridine-2-carboxylate and (+)-dehydroabietylamine.

b) The title compound was obtained, in analogy with Example 90c), after hydrolysis, from the above compound, m.p. from 150° C. with foaming (sintering at 120° C., from diethyl ether).

EXAMPLE 90

5-((2-(4-Fluorophenyl) ethyl)aminocarbonyl)-3-methoxypyridine-2-carboxylic acid (glycyl ethyl ester) amide a) Methyl 5-carboxy-3-methoxypyridine-2-carboxylate 10 g (50.7 mmol) of the 3-methoxypyridine-2,5-dicarboxylic acid (Example 81c) were suspended in 150 ml of anhydrous methanol, and after that 2 ml of concentrated sulfuric acid were added and the mixture was heated under reflux for 3 hours. Half of the methanol was then distilled off in vacuo and the residue introduced into 400 ml of ice water; the crystalline residue was filtered off with suction and washed with water; the residue was dissolved in 150 ml of a saturated, aqueous solution of Na bicarbonate and this mixture extracted twice with 80 ml of dichloromethane on each occasion; the bicarbonate phase was adjusted to pH 1, while cooling, with half-concentrated aqueous hydrochloric acid and the precipitated product was filtered off with suction and dried. 5 g of colorless, crystalline, substance were obtained, m.p. 196° to 197° C. 1.7 g of dimethyl ester, m.p. 53° to 55° C. (from petroleum ether), were obtained from the dichloromethane phase.

b) 5-(((2-(4-Fluorophenyl) ethyl) amino)carbonyl)-3-methoxypyridine-2-carboxylic acid 3.2 g of methyl 5-carboxy-3-methoxypyridine-2-carboxylate were suspended in 300 ml of anhydrous dichloromethane, and after that 2.0 ml (15 mmol) of 2-(4-fluorophenyl)ethylamine, 1.95 ml (15 mmol) of N-ethylmorpholine, 2.2 g (16.5 mmol) of 1-hydroxy-1H-benzotriazole and 6.35 g (15 mmol) of N-cyclohexyl-N'-(2- morpholinoethyl)carbodiimide methyl-p-toluenesulphonate (CMC) were added sequentially, at 20° C. and while stirring, and the mixture was stirred for 24 hours. The undissolved material was then filtered off and the organic phase was extracted, in each case 3 x, with an aqueous solution of Na bicarbonate, with 1N aqueous hydrochloric acid and with water, and the organic phase was dried and concentrated. 3.7 g were obtained of methyl ester (m.p. 168° to 169° C.) which was introduced into 150 ml of 1.5N methanolic NaOH. After 30 minutes, the mixture was concentrated and dissolved in 100 ml of water, and this mixture was adjusted to pH 1 with conc. aqueous hydrochloric acid; the crystalline precipitate was filtered off with suction, washed with water and dried. 3.4 g of product were obtained, m.p. 110° C. (with foaming, sintering at 75° C.).

c) In analogy with Example 90a), 3.2 g (10 mmol) of the. above compound were reacted with 1.4 g (10 mmol) of glycine ethyl ester hydrochloride, N-ethylmorpholine, 1-hydroxy-1H-benzotriazole and CMC. Following analogous working up, 2.8 g of the colorless crystalline product were crystallized using diisopropyl ether, m.p. 170° to 171° C.

EXAMPLE 91

5-((2-(4-Methoxyphenyl)ethyl)aminocarbonyl)-3-ethyloxypyridine-2-carboxylic acid (glycyl ethyl ester) amide

EXAMPLE 92

5–Chloro-3-ethyloxypyridine-2-carboxylic acid (glycyl ethyl ester) amide

EXAMPLE 93

5–Chloro-3-ethyloxypyridine-2-carboxylic acid (glycyl ethyl ester) amide

EXAMPLE 94

5–Cyclohexyloxymethyl-3-methoxypyridine-2-carboxylic acid (glycyl ethyl ester) amide

EXAMPLE 95

5-(3-Methylbutyl)oxymethyl-3-methoxypyridine-2-carboxylic acid (glycyl ethyl ester) amide

EXAMPLE 96

5-Benzyloxymethyl-3-ethyloxypyridine-2-carboxylic acid (glycyl ethyl ester) amide

EXAMPLE 97

3-((Cyclohexyl)methyloxy)pyridine-2-carboxylic acid (glycyl ethyl ester) amide

EXAMPLE 98

3-((2–Cyclohexyl)ethyloxy)pyridine-2-carboxylic acid (glycyl ethyl ester) amide

EXAMPLE 99

3-((3-Cyclohexyl)propyloxy)pyridine-2-carboxylic acid (glycyl ethyl ester) amide

EXAMPLE 100

3-(3-Methylbutyloxy)pyridine-2-carboxylic acid (glycyl ethyl ester) amide

EXAMPLE 101

3-Hexyloxypyridine-2-carboxylic acid (glycyl ethyl ester) amide

EXAMPLE 102

3-(4-Ethylbenzyloxy)pyridine-2-carboxylic acid (glycyl ethyl ester) amide

EXAMPLE 103

3-(4-Propylbenzyloxy)pyridine-2-carboxylic acid (glycyl ethyl ester) amide

EXAMPLE 104

3-(4-Butylbenzyloxy)pyridine-2-carboxylic acid (glycyl ethyl ester) amide

EXAMPLE 105

3-(4-tert-Butylbenzoyloxy)pyridine-2-carboxylic acid (glycyl ethyl ester) amide

EXAMPLE 106

6-(3-Methoxybenzyloxy)-3-ethyloxypyridine-2-carboxylic acid (glycyl ethyl ester) amide

EXAMPLE 107

3-(4-Trifluoromethylbenzyloxy)pyridine-2-carboxylic acid (glycyl methyl ester) amide

EXAMPLE 108

3-(4-(2-Propyl)benzyloxy)pyridine-2-carboxylic (glycyl methyl ester) amide

EXAMPLE 109

3-(3-Fluorobenzyloxy)pyridine-2-carboxylic acid (glycyl methyl ester) amide

EXAMPLE 110

3-(4-Fluorobenzyloxy)pyridine-2-carboxylic acid (glycyl methyl ester) amide

EXAMPLE 111

3-(2,4-Dichlorobenzyloxy)pyridine-2-carboxylic acid (glycyl methyl ester) amide

EXAMPLE 112

3-(4-(2,2,2-Trifluoroethyloxy)benzyloxy)pyridine-2-carboxylic acid (glycyl methyl ester) amide

EXAMPLE 113

3-(4-Chlorobenzyloxy)pyridine-2-carboxylic acid (glycyl butyl ester) amide

EXAMPLE 114

3-(3,4-Dichlorobenzyloxy)pyridine-2-carboxylic acid (glycyl butyl ester) amide

EXAMPLE 115

3-(3-Trifluoromethylbenzyloxy)pyridine-2-carboxylic acid (glycyl butyl ester)

EXAMPLE 116

3-(4-Trifluoromethylbenzyloxy)pyridine-2-carboxylic acid (glycyl buryl ester) amide

EXAMPLE 117

3-(4-(2-Propyl)benzyloxy)pyridine-2-carboxylic acid (glycyl butyl ester) amide

EXAMPLE 118

3-(4-Fluorobenzyloxy)pyridine-2-carboxylic acid (glycyl butyl ester) amide

EXAMPLE 119

3-(4-(2,2,2-Trifluoroethyloxy)benzyloxy)pyridine-2-carboxylic acid (glycol butyl ester) amide

EXAMPLE 120

3-(4-Trifluoromethylbenzyloxy)pyridine-2-carboxylic acid (glycyl 3-pentyl ester) amide

EXAMPLE 121

3-(4-(2-Propyl)benzyloxy)pyridine-2-carboxylic acid (glycyl 3-pentyl ester) amide

EXAMPLE 122

3-(3-Fluorobenzyloxy)pyridine-2-carboxylic acid (glycyl 2-ethylbutyl ester) amide

EXAMPLE 123

3-(4-Fluorobenzyloxy)pyridine-2-carboxylic acid (glycyl 2-ethylbutyl ester) amide

EXAMPLE 124

3-(4-(2,2,2-Trifluoroethyloxy)benzyloxy)pyridine-2-carboxylic acid (glycyl 3-methylbutyl ester) amide

EXAMPLE 125

3-(Fluorobenzyloxy)pyridine-2-carboxylic acid (glycyl 3-methylbutyl ester) amide

EXAMPLE 126

3-(3-Trifluoromethylbenzyloxy)pyridine-2-carboxylic acid (glycyl cyclohexyl ester) amide

EXAMPLE 127

3-(4-Trifluoromethylbenzyloxy)pyridine-2-carboxylic acid (glycyl benzyl ester) amide

EXAMPLE 128

3-(4-(2-Propyl)benzyloxy)pyridine-2-carboxylic acid (glycyl benzyl ester) amide

EXAMPLE 129

3-(3-Fluorobenzyloxy)pyridine-2-carboxylic acid (glycyl benzyl ester) amide

EXAMPLE 130

3-(4-Fluorobenzyloxy)pyridine-2-carboxylic acid (glycyl benzyl ester) amide

EXAMPLE 131

3-(2,4-Dichlorobenzyloxy)pyridine-2-carboxylic acid (glycyl benzyl ester) amide

EXAMPLE 132

3-(4-(2,2,2-Trifluoroethyloxy)benzyloxy)pyridine-2-carboxylic acid (glycyl benzyl ester) amide

EXAMPLE 133

3-(Fluorobenzyloxy)pyridine-2-carboxylic acid (glycyl hexyl ester) amide

EXAMPLE 134

3-(4-Chlorobenzyloxy)pyridine-2-carboxylic acid (glycyl octyl ester) amide

EXAMPLE 135

3-(3-Trifluoromethylbenzyloxy)pyridine-2-carboxylic acid (glycyl hexyl ester) amide

EXAMPLE 136

3-(4-Trifluoromethylbenzyloxy)pyridine-2-carboxylic acid (glycyl 2-ethoxyethyl ester) amide

EXAMPLE 137

3-(4-(2-Propyl)benzyloxy)pyridine-2-carboxylic acid (glycyl 2-ethoxyethyl ester) amide

EXAMPLE 138

3-(4-Fluorobenzyloxy)pyridine-2-carboxylic acid (glycyl 2-butoxyethyl ester) amide

EXAMPLE 139

3-(4-Fluorobenzyloxy)pyridine-2-carboxylic acid (glycyl methylcyclohexyl ester) amide

EXAMPLE 140

3-(4-(2,2,2-Trifluoroethyloxy)benzyloxy)pyridine-2-carboxylic acid (glycyl methylcyclohexyl ester) amide

EXAMPLE 141

3-(Fluorobenzloxy)pyridine-2-carboxylic acid (glycyl 2-propyl ester) amide

EXAMPLE 142

3-(3,4-Dichlorobenzyloxy)pyridine-2-carboxylic acid (glycyl 2-propyl ester) amide

EXAMPLE 143

3-(4-Trifluoromethylbenzyloxy)pyridine-2-carboxylic acid (glycyl 2-propyl ester) amide

EXAMPLE 144

3-Benzyloxypyridine-2-carboxylic acid (glycyl benzyl ester) amide

EXAMPLE 145

3-Benzyloxypyridine-2-carboxylic acid (glycyl hexyl ester) amide

EXAMPLE 146

3-Methoxypyridine-2-carboxylic acid N-(((hexadecyloxy)-carbonyl)methyl)amide hydrochloride 7.7 ml (60mmol) of N-ethylmorpholine, 4.5 g (33mmol) of 1-hydroxy-1H-benzotriazole and 12.8 g (30 mmol) of N-cyclohexyl-N'-(2-morpholinoethyl)-carbodiimide methyl-p-toluenesulfonate (CMC) were added, in analogy with Examples 90b) and c), to 5.7 g (30 mmol) of 4-chloro-3-methoxypyridine-2-carboxylic acid and 14.2 g (30mmol) of glycine hexadecyl ester tosylate (m.p. approximately 90° C., prepared from glycine, 1-hexadecanol and p-toluenesulfonic acid on a water separator using toluene) in 300 ml of dichloromethane, and the mixture was stirred for 24 h. The undissolved material was then filtered off with suction and the filtrate was extracted by shaking with an aqueous solution of Na bicarbonate, with water and with aqueous hydrochloric acids the organic phase was concentrated and the residue (14 g) was dissolved in 500 ml of tetrahydrofuran/methanol (1:1), and after that Pd/C (10%) was added to this mixture, which was hydrogenated using a hydrogenation vessel. Once the uptake of hydrogen was complete, the catalyst was filtered off with suction and the filtrate was concentrated and the residue chromatographed on silica gel using ethyl acetate. Appropriate fractions were concentrated and the residue was crystallized using diisopropyl ether. 2.1 g of the title compound were obtained as a colorless substance, m.p. 63°–65° C.

EXAMPLE 147

3-Methoxypyridine-2-carboxylic acid N-(((1-octyloxy) carbonyl)methyl)amide 2.5 g (13 mmol) of 3-methoxypyridine-2-carboxylic acid hydrochloride (m.p. 170° C. with decomp. (from ethyl acetate)), 5.5 ml (45 mmol) N-ethylmorpholine, 2 g (15 mmol) of 1-hydroxy-(1H)-benzotriazole, 4.7 g (13 mmol) of glycine octyl ester tosylate (prepared from glycine, octanol and p-Tos OH on a water separator using toluene) and 6.3 g (15 mmol) of CMC (cf. Example 146) were stirred for 48 h in 350 ml of anhydrous dichloromethane. Following a working up which was analogous to that in Example 146, the crude product was chromatographed on silica gel using dichloromethane (with the addition of up to 2.5% methanol during the course of this). 3.6 g were obtained of the colorless, oily title compound, $^1$H NMR (CDCl$_3$): δ=4.26 (d, CH$_2$-glycine).

EXAMPLE 148

3-Methoxypyridine-2-carboxylic acid N-(((1-hexyloxy) carbonyl)methyl)amide

EXAMPLE 149

3-Methoxypyridine-2-carboxylic acid N-(((1-butyloxy) carbonyl)methyl)amide

The title compound was obtained, in analogy with Example 147, using glycine 1-butyl ester tosylate, m.p. 60°–62° C. (from dichloromethane).

EXAMPLE 150

3-Methoxypyridine-2-carboxylic acid N-(((2-nonyloxy) carbonyl)methyl)amide racemate 2.5 g (10mmol) of 3-methoxypyridine-2-carboxylic acid N-(carboxymethyl)amide hydrochloride (m.p. 157° C. with gas evolution) were suspended in 100 ml of anhydrous tetrahydrofuran, and after that 1.6 ml (12 mmol) of triethylamine were added, followed by 2.4 g of pivaloyl chloride, dissolved in a little tetrahydrofuran, which was added dropwise while stirring (temperature rise to 35°–40° C.).

After 30 min., the mixture was concentrated in vacuo and the reddish residue was taken up in 100 ml of anhydrous tetrahydrofuran; 1.6 ml of triethylamine were added to this mixture, followed, at 20° C., by 30 ml of a solution of Na 2-nonoxide in 2-nonanol (prepared from 30 ml of 2-nonanol and 0.8 g (20 mmol) of NaH). After 1 h, the mixture was concentrated in vacuo and dichloromethane was added to the residue; this mixture was extracted by shaking with a 2N solution of aqueous ammonium chloride and the organic phase was dried and concentrated in vacuo and the residue (9 g) was chromatographed on silica gel using ethyl acetate. 1.1 g of the oily colorless title compound were obtained, $^1$H NMR (DMSO): δ=3.95 (d, CH$_2$-glycine).

EXAMPLE 151

3-Methoxypyridine-2-carboxylic acid N-(((4-heptyloxy) carbonyl)methyl)amide 2.5 g (10 mmol) of 3-methoxypyridine-2-carboxylic acid N-(carboxymethyl) amide hydrochloride were treated as in Example 150, and after that 140 ml of a solution of Na 4-heptoxide in 4-heptanol (prepared from 140 ml of heptanol and 0.6 g (25 mmol) of sodium, sonication bath) were added at 20° C. After 30 min, the mixture was heated at 70°–80° C. for 1 h and, after cooling, concentrated in vacuo; the residue was taken up in water and this mixture was extracted with dichloromethane and the organic phase concentrated in vacuo and dried on an oil pump. The oily crude product crystallizes after about 15 h, m.p. 75°–78° C.

EXAMPLE 152

3-Benzyloxypyridine-2-carboxylic acid N-(((1-octyloxy)carbonyl)methyl)amide 1.1 g (5 mmol) of 3-benzyloxypyridine-2-carboxylic acid were condensed with glycine 1-octyl ester tosylate in analogy with Example 147. 1.3 g of the title compound were obtained, without column chromatography, as a pale brown oil, $^1$H NMR (DMSO): δ=5.24 (s, CH$_2$-benzyl).

EXAMPLE 153

3-Benzyloxypyridine-2-carboxylic acid N-(((1-butyloxy)carbonyl)methyl)amide

In analogy with Example 152, the title compound was obtained using glycine 1-butyl ester tosylate. After extracting the organic phase with a saturated aqueous solution of Na bicarbonate, with 1N hydrochloric acid and with water, and drying and concentrating, the residue was crystallized using ether/petroleum ether, m.p. 55°–58° C.

EXAMPLE 154

5-(((3-(1-Butyloxy)propyl)amino)carbonyl)-3-methoxypyridine-2-carboxylic acid N-((benzyloxycarbonyl)methyl)amide a) Methyl 5-(((3-(1-butyloxy)propyl)amino)carbonyl)-3-methoxypyridine-2-carboxylate 1.7 ml of oxalyl chloride (20 mmol), and also 2 drops of N,N-dimethylformamide, dissolved in tetrahydrofuran, were added dropwise, at 10° C. and while stirring, to 2.1 g (10 mmol) of methyl 5-carboxy-3-methoxypyridine-2-carboxylate in 100 ml of anhydrous tetrahydrofuran and the reaction mixture was stirred at 10° C. for 30 min and at 20° C. for 1 h. It was then concentrated and the residue was dissolved in dichloromethane; 6.8 ml (50 mmol) of triethylamine, and then 1.3 g (1.5 ml, 10 mmol) of 3-butoxypropylamine, dissolved in dichloromethane, were added, at 0° C., to this solution.

After 30 min, the mixture was allowed to warm to room temperature and was extracted with water, Na bicarbonate solution and aqueous 1N HCl; the organic phase was dried and concentrated and the residue was crystallized using diethylether/petroleumether (3:1). 2.3 g of product were obtained, m.p. 51°–53° C.

b) The above substance was hydrolyzed by standard procedures, and 1.5 g (5 mmol) of the amorphous 5-(((3-(1-butyloxy)propyl)amino)carbonyl)-3-methoxypyridine-2-carboxylic acid, which was dried on an oil pump, was reacted with glycine benzyl ester tosylate, N-ethylmorpholine, 1-hydroxy-(1H)-benzotriazole and CMC (as described). 1.42 g of the title compound were crystallized using acetone, m.p. 97°–99° C.

EXAMPLE 155

5-(((3-(1-Butyloxy)propyl)amino)carbonyl)-3-methoxypyridine-2-carboxylic acid N-(((1-butyloxy)carbonyl)methyl)amide The title compound was obtained, in analogy with the above example, using glycine 1-butyl ester tosylate (m.p. 80°–82° C. (from toluene)), m.p. 115°–117° C. (from diisopropyl ether).

EXAMPLE 156

5-(((3-Lauryloxy)propyl)amino)carbonyl)-3-methoxypyridine-2-carboxylic acid N-(((benzyloxy)carbonyl)methyl)amide In analogy with Example 154, the title compound was obtained using 3-lauryloxypropylamine, m.p. from 109°–111° C. (from diisopropyl ether).

EXAMPLE 157

5-(((2-Methoxyethyl)amino)carbonyl)-3-methoxypyridine-2-carboxylic acid N-((benzoxylcarbonyl)methyl)amide The title compound was obtained, in analogy with Example 154, using 2-methoxyethylamine.

a) 5-(((2-Methoxyethyl)amino)carbonyl)-3-methoxypyridine-2-carboxylic acid

M.p. 160°–161° C. (with gas evolution, from ethyl acetate)

b) The title compound was crystallized using diisopropyl ether, m.p. 129°–131° C.

The following examples were prepared in analogy with Example Nos. 146–157.

EXAMPLE 158

3-Methoxypyridine-2-carboxylic acid N-(((2-propyloxy)carbonyl)methyl)amide

EXAMPLE 159

3-Methoxypyridine-2-carboxylic acid N-(((1-propyloxy)carbonyl)methyl)amide

EXAMPLE 160

3-Methoxypyridine-2-carboxylic acid N-(((1-pentyloxy)carbonyl)methyl)amide

EXAMPLE 161

3-Methoxypyridine-2-carboxylic acid N-(((3-pentyloxy)carbonyl)methyl)amide

EXAMPLE 162

3-Methoxypyridine-2-carboxylic acid N-(((1-decyloxy)carbonyl)methyl)amide

EXAMPLE 163

3-Methoxypyridine-2-carboxylic acid N-(((1-dodecyloxy)carbonyl)methyl)amide

EXAMPLE 164

3-Methoxypyridine-2-carboxylic acid N-(((1-geranyloxy)carbonyl)methyl)amide

EXAMPLE 165

3-Benzyloxypyridine-2-carboxylic acid N-(((2-propyloxy)carbonyl)methyl)amide

EXAMPLE 166

3-Benzyloxypyridine-2-carboxylic acid N-(((3-pentyloxy)carbonyl)methyl)amide

EXAMPLE 167

3-Benzyloxypyridine-2-carboxylic acid N-(((1-pentyloxy)carbonyl)methyl)amide

EXAMPLE 168

3-Benzyloxypyridine-2-carboxylic acid N-(((1-dodecyloxy)carbonyl)methyl)amide

EXAMPLE 169

3- Benzyloxypyridine-2-carboxylic acid N-(((1-geranyloxy)carbonyl)methyl)amide

EXAMPLE 170

5-(((3-(1-Butyloxy)propyl)amino)carbonyl)-3-methoxypyridine-2-carboxylic acid N-(((1-hexyloxy)carbonyl)methyl)amide

EXAMPLE 171

5-(((3-(1-Butyloxy)propyl)amino)carbonyl)-3-methoxypyridine-2-carboxylic acid N-(((hex-3-en-1-yloxy)carbonyl)methyl)amide

EXAMPLE 172

5-(((3-(1-Butyloxy)propyl)amino)carbonyl)-3-methoxypyridine-2-carboxylic acid N-(((1-octyloxy)carbonyl)methyl)amide

EXAMPLE 173

5-(((3-(1-Butyloxy)propyl)amino)carbonyl)-3-methoxypyridine-2-carboxylic acid N-(((1-decyloxy)carbonyl)methyl)amide.

EXAMPLE 174

5-(((3-(1-Butyloxy)propyl)amino)carbonyl)-3-methoxypyridine-2-carboxylic acid N-(((1-dodecyloxy)carbonyl)methyl)amide

EXAMPLE 175

5-(((3-(1-Butyloxy)propyl)amino)carbonyl)-3-methoxypyridine-2-carboxylic acid N-(((3-methyl)-1-butyloxy)carbonyl)methyl)amide

EXAMPLE 176

5-(((3-(1-Butyloxy)propyl)amino)carbonyl)-3-methoxypyridine-2-carboxylic acid N-(((1-geranyloxy)carbonyl)methyl)amide

EXAMPLE 177

5-(((4-(1-Butyloxy)phenyl)amino)carbonyl)-3-chloropyridine-2-carboxylic acid N-((ethyloxycarbonyl)methyl)amide a) Methyl 5-carboxy-3-chloropyridine-2-carboxylate was prepared in analogy with Example 90a), m.p. 182°–184° C. (from aqueous hydrochloric acid).

b) Methyl 5-(((4-(1-butyloxy)phenyl)amino)carbonyl)-3-chloropyridine-2-carboxylate was obtained from the above compound using oxalyl chloride and 4-(1-butyloxy)aniline, m.p. 121°–123° C. (from diethyl ether).

c) 5-(((4-(1-Butyloxy)phenyl)amino)carbonyl)-3-chloropyridine-2-carboxylic acid by hydrolysis of the product from b), m.p. 163°–164° C. (from aqueous hydrochloric acid).

d) The title compound was obtained, in analogy with Example 90b), from the above substance by condensation (N-ethylmorpholine, 1-hydroxy-1H-benzotriazole and CMC) with glycine ethyl ester hydrochloride, m.p. 177°–179° C. (from ethanol).

EXAMPLE 178

3-(4-Chlorobenzyloxy)pyridine-2-carboxylic acid N-(((ethyloxy)carbonyl)methyl)amide 1-oxide 0.7 g (2 mmol) of the title compound from Example 31 was dissolved in dichloromethane and reacted with 1.41 g of 3-chloroperbenzoic acid. After the mixture had been stirred at 20° C. for 1 h, ammonia was passed in until no more precipitation took place and the mixture was then filtered and the filtrate concentrated and the oily residue crystallized using diethyl ether, m.p. 70°–72° C.

EXAMPLE 179

5-Methoxycarbonyl-3-(2-methyl-1-propyloxy)-pyridine-2-carboxylic acid (glycyl benzyl ester) amide a) 3-(2-Methyl-1-propyloxy)-pyridine-2,5-dicarboxylic acid In analogy with Example 81c), 3.5 g (146 mmol) of sodium were dissolved in 350 ml of 2-methyl-1-propanol (isobutyl alcohol), and after that 13.7 g (55 mmol) of 3-chloropyridine-2-carboxylic ethyl ester 5-carboxylic methyl ester (prepared in analogy with Example 81b)) were added at 20° C. and while stirring. The mixture was then stirred at 80° C. for 90 minutes and, after cooling, concentrated in vacuo; the residue was taken up in 200 ml of 1N methanolic NaOH and this mixture was stirred at 20° C. After 15 minutes, the solution became cloudy. Water was added until a clear solution was obtained and this was stirred for 1 hour and then concentrated in vacuo; the aqueous solution was acidified with aqueous hydrochloric acid and the crystalline product was filtered off with suction, washed and dried, and 10.6 g of dicarboxylic acid were obtained, m.p. 192° C. (decomp.).

b) Dimethyl 3-(2-methyl-1-propyloxy)pyridine-2,5-dicarboxylate

The oily product was obtained from the above dicarboxylic acid under esterification conditions (methanol/sulfuric acid) and after working up (washing with water and extracting with ethyl acetate).

c) 0.48 g (12 mmol) of NaOH, dissolved in 50 ml of methanol, was added to 3.2 g (12 mmol) of the above diester in 25 ml of methanol, and the mixture was stirred at 65° C. for 90 minutes. The mixture was then acidified, while being cooled, with dilute aqueous hydrochloric acid and freed from methanol in vacuo. 2.5 g (10 mmol) of the monoester mixture thus obtained were stirred, in analogy with Example 90b), in 250 ml of dichloromethane, at 20° C. for 24 hours, together with 3.4 g (10 mmol) of glycine benzyl ester tosylate, 1.4 g (10 mmol) of 1-hydroxy-1H-benzotriazole, 2.6 ml (20 mmol) of N-ethylmorpholine and 4.3 g (10 mmol) of CMC.

The undissolved material was then filtered off with suction and the filtrate was extracted with an aqueous solution of Na bicarbonate, with dilute hydrochloric acid and with water; the organic phase was dried and concentrated and the residue was chromatographed on silica gel using n-heptane/ethyl acetate (1:1). 0.8 g of the colorless title compound was obtained from appropriate fractions, m.p. 103° to 105° C. 1.1 g of the isomeric resinous product are also obtained.

Examples 108–228 were prepared in an analogous manner:

EXAMPLE 180

5-Ethoxycarbonyl-3-(2-methyl-1-propyloxy)pyridine-2-carboxylic acid (glycol ethyl ester) amide

EXAMPLE 181

5-Methoxycarbonyl-3-(3-methyl-1-butyloxy)pyridine-2-carboxylic acid (glycyl ethyl ester) amide

EXAMPLE 182

5-Ethoxycarbonyl-3-ethoxypyridine-2-carboxylic acid (glycyl ether ester) amide

EXAMPLE 183

5-Ethoxycarbonyl-3-(1-propyloxy)pyridine-2-carboxylic acid (glycyl ethyl ester) amide

EXAMPLE 184

5-Ethoxycarbonyl-3-(2-propyloxy)pyridine-2-carboxylic acid (glycyl ethyl ester) amide

EXAMPLE 185

3-Benzyloxy-5-ethoxycarbonylpyridine-2-carboxylic acid (glycyl ethyl ester) amide

EXAMPLE 186

3-(4-Chlorobenzyloxy)-5-ethoxycarbonylpyridine-2-carboxylic acid (glycyl ethyl ester) amide

EXAMPLE 187

5-Ethoxycarbonyl-3-(4-fluorobenzyloxy)pyridine-2-carboxylic acid (glycyl 1-butyl ester) amide

EXAMPLE 188

5-Ethoxycarbonyl-3-(4-(trifluoromethyl)benzyloxy) pyridine-2-carboxylic acid (glycyl 1-butyl ester) amide

EXAMPLE 189

5-Ethoxycarbonyl-3-(4-(trifluoromethoxy)benzyloxy) pyridine-2-carboxylic acid (glycyl 1-butyl ester) amide

EXAMPLE 190

5-Ethoxycarbonyl-3-(4-(2-propyl)benzyloxy)pyridine-2-carboxylic acid (glycyl 1-butyl ester)amide

EXAMPLE 191

3-(4-Ethoxybenzyloxy)-5-ethoxycarbonylpyridine-2-carboxylic acid (glycyl 1-butyl ester) amide

EXAMPLE 192

5-Ethoxycarbonyl-3-(3,4-dimethoxybenzyloxy)pyridine-2-carboxylic acid (glycyl 1-butyl ester) amide

EXAMPLE 193

5-Ethoxycarbonyl-3-(2-(4-fluorophenyl)ethyloxy) pyridine-2-carboxylic acid (glycyl 1-butyl ester) amide

EXAMPLE 194

5-Ethoxycarbonyl-3-(2,2,2-trifluoroethyloxy)pyridine-2-carboxylic acid (glycyl 1-butyl ester) amide

EXAMPLE 195

5-Carboxy-3-(3-methyl-1-butyloxy)pyridine-2-carboxylic acid (glycyl 1-octyl ester)

EXAMPLE 196

5-Carboxy-3-ethoxypyridine-2-carboxylic acid (glycyl 1-octyl ester)

EXAMPLE 197

5-Carboxy-3-propyloxypyridine-2-carboxylic acid (glycyl 1-octyl ester) amide

EXAMPLE 198

5-Carboxy-3-(2-propyloxy)pyridine-2-carboxylic acid (glycyl 1-octyl ester) amide

EXAMPLE 199

3-Benzyloxy-5-carboxypyridine-2-carboxylic acid (glycyl 1-octyl ester) amide

EXAMPLE 200

5-Carboxy-3-(4-chlorobenzyloxy)pyridine-2-carboxylic acid (glycyl 1-octyl ester) amide

EXAMPLE 201

5-Carboxy-3-(4-fluorobenzyloxy)pyridine-2-carboxylic acid (glycyl 1-octyl ester) amide

EXAMPLE 202

5-Carboxy-3-((4-trifluoromethyl) benzyloxy)pyridine-2-carboxylic acid (glycyl 1-octyl ester) amide

EXAMPLE 203

5-Carboxy-3-((trifluoromethoxy)benzyloxy)pyridine-2-carboxylic acid (glycyl 1-octyl ester) amide

EXAMPLE 204

5-Carboxy-3-(4-(2-propyl)benzyloxy)pyridine-2-carboxylic acid (glycol 1-octyl ester) amide

EXAMPLE 205

5-Carboxy-3-(naphthyl-2-methyloxy)pyridine-2-carboxylic acid (glycyl 1-butyl ester) amide

EXAMPLE 206

5-Carboxy-3-(naphthyl-1-methyloxy)pyridine-2-carboxylic acid (glycyl 1-butyl ester) amide

EXAMPLE 207

5-(3-Pentyloxy)carbonyl-3-propyloxypyridine-2-carboxylic acid (glycyl 1-octyl ester) amide

EXAMPLE 208

5-(3-Pentyloxy)carbonyl-3-(2-propyloxy)pyridine-2-carboxylic acid (glycyl 1-octyl ester) amide

EXAMPLE 209

3-Benzyloxy-5-(3-pentyloxy)carbonylpyridine-2-carboxylic acid (glycyl 1-octyl ester) amide

EXAMPLE 210

3-(4-Fluorobenzyloxy)-5-(3-pentyloxy)carbonylpyridine-2-carboxylic acid (glycyl 1-butyl ester) amide

EXAMPLE 211

5-(4-Heptyloxy) carbonyl-3-methoxypyridine-2-carboxylic acid (glycyl 1-butyl ester) amide

EXAMPLE 212

3-Benzyloxy-5-(4-heptyloxy)carbonylpyridine-2-carboxylic acid (glycyl 1-octyl ester) amide

EXAMPLE 213

3-(4-Chlorobenzyloxy)-5-(4-heptyloxy) carbonylpyridine-2-carboxylic acid (glycyl 1-octyl ester) amide

EXAMPLE 214

3-(4-Fluorobenzyloxy)-5-(4-heptyloxy)pyridine-2-carboxylic acid (glycyl 1-hexyl ester) amide

EXAMPLE 215

5-(4-Heptyloxy)carbonyl-3-(4-(2-propyl)benzyloxy)pyridine-2-carboxylic acid (glycyl 1-butyl ester) amide

EXAMPLE 216

3-Benzyloxy-5-((5-nonyloxy)carbonyl)pyridine-2-carboxylic acid (glycyl 1-hexyl ester) amide

EXAMPLE 217

3-(4-Fluorobenzyloxy)-5-(5-nonyloxy)carbonylpyridine-2-carboxylic acid (glycyl 1-hexyl ester) amide

EXAMPLE 218

5-(5-Nonyloxy)carbonyl-3-(4-(2-propyl)benzyloxy)pyridine-2-carboxylic acid (glycyl 1-butyl ester) amide

EXAMPLE 219

5-Geranyloxycarbonyl-3-(2-methyl-1-propyloxy)pyridine-2-carboxylic acid (glycyl 1-butyl ester) amide

EXAMPLE 220

3-Benzyloxy-5-(geranyloxycarbonyl)pyridine-2-carboxylic acid (glycyl 1-butyl ester) amide

EXAMPLE 221

3-(4-Fluorobenzyloxy)-5-(geranyloxycarbonyl)pyridine-2-carboxylic acid (glycyl ethyl ester) amide

EXAMPLE 222

5-Geranyloxycarbonyl-3-(3-methoxybenzyloxy)pyridine-2-carboxylic acid (glycyl ethyl ester) amide

EXAMPLE 223

3-Benzyloxy-5-(farnesyloxycarbonyl)pyridine-2-carboxylic acid (glycyl ethyl ester) amide

EXAMPLE 224

5-Farnesyloxycarbonyl-3-(4-fluorobenzyloxy)pyridine-2-carboxylic acid (glycyl ethyl ester) amide

EXAMPLE 225

3-Methoxy-5-(retinyloxycarbonyl)pyridine-2-carboxylic acid (glycyl ethyl ester) amide

EXAMPLE 226

3-Ethoxy-5-(retinyloxycarbonyl)pyridine-2-carboxylic acid (glycyl ethyl ester) amide

EXAMPLE 227

3-Benzyloxy-5-(retinyloxycarbonyl)pyridine-2-carboxylic acid (glycyl ethyl ester) amide

EXAMPLE 228

3-(4-Fluorobenzyloxy)-5-(retinyloxycarbonyl)pyridine-2-carboxylic acid (glycyl 1-butyl ester) amide

EXAMPLE 229

5-(((4-n-Butyloxyphenyl)amino)carbonyl)-3-methoxypyridine-2-carboxylic acid (glycyl ethyl ester) amide a) Methyl 5-(((4-n-butyloxyphenyl)amino)carbonyl)-3-methoxypyridine-2-carboxylate 3.2 g (15 mmol) of methyl 5-carboxy-3-methoxyyridine-2-carboxylate (cf. Example 90a)) were reacted, in analogy with Example 90b), with 2.5 g (15 mmol) of 4-n-butoxyaniline and the reagents described in that example. 3.9 g of product were crystallized using diethyl ether (m.p. 138°–141° C.

b) 5-(((4-n-Butyloxyphenyl)amino)carbonyl)-3-methoxypyridine-2-carboxylic acid 3.2 g of the above ester were hydrolyzed at 20° C. using 100 ml of 1.5N methanolic sodium hydroxide solution. 2.7 g of product were obtained from aqueous hydrochloric acid, m.p. 128°–130° C., sintering from 120° C.

c) 5-(((4-n-Butyloxyphenyl)amino)carbonyl)-3-methoxypyridine-2-carboxylic acid N-(ethoxycarbonylmethyl) amide The title compound was prepared as follows: 2.7 g (7.8 mmol) of the above pyridine-2-carboxylic acid were stirred in 500 ml of anhydrous dichloromethane, at 20° C. for 24 h, together with 1.1 g (7.8 mmol) of glycine ethyl ester hydrochloride, 3.0 ml (23.4 mmol) of N-ethylmorpholine, 1.2 g (8.6 mmol) of 1-hydroxy-(1H)-benzotriazole and 3.3 g (7.8 mmol) of CMC. The undissolved material was then filtered off and the organic phase was extracted sequentially with 200 ml each of water, an aqueous solution of Na bicarbonate, 1N aqueous hydrochloric acid and water, dried over Mg sulfate and concentrated in vacuo; the residue was crystallized using diethyl ether. 2.4 g of product were obtained, m.p. 193°–195° C.

EXAMPLE 230

5-(((4-(1-Hexyloxy)phenyl)amino)carbonyl)-3-methoxypyridine-2-carboxylic acid N-((ethoxy carbonyl)methyl)amide a) Methyl 5-(((4-n-hexyloxyphenyl)amino)carbonyl)-3-methoxypyridine-2-carboxylate was prepared from methyl 5-carboxy-3-methoxypyridine-2-carboxylate and 4-hexyloxyaniline, m.p. 118°–119° C. (from diethyl ether).

b) 5-(((4-n-Hexyloxyphenyl)amino)carbonyl)-3-methoxypyridine-2-carboxylic acid, 160°–162°, sintering at 148° C. (from aqueous hydrochloric acid/tetrahydrofuran)

c) The title compound was obtained, in analogy with Example 231c), from 4.2 g of the above compound. 4.0 g of product were crystallized using ethyl acetate, m.p. 157°–159° C.

EXAMPLE 231

5-(((4-n-Decylphenyl)amino)carbonyl)-3-methoxypyridine-2-carboxylic acid N-(ethoxycarbonylmethyl)amide was prepared from 5-(((-4-n-decylphenyl)amino)carbonyl)-3-methoxypyridine-2-carboxylic acid (m.p. 160° C., decomp.; from aqueous hydrochloric acid/THF) and glycine ethyl ester hydrochloride, m.p. 155°–157° C. (from diisopropyl ether).

Example nos. 232 to 240 were prepared in analogy with Examples 229 to 231.

EXAMPLE 232

5-(((4-Ethoxyphenyl)amino)carbonyl)-3-methoxypyridine-2-carboxylic acid (glycyl 1-octyl ester) amide

EXAMPLE 233

5-(((4-Ethoxyphenyl)amino)carbonyl)-3-benzyloxypyridine-2-carboxylic acid (glycyl 1-octyl ester) amide

EXAMPLE 234

5-(((4-n-Butyloxyphenyl)amino)carbonyl)-3-(4-fluorobenzyloxy)pyridine-2-carboxylic acid (glycyl 1-butyl ester) amide

EXAMPLE 235

5-(((4-n-Butyloxyphenyl)amino)carbonyl)-3-benzyloxypyridine-3-carboxylic acid (glycyl 1-butyl ester) amide

EXAMPLE 236

5-(((4-(1-Hexyloxy)phenyl)amino)carbonyl)-3-methoxypyridine-2-carboxylic acid (glycyl 1-octyl ester) amide

EXAMPLE 237

5-(((4-n-Decyloxyphenyl)amino)carbonyl)-3-methoxypyridine-2-carboxylic acid N-(((1-butyloxy)carbonyl)methyl)amide

EXAMPLE 238

5-(((4-Geranyloxyphenyl)amino)carbonyl)-3-methoxypyridine-2-carboxylic acid N-((1-hexyloxy)carbonyl)methyl)amide

EXAMPLE 239

5-(((4-n-Octyloxyphenyl)amino)carbonyl)-3-methoxypyridine-2-carboxylic acid N-((-1-butyloxy)carbonyl)methyl) amide

EXAMPLE 240

5-(((4-n-Octyloxyphenyl)amino)carbonyl)-3-methoxypyridine-2-carboxylic acid N-(((1-hexyloxy)carbonyl)methyl) amide

EXAMPLE 241

5-Farnesyloxycarbonyl-3-methoxypyridine-2-carboxylic acid (glycyl 1-butyl ester) amide

EXAMPLE 242

5-Geranyloxycarbonyl-3-methoxypyridine-2-carboxylic acid (glycyl ethyl ester) amide

EXAMPLE 243

5-(Farnesyloxymethyl)-3-methoxypyridine-2-carboxylic acid (glycyl ethyl ester) amide

EXAMPLE 244

5-(Geranyloxymethyl)-3-methoxypyridine-2-carboxylic acid (glycyl 1-butyl ester) amide

EXAMPLE 245

5-Retinyloxymethyl-3-methoxypyridine-2-carboxylic acid (glycyl 1-butyl ester) amide

EXAMPLE 246

5-Retinyloxymethyl-3-(2-propyloxy)pyridine-2-carboxylic acid (glycyl 1-butyl ester) amide

EXAMPLE 247

5-(1-Butoxymethyl)-3-methoxypyridine-2-carboxylic acid N-(((1-octyloxy)carbonyl)methyl)amide

EXAMPLE 248

5-(n-Hexyloxymethyl)-3-methoxypyridine-2-carboxylic acid N-(((1-octyloxy)carbonyl)methyl)amide

EXAMPLE 249

5-(n-Octyloxymethyl)-3-methoxypyridine-2-carboxylic acid N-(((1-hexyloxy)carbonyl)methyl)amide

EXAMPLE 250

5-((1-Hex-3-enyloxy)methyl)-3-methoxypyridine-2-carboxylic acid N-(((1-octyloxy)carbonyl)methyl)amide

EXAMPLE 251

5-(n-Decyloxymethyl)-3-methoxypyridine-2-carboxylic acid N-(((1-butyloxy)carbonyl)methyl)amide

EXAMPLE 252

5-(n-Dodecyloxymethyl)-3-methoxypyridine-2-carboxylic acid N-(((1-butyloxy) carbonyl)methyl)amide

EXAMPLE 253

3-(4-((+)-Dehydroabietylamino)carbonyl)benzyloxy)pyridine-2-carboxylic acid N-((ethylcarbonyl)methyl)amide m.p. approximately 80° C. (amorphous substance, from ethyl acetate)

EXAMPLE 254

N-(3-Benzyloxypyridyl-2-carbonyl)alanine ethyl ester racemate
$^1$H NMR (CDCl$_3$): δ=5.13 (s, CH$_2$)

EXAMPLE 255

N-(3-Benzyloxypyridyl-2-carbonyl)-L-phenylalanine tert-butyl ester
$^1$H NMR (CDCl$_3$): δ=5.12 (s, CH$_2$)

EXAMPLE 256

N-(3-Benzyloxypyridyl-2-carbonyl)glycine methyl ester, m.p. 81°–82° C. (from ethyl acetate).

EXAMPLE 257

5-((1-Butyloxy)carbonyl)-3-methoxypyridine-2-carboxylic acid N-((tert-butyloxycarbonyl)methyl)amide a) Di-(1-butyl) 3-methoxypyridine-2,5-dicarboxylate 5.0 g of dimethyl 3-methoxypyridine-2,5-dicarboxylate (cf. Example 90a)) were dissolved in 100 ml of 1-butanol, and after that 1.5 ml of conc. sulfuric acid were added and the mixture was heated to boiling for 2 h, with a part of the solvent being distilled off. After the mixture had been cooled, it was concentrated in vacuo and the residue was taken up in dichloromethane; this solution was extracted with a saturated, aqueous solution of Na bicarbonate and the organic phase was dried and concentrated. 6 g of oily crude product.

b) Bis[5-((1-butyloxy)carbonyl)-3-methoxypyridine-2-carboxylic acid]-Cu(II) complex 6 g (20 mmol) of the above oily product were added, dissolved in 10 ml of methanol, to a solution of 4.8 g (20 mmol) of Cu(II) nitrate×3 H$_2$O in 100 ml of methanol, and the mixture was heated to boiling for 4 h. It was then cooled down to 0°–5 C. and the crystalline precipitate was filtered off with suction and washed with diethyl ether. 4.2 g of blue-greenish product were obtained, m.p. 267° C. (with decomposition).

c) 5-((1-Butyloxy)carbonyl)-3-methoxypyridine-2-carboxylic acid 4 g of the above Cu complex were suspended in 75 ml of 1,4-dioxane. H$_2$S gas was passed in, while the mixture was being stirred, for 30 min, and the sediment (CuS) which had precipitated out was filtered off with suction through kieselguhr and then washed with 1,4-dioxane (continued introduction of H$_2$S did not lead to any further precipitation); the filtrate was concentrated in vacuo. The residue was crystallized using petroleum ether, m.p. 96°–98° C.

d) The title compound was obtained by condensing 0.76 g (3 mmol) of the above pyridinecarboxylic acid with 0.52 g (3 mmol) of glycine tert-butyl ester hydrochloride, 1.2 ml (9mmol) of N-ethylmorpholine, 0.45 g (3.3 mmol) of 1-hydroxy-1H-benzotriazole and 1.3 g (3 mmol) of CMC. 0.8 g of colorless crystalline product was obtained, m.p. 50°–52° C. (from petroleum ether).

EXAMPLE 258

5-((1-Butyloxy)carbonyl)-3-methoxypyridine-2-carboxylic acid N-(((1-butyloxy)carbonyl)methyl)amide The title compound was prepared from the pyridine-2-carboxylic acid described in Example 257c) by condensation with glycine 1-butyl ester tosylate, m.p. 80°–81° C. (from petroleum ether).

EXAMPLE 259

5-((1-Hexyloxy)carbonyl)-3-methoxypyridine-2-carboxylic acid N-(((1-butyloxy) carbonyl)methyl)amide a) Bis[5-((1-hexyloxycarbonyl)-3-methoxypyridine-2-carboxylic acid]-Cu (II) complex 6.6 g (18 mmol) of di-(1-hexyl) 3-methoxypyridine-2,5-dicarboxylate (obtained in analogy with Ex. 257a) by acid-catalyzed transesterification using 1-hexanol) were reacted in analogy with Ex. 257b). 4.6 g of Cu(II) complex were obtained, m.p. 265° C. (decomp., washed with diethyl ether).

b) 5-((1-Hexyloxy)carbonyl)-3-methoxypyridine-2-carboxylic acid was obtained, in analogy with Example 257c), from the above Cu(II) complex; 3.4 g, m.p. 108°–110° C. (from petroleum ether).

c) The title compound was obtained from 0.71 g (2.5 mmol) of the above acid and 0.76 g (2.5 mmol) of glycine 1-butyl ester tosylate using N-ethyl morpholine, 1-hydroxy-1H-benzotriazole and CMC. 0.81 g of the product was isolated, m.p. 53°–55° C. (from petroleum ether).

Examples 260 to 287 were obtained in an analogous manner to Examples 257 to 260.

EXAMPLE 260

5-((1-Butyloxy)carbonyl)-3-methoxypyridine-2-carboxylic acid N-((ethyloxycarbonyl)methyl)amide

EXAMPLE 261

5-((1-Hexyloxy)carbonyl)-3-methoxypyridine-2-carboxylic acid N-((ethyloxycarbonyl)methyl)amide

EXAMPLE 262

3-Methoxy-5-((1-pentyloxy)carbonyl)pyridine-3-carboxylic acid-N-((ethyloxycarbonyl)methyl)amide

EXAMPLE 263

5-((1-Heptyloxy)carbonyl)-3-methoxypyridine-2-carboxylic acid N-((ethyloxycarbonyl)methyl)amide

EXAMPLE 264

3-Methoxy-5-((1-octyloxy)carbonyl)pyridine-2-carboxylic acid-N-((ethyloxycarbonyl)methyl)amide

EXAMPLE 265

5-(Ethyloxycarbonyl)-3-methoxypyridine-2-carboxylic acid N-(((1-butyloxy)carbonyl)methyl)amide

EXAMPLE 266

5-(Ethyloxycarbonyl)-3-methoxypyridine-2-carboxylic acid N-((ethyloxy)carbonyl)methyl)amide

EXAMPLE 267

3-Methoxy-5-((1-propyloxy)carbonyl)pyridine-2-carboxylic acid N-((ethyloxycarbonyl)methyl)amide

EXAMPLE 268

3-Methoxy-5-((1-pentyloxy)carbonyl)pyridine-2-carboxylic acid N-(((1-butyloxy)carbonyl)methyl)amide

EXAMPLE 269

5-((1-Heptyloxy)carbonyl)-3-methoxypyridine-2-carboxylic acid N-(((1-butyloxy)carbonyl)methyl)amide

EXAMPLE 270

3-Methoxy-5-((1-octyloxy)carbonyl)pyridine-2-carboxylic acid N-(((1-butyloxy)carbonyl)methyl)amide

EXAMPLE 271

5-(Ethyloxycarbonyl)-3-methoxypyridine-2-carboxylic acid N-(((1-hexyloxy)carbonyl)methyl)amide

EXAMPLE 272

5-((1-Butyloxycarbonyl)-3-methoxypyridine-2-carboxylic acid N-(((1-hexyloxy)carbonyl)methyl)amide

EXAMPLE 273

5-((1-Hexyloxycarbonyl)-3-methoxypyridine-2-carboxylic acid N-(((1-hexyloxy)carbonyl)methyl)amide

EXAMPLE 274

3-Methoxy-5-((1-pentyloxy)carbonyl)pyridine-2-carboxylic acid N-(((1-hexyloxy) carbonyl)methyl)amide

EXAMPLE 275

5-((1-Heptyloxy)carbonyl)-3-methoxypyridine-2-carboxylic acid N-(((1-hexyloxy)carbonyl)methyl)amide

EXAMPLE 276

3-Methoxy-5-((1-octyloxy)carbonyl)pyridine-2-carboxylic acid N-(((1-hexyloxy)carbonyl)methyl)amide

EXAMPLE 277

5-((1-Butyloxy)carbonyl)-3-methoxypyridine-2-carboxylic acid N-(((1-octyloxy)carbonyl)methyl)amide

EXAMPLE 278

5-((1-Hexyloxy)carbonyl)-3-methoxypyridine-2-carboxylic acid N-(((1-octyloxy)carbonyl)methyl)amide

EXAMPLE 279

3-Methoxy-5-((1-pentyloxy)carbonyl)pyridine-2-carboxylic acid N-(((1-octyloxy)carbonyl)methyl)amide

EXAMPLE 280

5-((1-Heptyloxy)carbonyl)-3-methoxypyridine-2-carboxylic acid N-(((1-octyloxy)carbonyl)methyl)amide

EXAMPLE 281

3-Methoxy-5-((1-octyloxy)carbonyl)pyridine-2-carboxylic acid N-(((1-octyloxy)carbonyl)methyl)amide

EXAMPLE 282

5-(Ethyloxycarbonyl)-3-(2-propyloxy)pyridine-2-carboxylic acid N-(((1-butyloxy)carbonyl)methyl)amide

EXAMPLE 283

5-((1-Butyloxy)carbonyl)-3-(2-propyloxy)pyridine-2-carboxylic acid N-(((1-butyloxy)carbonyl)methyl)amide

EXAMPLE 284

5-((1-Hexyloxy)carbonyl)-3-(2-propyloxy)pyridine-2-carboxylic acid N-(((1-butyloxy)carbonyl)methyl)amide

EXAMPLE 285

5-((1-Octyloxy)carbonyl)-3-(2-propyloxy)pyridine-2-carboxylic acid N-(((1-propyloxy)carbonyl)methyl)amide

EXAMPLE 286

5-((1-Octyloxy)carbonyl)-3-(2-propyloxy)pyridine-2-carboxylic acid N-(((1-butyloxy)carbonyl)methyl)amide

EXAMPLE 287

5-((1-Octyloxy)carbonyl)-3-(2-propyloxy)pyridine-2-carboxylic acid N-(((1-hexyloxy)carbonyl)methyl)amide

EXAMPLE 288

5-Methoxycarbonyl-3-(methylthio)pyridine-2-carboxylic acid N-(((1-butyloxy)carbonyl)methyl)amide a) 3-(Methylthio)pyridine-2,5-dicarboxylic acid 4.6 g (12 mmol) of dibenzyl 3-chloropyridine-2,5-dicarboxylate were dissolved, at 20° C. and while stirring, in 30 ml of dimethyl sulfoxide, and after that 5.0 g (70 mmol) of sodium thiomethoxide were added, in association with which the temperature rose to 80° C. The reaction mixture was heated at 140° C. for 1 h and then cooled down, after which water was added to it; the oily layer was separated off and cone. hydrochloric acid (pH 1) was added to the aqueous DMSO phase, and the precipitated product was filtered off with suction. 2.8 g of yellow crystalline product were obtained, m.p. 223° C. (with decomposition).

b) Dimethyl 3-(methylthio)pyridine-2,5-dicarboxylate 50 ml of 1,4-dioxane, 40 ml of tetrahydrofuran and 0.5 ml of conc. sulfuric acid were added to 2.8 g of the above compound in 150 ml of methanol and the mixture was heated to reflux for 2 h, in association with which a solution was produced. After this solution had been cooled down, it was concentrated in vacuo and 100 ml of an aqueous solution of Na bicarbonate were added to the residue; this mixture was extracted with dichloromethane and the organic phase was dried and concentrated. 1.4 g of the Fellow, crystalline product were obtained, m.p. 103°–105° C.

c) 5-Methoxycarbonyl-3-(methylthio)pyridine-2-carboxylic acid-Cu(II) complex 1.3 g of the above dimethyl 3-(methylthio)pyridine-2,5-dicarboxylate were reacted in analogy with Example 257b). 1.3 g of greenish/crystalline product were obtained, m.p. >330° C.

d) 5-Methoxycarbonyl-3-(methylthio)pyridine-2-carboxylic acid 1.3 g of the above compound were reacted in analogy with Example 257c); 0.72 g of product, m.p. 183°–185° C.

e) The title compound was obtained by condensing 0.68 g (3 mmol) of the above pyridinecarboxylic acid with 0.91 g (3 mmol) of glycine 1-butyl ester tosylate (1-hydroxy-(1H)-benzotriazole, N-ethylmorpholine and CMC). 0.57 g of pale yellow product was obtained, m.p. 47°–49° C. (from petroleum ether).

EXAMPLE 289

3-Methoxyquinoline-2-carboxylic acid N-((methoxycarbonyl)methyl)amide a) 2-Acetyl-3-hydroxyquinoline, known from D. W. Bayne et al., J. Chem. Soc. Chem. Comm. 1975, 782, m.p. 106° C. (from aqueous hydrochloric acid).

b) 2-Acetyl-3-methoxyquinoline using potassium carbonate/methyl iodide in acetone from a); oily crude product.

c) 3-Methoxyquinoline-2-carboxylic acid using potassium hypochlorite in water/dioxane from b); m.p. 123° C. (from methyl tert-butyl ether).

d) The title compound was obtained from c) using DCC, HOBT, THF, NEM and glycine methyl ester hydrochloride; $^1$H NMR (DMSO): δ=4.08 (d, CH$_2$-glycine).

We claim:

1. A compound of the formula I

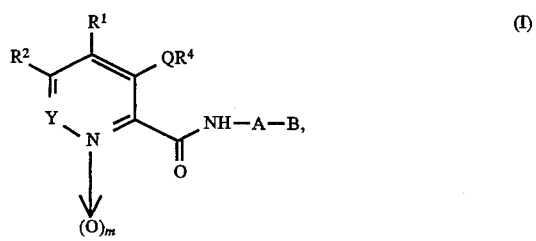

in which

Q is O, S, NR' or a bond,

X is O or S,

Y is CR$^3$, m is 0 or 1,

A is (C$_1$–C$_3$)-alkylene which is optionally substituted once by halogen, cyano, trifluoromethyl, (C$_1$–C$_6$)-alkyl, (C$_1$–C$_6$)-hydroxyalkyl, (C$_1$–C$_6$)-alkoxy or —O—[CH$_2$]$_x$—C$_f$H$_{(2f+1-g)}$F$_g$ or alternatively, A is —CH R$^5$—, where R$^5$ differs from said substituent recited above for A and is a substituent of the α-carbon atom of an α-amino acid, said α-amino acid being a natural L-amino acid or its D-isomer, B is CO$_2$G or a carboxyl radical, G is the radical of an alcohol G—OH, in which G is selected from:

a (C$_1$–C$_{20}$)-alkyl radical, a (C$_3$–C$_8$) cycloalkyl radical, a (C$_2$–C$_{20}$)-alkenyl radical, a (C$_3$–C$_8$) cycloalkenyl radical, a retinyl radical, a (C$_2$–C$_{20}$)-alkynyl radical, a (C$_4$–C$_{20}$)-alkenynyl radical, where the alkenyl, cycloalkenyl, alkynyl, and alkenynyl radicals in each case contain one or more multiple bonds, a (C$_6$–C$_{16}$)-carbocyclic aryl radical, a (C$_7$–C$_{16}$)-carbocyclic aralkyl radical, a heteroaryl radical, and a heteroaralkyl radical, wherein said heteroaryl radical or said heteroaryl moiety of said heteroaralkyl radical contains 5 or 6 ring atoms, wherein the above radicals defined for G are substituted by one or more substituents selected from hydroxyl, halogen, cyano, trifluoromethyl, nitro, carboxyl, (C$_1$–C$_{12}$)-alkyl, (C$_3$–C$_8$)-cycloalkyl, (C$_5$–C$_8$)-cycloalkenyl, (C$_6$–C$_{12}$)-aryl, (C$_7$–C$_{16}$)-aralkyl, ($C_2-C_{12}$)-alkenyl, ($C_2-C_{12}$)-alkynyl, ($C_1-C_{12}$)-alkoxy, ($C_1-C_{12}$)-alkoxy-($C_1-C_{12}$)alkyl, ($C_1-C_{12}$)-alkoxy-($C_1-C_{12}$)alkoxy, ($C_6-C_{12}$)-aryloxy, ($C_7-C_{16}$)-aralkyloxy, ($C_1-C_8$)-hydroxyalkyl, —O—[$CH_2$]$_x$—$C_fH_{(2f+1-g)}(F_g$, —$OCF_2Cl$, —$OCF_2$—CHFCl, ($C_1-C_{12}$)-alkylcarbonyl, ($C_3-C_8$)-cycloalkylcarbonyl, ($C_6-C_{12}$)-arylcarbonyl, ($C_7-C_{16}$)-aralkylcarbonyl, cinnamoyl, ($C_2-C_{12}$)-alkenylcarbonyl, ($C_2-C_{12}$)-alkynylcarbonyl, ($C_1-C_{12}$)-alkoxycarbonyl, ($C_1-C_{12}$)-alkoxy-($C_1-C_{12}$)-alkoxycarbonyl, ($C_6-C_{12}$)-aryloxycarbonyl, ($C_7-C_{16}$)-aralkoxycarbonyl, ($C_3-C_8$)-cycloalkoxycarbonyl, ($C_2-C_{12}$)-alkenyloxycarbonyl, ($C_2-C_{12}$)-alkynyloxycarbonyl, acyloxy, ($C_1-C_{12}$)-alkoxycarbonyloxy, ($C_1-C_{12}$)-alkoxy-($C_1-C_{12}$)-alkoxycarbonyloxy, ($C_6-C_{12}$)-aryloxycarbonyloxy, ($C_7-C_{16}$) aralkyloxycarbonyloxy, ($C_3-C_8$)-cycloalkoxycarbonyloxy, ($C_2-C_{12}$)-alkenyloxycarbonyloxy, ($C_2-C_{12}$)-alkynyloxycarbonyloxy, carbamoyl, N-($C_1-C_{12}$)-alkylcarbamoyl, N,N-di($C_1-C_{12}$)-alkylcarbamoyl, N-($C_3-C_8$)-cycloalkyl-carbamoyl, N-($C_6-C_{16}$)-arylcarbamoyl, N-($C_7-C_{16}$)-aralkylcarbamoyl, N-($C_1-C_{10}$)-alkyl-N-($C_6-C_{16}$)arylcarbamoyl, N-($C_1-C_{10}$)-alkyl-N-($C_7-C_{16}$)-aralkylcarbamoyl, N-(($C_1-C_{10}$)-alkoxy-($C_1-C_{10}$)alkyl)-carbamoyl, N-(($C_6-C_{12}$)-aryloxy-($C_1-C_{10}$)alkyl)carbamoyl, N-(($C_7-C_{16}$)-aralkyloxy-($C_1-C_{10}$)alkyl)carbamoyl, N-($C_1-C_{10}$)-alkyl-N-(($C_1-C_{10}$)-alkoxy-($C_1-C_{10}$)-alkyl)carbamoyl, N-($C_1-C_{10}$)-alkyl-N-(($C_6-C_{16}$)-aryloxy-($C_1-C_{10}$)-alkyl)carbamoyl, N-($C_1-C_{10}$)-alkyl-N-(($C_7-C_{16}$)aralkyloxy-($C_1-C_{10}$)alkyl)carbamoyl, carbamoyloxy, N-($C_1-C_{12}$)-alkylcarbamoyloxy, N,N-di($C_1-C_{12}$)-alkylcarbamoyloxy, N-($C_3-C_8$)-cycloalkylcarbamoyloxy, N-($C_6-C_{12}$)-arylcarbamoyloxy, N-($C_7-C_{16}$)-aralkylcarbamoyloxy, N-($C_1-C_{10}$)-alkyl-N-($C_6-C_{12}$)arylcarbamoyloxy, N($C_1-C_{10}$)-alkyl-N-($C_7-C_{16}$)-aralkylcarbamoyloxy, N-(($C_1-C_{10}$)alkyl)carbamoyloxy, N-(($C_6-C_{12}$)-aryloxy-($C_1-C_{10}$)alkyl)carbamoyloxy, N-(($C_7-C_{16}$)-aralkyloxy-($C_1-C_{10}$)alkyl)carbamoyloxy, N-($C_1-C_{10}$)-alkyl-N-(($C_1-C_{10}$)-alkoxy-($C_1-C_{10}$)-alkyl)carbamoyloxy, N-($C_1-C_{10}$)-alkyl-N-(($C_6-C_{12}$)-aryloxy-($C_1-C_{10}$)-alkyl)carbamoyloxy, N-($C_1-C_{10}$)-alkyl-N-(($C_7-C_{16}$)-aralkyloxy-($C_1-C_{10}$)alkyl)carbamoyloxy, amino, ($C_1-C_{12}$)-alkylamino, di-($C_1-C_{12}$)alkylamino, ($C_3-C_8$)-cycloalkylamino, ($C_2-C_{12}$)-alkenylamino, ($C_2-C_{12}$)-alkynylamino, N-($C_6-C_{12}$)-arylamino, N-($C_7-C_{11}$)-aralkylamino, N-alkyl-aralkylamino, N-alkyl-arylamino, ($C_1-C_{12}$)-alkoxyamino, ($C_1-C_{12}$)-alkoxy-N-($C_1-C_{10}$)-alkylamino, ($C_1-C_{12}$)-alkylcarbonylamino, ($C_3-C_8$)-cycloalkylcarbonyl-amino, ($C_6-C_{12}$) arylcarbonylamino, ($C_7-C_{16}$)-aralkylcarbonylamino, ($C_1-C_{12}$)-alkylcarbonyl-N-($C_1-C_{10}$)-alkylamino, ($C_3-C_8$)-cycloalkylcarbonyl-N-($C_1-C_{10}$)-alkylamino, ($C_6-C_{12}$)-arylcarbonyl-N-($C_1-C_{10}$)alkylamino, ($C_7-C_{11}$)-aralkylcarbonyl-N-($C_1-C_{10}$)-alkylamino, ($C_1-C_{12}$)-alkylcarbonylamino-($C_1-C_8$)-alkyl, ($C_3-C_8$)-cycloalkylcarbonylamino-($C_1-C_8$)alkyl, ($C_6-C_{12}$)-arylcarbonylamino-($C_1-C_8$)-alkyl, ($C_7-C_{12}$)-aralkylcarbonylamino($C_1-C_8$)-alkyl, amino-($C_1-C_{10}$)-alkyl, N-($C_1-C_{10}$) alkylamino-($C_1-C_{10}$)alkyl, N,N-di ($C_1-C_{10}$)-alkylamino-($C_1-C_{10}$)alkyl, ($C_3-C_8$) cycloalkylamino-($C_1-C_{10}$)alkyl, ($C_1-C_{12}$)-alkylmercapto, ($C_1-C_{12}$)-alkylsulfinyl, ($C_1-C_{12}$)-alkylsulfonyl, ($C_6-C_{16}$)-arylmercapto, ($C_6-C_{16}$)-arylsulfinyl, ($C_6-C_{12}$)-arylsulfonyl, ($C_7-C_{16}$)-aralkylmercapto, ($C_7-C_{16}$)-aralkylsulfinyl, ($C_7-C_{16}$)-aralkylsulfonyl, sulfamoyl, N-($C_1-C_{10}$)-alkylsulfamoyl, N,N-di($C_1-C_{10}$)-alkylsulfamoyl, ($C_3-C_8$)-cycloalkylsulfamoyl, N-($C_6-C_{12}$)-alkylsulfamoyl, N-($C_7-C_{16}$)-aralkylsulfamoyl, N-($C_1-C_{10}$)-alkyl-N-($C_6-C_{12}$)-arylsulfamoyl, N-($C_1-C_{10}$)-alkyl-N-($C_7-C_{16}$)-aralkylsulfamoyl, ($C_1-C_{10}$)-alkyl-sulfonamido, N-(($C_1-C_{10}$)alkyl)-($C_1-C_{10}$)alkylsulfonamido, ($C_7-C_{16}$)-aralkylsulfonamido and N-(($C_1-C_{10}$)-alkyl-($C_7-C_{16}$)-aralkylsulfonamido, wherein the radicals which are aryl or which contain an aryl moiety may be substituted on the aryl by from 1 to 5 identical or different radicals selected from:

hydroxyl, halogen, cyano, trifluoromethyl, nitro, carboxyl, ($C_1-C_{12}$)-alkyl, ($C_3-C_8$)-cycloalkyl, ($C_6-C_{12}$)-aryl, ($C_7-C_{16}$)-aralkyl, ($C_1-C_{12}$)-alkoxy, ($C_1-C_{12}$)-alkoxy-($C_1-C_{12}$)alkyl,($C_1-C_{12}$)-alkoxy-($C_1C_{12}$)alkoxy, ($C_6-C_{12}$)-aryloxy, ($C_7-C_{16}$)-aralkyloxy, ($C_1-C_8$)-hydroxyalkyl, ($C_1-C_{12}$)-alkylcarbonyl, ($C_3-C_8$)-cycloalkyl-carbonyl, ($C_6-C_{12}$)-arylcarbonyl, ($C_7-C_{16}$) aralkylcarbonyl, ($C_1-C_{12}$)-alkoxycarbonyl, ($C_1-C_{12}$)-alkoxy-($C_1-C_{12}$)-alkoxycarbonyl, ($C_6-C_{12}$)-aryloxycarbonyl, ($C_7-C_{16}$)-aralkoxycarbonyl, ($C_3-C_8$)-cycloalkoxycarbonyl, ($C_2-C_{12}$)-alkenyloxycarbonyl, ($C_2-C_{12}$)-alkynyloxycarbonyl, ($C_1-C_{12}$)-alkylcarbonyloxy, ($C_3-C_8$)-cycloalkylcarbonyloxy, ($C_6-C_{12}$)-arylcarbonyloxy, ($C_7-C_{16}$)-aralkylcarbonyloxy, cinnamoyloxy, ($C_2-C_{12}$)-alkenylcarbonyloxy, ($C_2-C_{12}$)-alkynylcarbonyloxy, ($C_1-C_{12}$)-alkoxycarbonyloxy, ($C_1-C_{12}$)-alkoxy-($C_1-C_{12}$)-alkoxycarbonyloxy, ($C_6-C_{12}$)-aryloxycarbonyloxy, ($C_7-C_{16}$)-aralkyloxycarbonyloxy, ($C_3-C_8$)-cycloalkoxycarbonyloxy, ($C_2-C_{12}$)-alkenyloxycarbonyloxy, ($C_2-C_{12}$)-alkynyloxycarbonyloxy, carbamoyl, N-($C_1-C_{12}$)-alkylcarbamoyl, N,N-di($C_1-C_{12}$) alkylcarbamoyl, N-($C_3-C_8$)-cycloalkylcarbamoyl, N-($C_6-C_{12}$)-arylcarbamoyl, N-($C_7-C_{16}$)-aralkylcarbamoyl, N-($C_1-C_{10}$)-alkyl-N-($C_6-C_{12}$)-arylcarbamoyl, N-($C_1-C_{10}$)-alkyl-N-($C_7-C_{16}$)-aralkylcarbamoyl, N-(($C_1-C_{10}$)-alkoxy-($C_1-C_{10}$)alkyl) carbamoyl, N-(($C_6-C_{12}$)-aryloxy-($C_1-C_{10}$)alkyl) carbamoyl, N-(($C_7-C_{16}$)-aralkyloxy-($C_1-C_{10}$)alkyl) carbamoyl, N-($C_1-C_{10}$)-alkyl-N-(($C_1-C_{10}$)-alkoxy-($C_1-C_{10}$)-alkyl) carbamoyl, N-($C_1-C_{10}$)-alkyl-N-(($C_6-C_{12}$)-aryloxy-($C_1-C_{10}$)-alkyl)carbamoyl, N-($C_1-C_{10}$)-alkyl-N-(($C_7-C_{16}$)aralkyloxy-($C_1-C_{10}$)alkyl)carbamoyl, carbamoyloxy, N-($C_1-C_{12}$)-alkylcarbamoyloxy, N,N-di-($C_1-C_{12}$)-alkylcarbamoyloxy, N-($C_3-C_8$)-cycloalkylcarbamoyloxy, N-($C_6-C_{12}$)-arylcarbamoyloxy, N-($C_7-C_{16}$)-aralkylcarbamoyloxy, N-($C_1-C_{10}$)-alkyl-N-($C_6-C_{12}$)-arylcarbamoyloxy, N($C_1-C_{10}$)-alkyl-N-($C_7-C_{16}$)-aralkylcarbamoyloxy, N-(($C_1-C_{10}$)alkyl)carbamoyloxy, N-(($C_6-C_{12}$)-aryloxy-($C_1-C_{10}$)alkyl)-carbamoyloxy, N-(($C_7-C_{16}$)-aralkyloxy-($C_1-C_{10}$)alkyl)carbamoyloxy, N-($C_1-C_{10}$)-alkyl-N-(($C_1-C_{10}$)-alkoxy-($C_1-C_{10}$)-alkyl) carbamoyloxy, N-($C_1-C_{10}$)-alkyl-N-(($C_6-C_{12}$)-aryloxy-($C_1-C_{10}$)-alkyl)carbamoyloxy, N-($C_1-C_{10}$)- alkyl-N-((C$_7$–C$_{16}$)-aralkyloxy-(C$_1$–C$_{10}$)alkyl) carbamoyloxy, amino, (C$_1$–C$_{12}$)-alkylamino, di-(C$_1$–C$_{12}$)alkylamino, (C$_3$–C$_8$)-cycloalkylamino, (C$_3$–C$_{12}$)-alkenylamino, (C$_3$–C$_{12}$)-alkynylamino, N-(C$_6$–C$_{12}$)-arylamino, N-(C$_7$–C$_{11}$)-aralkylamino, N-alkylaralkylamino, N-alkyl-arylamino, (C$_1$–C$_{12}$)-alkoxyamino, (C$_1$–C$_{12}$)-alkoxy-N-(C$_1$–C$_{10}$)-alkylamino, (C$_1$–C$_{12}$)-alkylcarbonylamino, (C$_3$–C$_8$)-cycloalkylcarbonylamino, (C$_6$–C$_{12}$)-arylcarbonylamino, (C$_7$–C$_{16}$)-alkylcarbonylamino, (C$_1$–C$_{12}$)-alkylcarbonyl-N-(C$_1$–C$_{10}$)-alkylamino, (C$_3$–C$_8$)-cycloalkylcarbonyl-N-(C$_1$–C$_{10}$)-alkylamino, (C$_6$–C$_{12}$)-arylcarbonyl-N-(C$_1$–C$_{10}$)alkylamino, (C$_7$–C$_{11}$)-aralkylcarbonyl-N-(C$_1$–C$_{10}$)-alkylamino, (C$_1$–C$_{12}$)-alkylcarbonylamino-(C$_1$–C$_8$)-alkyl, (C$_3$–C$_8$)-cycloalkylcarbonylamino-(C$_1$–C$_8$)alkyl, (C$_6$–C$_{12}$)-arylcarbonylamino-(C$_1$–C$_8$)-alkyl, (C$_7$–C$_{16}$)-aralkylcarbonylamino-(C$_1$–C$_8$)-alkyl, amino-(C$_1$–C$_{10}$)-alkyl, N-(C$_1$–C$_{10}$)alkylamino-(C$_1$–C$_{10}$)alkyl, N,N-di(C$_1$–C$_{10}$)-alkylamino-(C$_1$–C$_{10}$)alkyl, (C$_3$–C$_8$)-cycloalkylamino-(C$_1$–C$_{10}$)alkyl, (C$_1$–C$_{12}$)-alkylmercapto, (C$_1$–C$_{12}$)-alkylsulfinyl, (C$_1$–C$_{12}$)-alkylsulfonyl, (C$_6$–C$_{12}$)-arylmercapto, (C$_6$–C$_{12}$)-arylsulfinyl, (C$_6$–C$_{12}$)-arylsulfonyl, (C$_7$–C$_{16}$)-aralkylmercapto, (C$_7$–C$_{16}$)-aralkylsulfinyl and (C$_7$–C$_{16}$)-aralkylsulfonyl, R$^1$ and R$^3$ are identical or different and are hydrogen, halogen, (C$_1$–C$_{20}$)-alkyl, (C$_2$–C$_{20}$)-alkenyl, (C$_1$–C$_{12}$)-alkoxy, —O—[CH$_2$]$_x$—C$_f$H$_{(2f+1-g)}$Hal$_g$, (C$_1$–C$_{12}$)-alkoxy-(C$_1$–C$_{12}$)-alkyl, (C$_1$–C$_8$)-alkoxy-(C$_1$–C$_{12}$)-alkoxy, (C$_1$–C$_{12}$)-alkoxy-(C$_1$–C$_8$)-alkoxy-(C$_2$–C$_6$)-alkyl, (C$_7$–C$_{11}$)-aralkyloxy, (C$_3$–C$_8$)-cycloalkyl, (C$_3$–C$_6$)-cycloalkyl-(C$_1$–C$_8$)-alkyl, (C$_3$–C$_8$)-cycloalkyloxy, (C$_3$–C$_8$)-cycloalkyl-(C$_1$–C$_8$)-alkoxy, (C$_3$–C$_8$)-cycloalkyloxy-(C$_1$–C$_8$)-alkyl, (C$_3$–C$_8$)-cycloalkyloxy-(C$_1$–C$_8$)-alkoxy, (C$_3$–C$_8$) cycloalkyl-(C$_1$–C$_6$)-alkyl-(C$_1$–C$_6$)-alkoxy, (C$_3$–C$_8$)-cycloalkyl-(C$_1$–C$_6$)-alkoxy-(C$_1$–C$_6$)-alkyl, (C$_3$–C$_8$)-cycloalkoxy-(C$_1$–C$_6$)-alkoxy-(C$_1$–C$_6$)-alkyl, NR$^Y$R$^Z$, (C$_1$–C$_8$)-alkylmercapto, (C$_1$–C$_8$)-alkylsulfinyl, (C$_1$–C$_8$)-alkysulfonyl, (C$_6$–C$_{12}$)-arylmercapto, (C$_6$–C$_{12}$)-arylsulfinyl, (C$_6$–C$_{12}$)-arylsulfonyl, (C$_7$–C$_{12}$)-aralkylmercapto, (C$_7$–C$_{12}$)-aralkylsulfinyl, (C$_7$–C$_{11}$)-aralkylsulfonyl, substituted (C$_6$–C$_{12}$)-aryloxy-(C$_1$–C$_6$)-alkyl, (C$_7$–C$_{11}$)-aralkyloxy-(C$_1$–C$_6$)-alkyl, (C$_6$–C$_{12}$)-aryloxy-(C$_1$–C$_6$)-alkoxy-(C$_1$–C$_6$)-alkyl, (C$_7$–C$_{11}$)-aralkyloxy-(C$_1$–C$_6$)-alkoxy-(C$_1$–C$_6$)-alkyl, (C$_6$–C$_{12}$)-aryloxy, (C$_7$–C$_{11}$)-aralkyloxy, (C$_6$–C$_{12}$)-aryloxy-(C$_6$–C$_{12}$)-alkoxy or (C$_7$–C$_{11}$)-aralkoxy-(C$_1$–C$_6$)-alkoxy, where the radicals which are aryl or which contain an aryl moiety may be substituted on the aryl by from 1 to 5 identical or different substituents selected from halogen, cyano, nitro, trifluoromethyl, (C$_1$–C$_{12}$)-alkyl, (C$_2$–C$_{12}$)-alkenyl, (C$_1$–C$_6$)-hydroxyalkyl, (C$_1$–C$_{12}$-alkoxy, (C$_2$–C$_{12}$)-alkenyloxy, —O—[CH$_2$]$_x$—C$_f$H$_{(2f+1-g)}$F$_g$, —OCF$_2$Cl, —O—CF$_2$—CHFCl, C$_1$–C$_6$)-alkylmercapto, (C$_1$–C$_6$)-alkylsulfinyl, (C$_1$–C$_6$)-alkylsulfonyl, (C$_1$–C$_6$)-alkylcarbonyl, carbamoyl, N-(C$_1$–C$_4$)-alkylcarbamoyl, N,N-di-(C$_1$–C$_4$)-alkylcarbamoyl, (C$_1$–C$_6$)-alkylcarbonyloxy, (C$_3$–C$_8$)-cycloalkylcarbamoyl, phenyl, benzyl, phenoxy, benzyloxy, NR$^Y$R$^Z$, phenylmercapto, phenylsulfonyl, phenylsulfinyl, sulfamoyl, N-(C$_1$–C$_4$)-alkylsulfamoyl or N,N-di-(C$_1$–C$_4$)-alkylsulfamoyl, or alternatively, in the case where said radicals which are aryl or which contain an aryl moiety are substituted on the aryl by up to 3 of said radicals recited as aryl substitutents above, then two adjacent carbon atoms of an aralkyloxy radical recited in the definition of R$^1$ and R$^3$ together carry at least one chain selected from —[CH$_2$]$_n$— and —CH=CH—CH=CH—, where a CH$_2$ group of the chain is optionally replaced by O, S, SO, SO$_2$ or NR$^Y$, or alternatively R$^3$ is as defined above and R$^1$ and R$^2$ can form a chain —[CH$_2$]$_o$-, where o is 3, 4, or 5, or alternatively R$^1$ is as defined above and R$^2$ and R$^3$ can form a chain —[CH$_2$]$_o$- where o is 3, 4, or 5, or alternatively R$^1$ and R$^2$ or R$^2$ and R$^3$ together with the carbon atoms to which they are attached form a carbocyclic 6-membered ring of either formula Ia or Ib

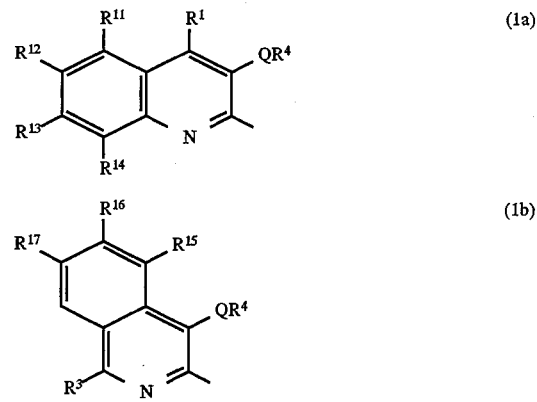

wherein Q and R$^4$ are as defined above for formula (I) and R$^{11}$ to R$^{18}$ are independently as defined above for R$^1$ and R$^3$ R$^2$ is hydrogen, (C$_1$–C$_{20}$)-alkyl, (C$_2$–C$_{20}$)-alkenyl, (C$_2$–C$_{20}$)-alkenyloxy, (C$_2$–C$_{20}$)-alkynyloxy, retinyloxy, (C$_1$–C$_{20}$)-alkoxy-(C$_1$–C$_3$)-alkyl, (C$_1$–C$_{20}$)-alkoxy-(C–C$_3$)-alkyl, (C$_2$–C$_{20}$)-alkenyloxy-(C$_1$–C$_3$)-alkyl, retinyloxy-(C$_1$–C$_3$)-alkyl, (C$_2$–C$_{20}$)-alkynyloxy-(C$_1$–C$_3$)-alkyl, (C$_1$–C$_{20}$)-alkoxy, halogen, cyano, trifluoromethyl, (C$_1$–C$_{16}$)-hydroxyalkyl, (C$_1$–C$_{20}$)-alkylcarbonyl, (C$_7$–C$_{12}$)-aralkylcarbonyl, (C$_6$–C$_{12}$)arylcarbonyl, —O—[CH$_2$]$_x$C$_f$H$_{(2f+1-g)}$F$_g$, NR$^Y$ R$^Z$, C$_1$–C$_{10}$)-alkylmercapto, (C$_1$–C$_{10}$)-alkylsulfinyl, (C$_1$–C$_{10}$)-alkylsulfonyl, (C$_6$–C$_{12}$)-arylmercapto, (C$_6$–C$_{12}$)-arylsulfinyl, (C$_6$–C$_{12}$)-arylsulfonyl, (C$_7$–C$_{12}$)-aralkylmercapto, (C$_7$–C$_{12}$)-aralkylsulfinyl, (C$_7$–C$_{12}$)-aralkylsulfonyl, (C$_6$–C$_{12}$)-aryloxy, (C$_7$–C$_{16}$)-aralkyloxy, carboxyl, (C$_1$–C$_{20}$)-alkoxycarbonyl, (C$_1$–C$_{12}$)-alkoxy-(C$_1$–C$_{12}$)-alkoxycarbonyl, (C$_6$–C$_{12}$)-aryloxycarbonyl, (C$_7$–C$_{16}$)-aralkoxycarbonyl, (C$_3$–C$_8$)-cycloalkoxycarbonyl, (C$_2$–C$_{20}$)-alkenyloxycarbonyl, retinyl-oxycarbonyl, (C$_2$–C$_{20}$)-alkynyloxycarbonyl, (C$_3$–C$_8$)-cycloalkyl-(C$_1$–C$_6$)-alkoxycarbonyl, (C$_3$–C$_8$)-cycloalkoxy-(C$_1$–C$_6$)-alkoxycarbonyl, (C$_6$–C$_{12}$)-aryloxy-(C$_1$–C$_6$)-alkoxycarbonyl, (C$_7$–C$_{16}$)-aralkoxy-(C$_1$–C$_6$)-alkoxycarbonyl, carbamoyl, N-(C$_1$–C$_{12}$)-alkylcarbamoyl, N,N-di-(C$_1$–C$_{12}$)-alkylcarbamoyl, N-(C$_3$–C$_8$)-cycloalkylcarbamoyl-N,N-dicyclo(C$_3$–C$_8$)-alkylcarbamoyl, N-(C$_1$–C$_{10}$)-alkyl-N-(C$_3$–C$_8$)-cycloalkylcarbamoyl, N-((C$_3$–C$_8$)-cycloalkyl-(C$_1$–C$_6$)-alkyl)carbamoyl, N-(C$_1$–C$_6$)-alkyl-N-((C$_3$–C$_8$)-cycloalkyl-(C$_1$–C$_6$)-alkyl)carbamoyl, N-(+)-dehydroabietylcarbamoyl, N-(C$_1$–C$_6$)alkyl-N-(+)-dehydroabietylcarbamoyl, N-(C$_6$–C$_{12}$)-arylcarbamoyl, N-(C$_7$–C$_{16}$)-aralkylcarbamoyl, N-(C$_1$–C$_{10}$)-alkyl-N-(C$_6$–C$_{16}$)-arylcarbamoyl, N-(C$_1$–C$_{10}$)-alkyl-N-(C$_7$–C$_{12}$-aralkylcarbamoyl, N-((C$_1$–C$_{12}$)-alkoxy-(C$_1$–C$_{10}$)-alkyl)carbamoyl, N-((C$_6$–C$_{16}$)-aryloxy-(C$_1$–C$_{10}$)-alkyl)carbamoyl, N-($C_7$–$C_{16}$)-aralkyloxy-($C_1$–$C_{10}$)-alkyl)carbamoyl, N-($C_1$–$C_{10}$)-alkyl-N-($C_1$–$C_{10}$)-alkoxy-($C_1$–$C_{10}$)-alkyl) carbamoyl, N-($C_1$–$C_{10}$)-alkyl-N-(($C_6$–$C_{12}$)-aryloxy-($C_1$–$C_{10}$)-alkyl)carbamoyl, N-($C_1$–$C_{10}$)-alkyl-N-( ($C_7$–$C_{16}$)-aralkyloxy-($C_1$–$C_{10}$)-alkyl)-carbamoyl, or $CON(CH_2)_h$, in which a $CH_2$ group can be replaced by O, S, N-($C_1$–$C_8$)-alkylimino, N-($C_3$–$C_8$)-cycloalkylimino, N-($C_3$–$C_8$)-cycloalkyl-($C_1$–$C_4$)-alkylimino, N-($C_6$–$C_{12}$)-arylimino, N-($C_7$–$C_{16}$)-aralkylimino or N-($C_1$–$C_4$)-alkoxy-($C_1$–$C_6$)-alkylimino, wherein the aryl moieties and aryl radicals defined herein for $R^2$ may be substituted in the manner defined for $R^1$ and $R^3$, $R^4$, if Q is a bond, is chlorine or, if Q is O, S, or NR', is a ($C_1$–$C_{10}$)-alkyl radical, a ($C_2$–$C_{10}$)-alkenyl radical, a ($C_2$–$C_{10}$)-alkynyl radical, wherein said alkenyl or alkynyl radical contains one or two C—C multiple bonds, an unsubstituted fluoroalkyl radical of the formula —$[CH_2]_x$—$C_fH_{(2f+1-g)}F_g$, a ($C_1$–$C_8$)-alkoxy-($C_1$–$C_6$)-alkyl radical, a ($C_1$–$C_6$)-alkoxy-($C_1$–$C_4$)-alkoxy-($C_1$–$C_4$)-alkyl radical or a radical of the formula Z,

where E is a heteroaryl radical, a ($C_3$–$C_8$)-cycloalkyl radical, or a phenyl radical of the formula F

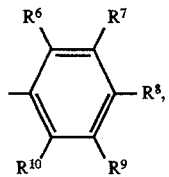

wherein v is 0, 1, 2, 3, 4, 5 or 6, w is 0 or 1, and t is 0, 1, 2 or 3, with the restriction that v is not 0 if w is 1, and $R^6$, $R^7$, $R^8$, $R^9$ and $R^{10}$ are identical or different and are selected from hydrogen, halogen, cyano, nitro, trifluoromethyl, ($C_1$–$C_6$)-alkyl, ($C_3$–$C_8$)-cycloalkyl, ($C_1$–$C_6$)-alkoxy, —O—$[CH_2]_x$—$C_fH_{(2f+1-g)}F_g$, —$OCF_2Cl$, —O—$CF_2CHFCl$, ($C_1$–$C_6$)-alkylmercapto, ($C_1$–$C_6$)-hydroxyalkyl, ($C_1$–$C_6$)-alkoxy-($C_1$–$C_6$)-alkoxy, ($C_1$–$C_6$)-alkoxy-($C_1$–$C_6$)-alkyl, ($C_1$–$C_6$)-alkylsulfinyl, ($C_1$–$C_6$)-alkylsulfonyl, ($C_1$–$C_6$)-alkylcarbonyl, ($C_1$–$C_8$)-alkoxycarbonyl, carbamoyl, N-($C_1$–$C_8$)-alkylcarbamoyl, N,N-di-($C_1$–$C_8$)-alkylcarbamoyl, ($C_7$–$C_{11}$)-aralkylcarbamoyl optionally substituted by fluorine, chlorine, bromine, trifluoromethyl or ($C_1$–$C_6$)-alkoxy, N-($C_3$–$C_8$)-cycloalkylcarbamoyl, N-($C_3$–$C_8$)-cycloalkyl-($C_1$–$C_4$)-alkylcarbamoyl, ($C_1$–$C_6$)-alkylcarbonyloxy, phenyl, benzyl, phenoxy, benzyloxy, $NR^YR^Z$, phenylmercapto, phenylsulfonyl, phenylsulfinyl, sulfamoyl, N-($C_1$–$C_8$)-alkylsulfamoyl or N, N-di-($C_1$–$C_8$)-alkylsulfamoyl, or alternatively $R^6$ and $R^7$, $R^7$ and $R^8$, $R^8$ and $R^9$, or $R^9$ and $R^{10}$ together are a chain selected from —$[CH_2]_n$- and —CH=CH—CH=CH—, where a $CH_2$ group of the chain is optionally replaced by O, S, SO, $SO_2$ or $NR^Y$, and if E is said heteroaryl radical, said radical can carry 1, 2 or 3 substituents selected from those defined herein for $R^6$–$R^{10}$ or if E is said cycloalkyl radical, said radical can carry one substituent selected from those defined herein for $R^6$–$R^{10}$, or alternatively, $R^4$ is R", provided Q has the meaning of NR', where R' and R" are identical or different and are hydrogen, ($C_6$–$C_{12}$)-aryl, ($C_7$–$C_{11}$)-aralkyl, ($C_1$–$C_8$)-alkyl, ($C_1$–$C_8$)-alkoxy-($C_1$–$C_8$)-alkyl, ($C_7$–$C_{12}$)-aralkoxy-($C_1$–$C_8$)-alkyl, ($C_6$–$C_{12}$)-aryloxy-($C_1$–$C_8$)-alkyl, ($C_1$–$C_{10}$)-alkylcarbonyl, optionally substituted ($C_7$–$C_{16}$)-aralkylcarbonyl or optionally substituted $C_6$–$C_{12}$)-arylcarbonyl, or R' and R" together are —$[CH_2]_h$, in which a $CH_2$ group can be replaced by O, S, N-acylimino or N-($C_1$–$C_{10}$)-alkoxycarbonylimino or alternatively, $R^2$ is as defined above, and at least one of $R^1$ and $R^3$, which are identical or different, is selected from a radical of the formula (D)

$$OZ \qquad (D),$$

wherein Z is as defined above for $R^4$, and if one of $R^1$ and $R^3$ is not (D), said one is as defined above, or alternatively $R^2$ is as defined above and $R^1$ and $R^3$ are identical or different and are selected from a radical of the formula Z, wherein Z is as defined above for $R^4$, $R^Y$ and $R^Z$ are identical or different and are hydrogen, ($C_6$–$C_{12}$)-aryl, ($C_1$–$C_{10}$)-alkyl, ($C_3$—$C_{10}$)-cycloalkyl, ($C_1$–$C_8$)-alkoxy-($C_1$–$C_8$)-alkyl, ($C_7$–$C_{12}$)-aralkoxy-($C_1$–$C_8$)-alkyl, ($C_6$–$C_{12}$)-aryloxy-($C_1$–$C_8$)-alkyl, ($C_1$–$C_{10}$)-alkylcarbonyl, optionally substituted ($C_7$–$C_{16}$)-aralkylcarbonyl or optionally substituted ($C_6$–$C_{12}$)-arylcarbonyl, or alternatively $R^Y$ and $R^Z$ are together —$[CH_2]_h$-, in which a $CH_2$ group can be replaced by O, S, N-($C_1$–$C_4$)-alkylcarbonylimino or N-($C_1$–$C_4$)-alkoxycarbonylimino, f is 1 to 8, g is 0 or 1 to (2f+1), h is 3 to 6, x is 0 to 3, and n is 3 or 4, or a physiologically active salt thereof, with the proviso that 3-benzyloxypyridine-2-carboxylic acid (L-threonyl methyl ester) amide, 3-benzyloxy-pyridine-2-carboxylic acid (L-threonyl (Fmoc-Phg) tert-butyl ester) amide, 3-benzyloxy-pyridine-2-carboxylic acid (L-threonyl tertbutyl ester) amide, 3-benzyloxypyridine-2-carboxylic acid (D-allothreonyl methyl ester) amide, 3-benzyloxy-pyridine-2-carboxylic acid (glycyl ethyl ester) amide, 3-benzyloxypyridine-2-carboxylic acid (L-threonyl) amide, 3-benzyloxypyridine-2-carboxylic acid, and 3-benzyloxypyridine-2-carboxylic acid ((Fmoc-Phg) L-threonyl) amide hydrochloride are excluded.

2. A compound of the formula I or a physiologically active salt thereof according to claim 1, wherein G is selected from a ($C_1$–$C_{20}$)-alkyl radical, a ($C_3$–$C_8$)-cycloalkyl radical, a retinyl radical, a ($C_2$–$C_{20}$)-alkenyl radical, a ($C_2$–$C_{20}$) -alkynyl radical, wherein said alkenyl or alkynyl radical contains one or more C—C multiple bonds, a ($C_6$–$C_{12}$)-carbocyclic aryl radical, a ($C_7$–$C_{11}$)-carbocyclic aralkyl radical, a heteroaryl radical, and a heteroaralkyl radical, wherein said heteroaryl radical or said heteroaryl moiety of said heteroaralkyl radical contains 5 or 6 ring atoms, wherein the above radicals defined for G are substituted by one or two substituents selected from ($C_1$–$C_8$)-alkyl, ($C_3$–$C_8$)-cycloalkyl, fluorine, chlorine, hydroxyl, ($C_1$–$C_6$)-alkoxy, ($C_1$–$C_6$)-alkoxy-($C_1$–$C_6$)-alkoxy, ($C_6$–$C_{12}$)-aryloxy, ($C_7$–$C_{12}$)-aralkyloxy, ($C_1$–$C_8$)-alkylcarbonyl, ($C_3$–$C_8$)-cycloalkylcarbonyl, ($C_6$–$C_{12}$)-arylcarbonyl, ($C_7$–$C_{12}$)-aralkylcarbonyl, ($C_1$–$C_8$)-alkoxycarbonyl, ($C_1$–$C_6$)-alkoxy-($C_1$–$C_6$)-alkoxycarbonyl, ($C_6$–$C_{12}$)-aryloxycarbonyl, ($C_7$–$C_{12}$)- aralkoxycarbonyl, $(C_3-C_8)$-cycloalkoxycarbonyl, $(C_1-C_{20})$-alkylcarbonyloxy, $(C_3-C_8)$-cycloalkylcarbonyloxy, $(C_6-C_{12})$-arylcarbonyloxy, $(C_3-C_8)$-aralkylcarbonyloxy, cinnamoyloxy, $(C_2-C_{12})$-alkenylcarbonyloxy, $(C_2-C_{12})$-alkynylcarbonyloxy, $(C_1-C_8)$-alkoxycarbonyloxy, $(C_1-C_6)$-alkoxy-$(C_1-C_6)$-alkoxycarbonyloxy, $(C_6-C_{12})$-aryloxycarbonyloxy, $(C_7-C_{12})$-aralkyloxycarbonyloxy, $(C_3-C_8)$-cycloalkoxycarbonyloxy, carbamoyl, N-$(C_1-C_8)$-alkylcarbamoyl, N,N-di-$(C_1-C_8)$-alkylcarbamoyl, N-$(C_3-C_8)$-cycloalkylcarbamoyl, N-$(C_1-C_6)$-alkoxy-$(C_1-C_6)$alkyl)carbamoyl, amino, $(C_1-C_6)$-alkylamino, di-$(C_1-C_8)$alkylamino, $(C_3-C_8)$-cycloalkylamino, N-$(C_6-C_{12})$-arylamino, N-$(C_7-C_{11})$-aralkylamino, N-$(C_1-C_5)$-alkyl-$(C_6-C_{12}$arylamino, $(C_1-C_8)$-alkylcarbonylamino, $(C_3-C_8)$-cycloalkylcarbonylamino, $(C_6-C_{12})$-arylcarbonylamino, $(C_7-C_{12})$-aralkylcarbonyl-amino, $(C_1-C_8)$-alkylcarbonyl-N-$(C_1-C_6)$-alkylamino, $(C_3-C_8)$-cycloalkylcarbonyl-N-$(C_1-C_6)$-alkylamino, $(C_6-C_{12})$-arylcarbonyl-N-$(C_1-C_6)$-alkylamino and $(C_7-C_{11})$-aralkylcarbonyl-N-$(C_1-C_6)$-alkylamino, wherein said radicals which are aryl or which contain an aryl moiety may be substituted by up to 3 substituents selected from:

hydroxyl, fluorine, chlorine, cyano, trifluoromethyl, $(C_1-C_6$-alkyl, $(C_3-C_8)$-cycloalkyl, $(C_1-C_8$-alkoxy, $(C_1-C_6)$-alkylcarbonyl, $(C_3-C_8)$-cycloalkylcarbonyl, $(C_1-C_6)$-alkoxycarbonyl, $(C_3-C_8)$-cycloalkoxycarbonyl, $(C_1-C_6)$-alkylcarbonyloxy, $(C_3-C_8)$-cycloalkylcarbonyloxy, $(C_1-C_6)$-alkoxycarbonyloxy, $(C_3-C_8)$-cycloalkoxycarbamoyloxy, carbamoyl, N-$(C_1-C_6)$-alkylcarbamoyl, N,N-di$(C_1-C_6)$-alkylcarbamoyl, N-$(C_3-C_8)$-cycloalkylcarbamoyl, N-$(C_1-C_6)$-alkoxy-$(C_1-C_6)$alkyl)carbamoyl, N-$(C_1-C_6)$-alkyl-N-$((C_1-C_6)$-alkoxy-$(C_1-C_6)$alkyl)-carbamoyl, carbamoyloxy, N-$(C_1-C_6)$-alkylcarbamoyloxy, N,N-di-$(C_1-C_6)$-alkylcarbamoyloxy, N-$(C_3-C_8)$-cycloalkylcarbamoyloxy, $(C_1-C_6)$-alkylcarbonylamino, $(C_3-C_8)$-cycloalkylcarbonylamino, $(C_1-C_6)$alkylmercapto, $(C_1-C_6)$-alkylsulfinyl, and $(C_1-C_6$-alkylsulfonyl.

3. A compound of the formula I or a physiologically active salt thereof according to claim 1, wherein
Q is O or S,
X is O,
Y is $CR^3$,
m is 0,
A is —$CHR^5$—, wherein $R^5$ is a substituent of the α-carbon atom of an α-amino acid, said amino acid being a natural L-amino acid or its D-isomer
B is $CO_2G$ or a carboxyl radical, where
G is a $(C_1-C_{18})$-alkyl radical, a $(C_3-C_8)$-cycloalkyl radical, a $(C_3-C_8)$-cycloalkyl-$(C_1-C_8)$-alkyl radical, a $(C_2-C_{18})$-alkenyl radical, a retinyl radical, a $(C_2-C_{18})$-alkynyl radical, a phenyl radical, a benzyl radical, a phenylethyl radical, a phenylpropyl radical or a phenylbutyl radical, wherein the above radicals defined for G contain a substituent selected from hydroxyl, $(C_1-C_4)$-alkoxy, $(C_1-C_6)$-alkylcarbonyloxy, $(C_3-C_8)$-cycloalkylcarbonyloxy, benzoyloxy, $(C_7-C_{16})$-phenylalkylcarbonyloxy and $(C_3-C_8)$-cycloalkoxycarbonyloxy, $R^1$ or $R^3$ is hydrogen and the other is a radical selected from hydrogen, fluorine, chlorine, $(C_1-C_{20})$-alkyl, $(C_2-C_{20})$-alkenyl, $(C_1-C_{10})$-alkoxy, $(C_5-C_6)$-cycloalkyl, $(C_5-C_6)$-cycloalkyl-$(C_1-C_6)$-alkyl, $(C_5-C_6)$-cycloalkyloxy, $(C_5-C_6)$-cycloalkyl-$(C_1-C_6)$-alkoxy, $(C_5-C_6)$-cycloalkyloxy-$(C_1-C_6)$-alkyl, $(C_5-C_6)$-cycloalkyloxy-$(C_1-C_6)$-alkoxy, $(C_5-C_6)$-cycloalkyl-$(C_1-C_4)$-alkyl-$(C_1-C_4)$-alkoxy, $(C_5-C_6)$-cycloalkyl-$(C_1-C_4)$-alkoxy-$(C_1-C_2)$-alkyl, $(C_5-C_6)$-cycloalkoxy-$(C_1-C_4)$-alkoxy-$(C_1-C_2)$-alkyl,—O—$[CH_2]_x$-$C_fH_{(2f+1-g)}F_g$, $(C_1-C_6)$-alkoxy-$(C_1-C_6)$-alkyl, $(C_1-C_6)$-alkoxy-$(C_1-C_6)$-alkoxy, $(C_1-C_6)$-alkoxy-$(C_1-C_4)$-alkoxy-$(C_1-C_2)$-alkyl, substituted $(C_6-C_{12})$-phenoxy, $(C_1-C_{11})$-phenylalkyloxy, $(C_6-C_{12})$-phenoxy-$(C_1-C_6)$-alkoxy, $(C_7-C_{11}$-phenylalkoxy-$(C_1-C_6)$-alkoxy, phenoxy-$(C_1-C_4)$-alkyl, $(C_7-C_{11}$-phenylalkyloxy-$(C_1-C_4)$-alkyl, phenoxy-$(C_1-C_4)$-alkoxy-$(C_1-C_2)$-alkyl and $(C_7-C_{11})$-phenylalkyloxy-$(C_1-C_4)$-alkoxy-$(C_1-C_2)$-alkyl, wherein the radicals which contain an aryl radical or moiety may be substituted on the aryl by 1, 2 or 3 identical or different substituents selected from fluorine, chlorine, cyano, trifluoromethyl, $(C_1-C_{12})$-alkyl, $(C_2-C_{12})$-alkenyl, $(C_2-C_{12})$-alkenyloxy and $(C_1-C_{12})$-alkoxy, or alternatively $R^3$ is as defined herein above and $R^1$ and $R^2$, with the pyridine carrying them, form a 5, 6, 7, 8-tetrahydroisoquinoline ring, $R^2$ is hydrogen, bromine, chlorine, cyano, $(C_1-C_{20})$-alkyl, $(C_2-C_{20})$-alkenyl, $(C_1-C_8)$-alkoxy, $(C_1-C_{18})$-alkoxymethyl, $(C_2-C_{18})$-alkenyloxymethyl, $(C_2-C_{18})$-alkynyloxymethyl, carbamoyl, N-$(C_1-C_{10})$-alkylcarbamoyl, N-$((C_1-C_{12})$-alkoxy-$(C_1-C_4)$-alkyl)carbamoyl, N,N-di-$(C_1-C_8)$-alkylcarbamoyl, N-$(C_3-C_8)$-cycloalkylcarbamoyl, N-$(C_6-C_{12})$-phenylcarbamoyl, N-$(C_7-C_{12})$-phenylalkylcarbamoyl, N-$(C_1-C_6)$-alkyl-N-$(C_6-C_{12})$-phenylcarbamoyl, N-$(C_1-C_6)$-alkyl-N-$(C_7-C_{12})$-phenylalkylcarbamoyl, N-$((C_1-C_6)$-alkoxy-$(C_1-C_6)$-alkyl)carbamoyl, carboxyl, $(C_1-C_{20})$-alkoxycarbonyl, $(C_2-C_{20})$-alkenyloxycarbonyl, retinyloxycarbonyl, $(C_3-C_8)$cycloalkoxycarbonyl, $(C_3-C_8)$-cycloalkyl-$(C_1-C_6)$-alkoxycarbonyl, $(C_3-C_8)$-cycloalkoxy-$(C_1-C_6)$-alkoxycarbonyl, phenyl-$(C_1-C_6)$-alkoxycarbonyl, phenoxy-$(C_1-C_6)$-alkoxycarbonyl or benzyloxy-$(C_1-C_6)$-alkoxycarbonyl, wherein the radicals which contain a phenyl radical or moiety may be substituted on the phenyl by 1, 2, or 3 identical or different substituents as defined herein for $R^1$ and $R^3$, $R^4$ is a $(C_1-C_{10})$-alkyl radical, $(C_1-C_4)$-alkoxy-$(C_1-C_4)$-alkyl or a radical of the formula Z, $$-[CH_2]_v-[O]_w-[CH_2]_t-E \qquad (Z),$$

where E is a pyridyl radical, a thienyl radical, a $(C_3-C_8)$-cycloalkyl radical, or a phenyl radical of the formula F

where v is 0, 1, 2 or 3, w is 0, and t is 0 or 1, and in which $R^6$, $R^7$, $R^8$, $R^9$, and $R^{10}$ are identical or different and are selected from hydrogen, fluorine, chlorine, cyano, trifluoromethyl, $(C_1-C_6)$-alkyl, $(C_1-C_6)$-alkoxy, —O—$[CH_2]_x$—$C_fH_{(2f+1-g)}F_g$, N-$(C_1-C_8)$-alkylcarbamoyl, N,N-di-$(C_1-C_6)$-alkylcarbamoyl, N-$(C_3-C_8)$-cycloalkylcarbamoyl, N-$(+)$- dehydroabietylaminocarbonyl, and (C₇–C₁₁)-phenylalkylcarbamoyl optionally substituted by fluorine, chlorine, trifluoromethyl or (C₁–C₆)-alkoxy, or alternatively wherein R⁸, R⁹, and R¹⁰ are as defined herein above and R⁶ and R⁷ together with the phenyl ring carrying them, form a naphthalene derivative, or alternatively wherein R⁶, R⁹, and R¹⁰ are as defined herein above and R⁷ and R⁸ together with the phenyl ring carrying them, form a naphthalene derivative, or alternatively R² is as defined herein above and one of R¹ and R³ is selected from a radical of the formula (D)

$$OZ \qquad (D),$$

wherein Z is as defined herein above for R⁴, and if one of R¹ and R³ is not (D), said one is as defined herein above, and further wherein v is 1, 2, 3 or 4, w is 0 and t is 0, or v is 1, 2, 3 or 4, w is 1 and t is 0, or v is 1, 2, 3 or 4, w is 1, t is 1, or alternatively R² is as defined herein above and one of R¹ and R³ is selected from a radical of the formula Z, wherein Z is as defined herein above for R⁴, and said one of R¹ and R³ which is not Z is as defined herein above, and further wherein v is 1, 2, 3 or 4, w is 0 and t is 0, or v is 1, 2, 3 or 4, w is 1 and t is 0, or v is 1, 2, 3 or 4, w is 1, t is 1, f is 1 to 4, g is 0 or 1 to (2f+1), and x is 0 or 1.

4. A compound of the formula I or a physiologically active salt thereof according to claim 1, wherein Q is O, X is O, Y is CR³, m is 0, A is a —CH₂— group which can be substituted by a methyl group, B is —CO₂G or a carboxyl radical, where G is a (C₁–C₁₈)-alkyl radical, a (C₃–C₈)-cycloalkyl radical, a (C₃–C₈)-cycloalkyl-(C₁–C₄)-alkyl radical, or a (C₂–C₁₈)-alkenyl radical, wherein the above radicals can contain a substituent selected from hydroxyl, (C₁–C₄)-alkoxy, (C₁–C₆)-alkylcarbonyloxy, (C₃–C₈)-cycloalkylcarbonyloxy, benzoyloxy, (C₇C₁₆) phenylalkylcarbonyloxy and (C₃–C₈)-cycloalkoxycarbonyloxy, or alternatively, G is a phenyl radical, benzyl radical, phenylethyl radical, phenylpropyl radical or phenylbutyl radical, one of R¹ or R³ is hydrogen and the other is a radical selected from hydrogen, (C₁–C₁₀)-alkoxy, (C₅–C₆)-cycloalkyloxy, (C₅–C₆)-cycloalkyl-(C₁–C₂)-alkoxy, —O—[CH₂]ₓ—C_fH_{(2f+1−g)}F_g, (C₁–C₄)-alkoxy-(C₁–C₄)-alkoxy, substituted (C₆–C₁₂)-phenoxy, (C₇–C₁₁)-phenylalkyloxy, (C₆–C₁₂)-phenoxy-(C₁–C₄)-alkoxy and (C₇–C₁₁)-phenylalkoxy-(C₁–C₄)-alkoxy, wherein the radicals which contain a phenyl radical or moiety may be substituted by 1, 2 or 3 identical or different substituents selected from fluorine, chlorine, cyano, trifluoromethyl, (C₁–C₁₀)-alkyl, (C₁–C₁₀)-alkoxy and (C₁–C₁₀)-alkenyloxy, R² is hydrogen, (C₁–C₈)-alkoxy, (C₁–C₁₆)-alkoxymethyl, (C₂–C₁₆)-alkenyloxymethyl, retinyloxymethyl, N-(C₁–C₁₀)-alkylcarbamoyl, N-((C₁–C₁₂)-alkoxy-(C₁–C₃)-alkyl) carbamoyl, N,N-di-(C₁–C₈)-alkylcarbamoyl, N-(C₅–C₆)-cycloalkylcarbamoyl, N-phenylcarbamoyl, N-phenyl-(C₁–C₄)-alkylcarbamoyl, carboxyl, (C₁–C₁₆)-alkoxycarbonyl, (C₂–C₁₆)-alkenyloxycarbonyl, retinyloxycarbonyl, (C₅–C₆)-cycloalkoxycarbonyl, (C₅–C₆)-cycloalkyl-(C₁–C₆)-alkoxycarbonyl or phenyl-(C₁–C₆)-alkoxycarbonyl, wherein the radicals which contain a phenyl radical or moiety may be substituted on the phenyl by 1, 2 or 3 identical or different substituents as defined for R¹ and R³, R⁴ is a (C₁–C₈)-alkyl radical or a radical of the formula Z, $$—[CH_2]_v—[O]_w—[CH_2]_t—E \qquad (Z),$$

where E is a (C₃–C₈)-cycloalkyl radical or a phenyl radical of the formula F

where v is 0, 1, 2 or 3, w is 0, and t can be 0 or 1, and in which R⁶, R⁷, R⁸, R⁹, and R¹⁰ are identical or different and are selected from hydrogen, fluorine, chlorine, cyano, trifluoromethyl, (C₁–C₆)-alkyl, (C₁–C₆)-alkoxy, —O—[CH₂]ₓ—C_fH_{(2f+1−g)}F_g, N-(C₁–C₈)-alkylcarbamoyl, N,N-di-(C₁–C₆)-alkylcarbamoyl, N-(C₃–C₆)-cycloalkylcarbamoyl, and a N-(+)-dehydroabietylaminocarbonyl-substituted benzyl radical, f is 1 to 4, g is 0 or 1 to (2f+1), and x is 0 or 1.

5. A compound of the formula I or a physiologically active salt thereof according to claim 1, wherein Q is O, X is O, Y is CR³, m is 0, A is a —CH₂-group, B is —CO₂G or a carboxyl radical, where G is a (C₁–C₁₆)-alkyl radical, a 2-cyclohexylethyl radical, a (C₁–C₄)-alkoxy-(C₁–C₂)-alkyl radical, a (C₂–C₁₀)-alkenyl radical, a phenyl radical, a benzyl radical, a phenylethyl radical, a phenylpropyl radical or a phenylbutyl radical, R¹ is hydrogen, (C₁–C₆)-alkoxy or —O—[CH₂]ₓ—C_fH_{(2f+1−g)}F_g, R² is hydrogen, N-(C₁–C₁₀)-alkylcarbamoyl, N-((C₁–C₁₂)-alkoxy-(C₁–C₃)-alkyl)carbamoyl, N,N-di-(C₁–C₈)-alkylcarbamoyl, N-(C₅–C₆)-cycloalkylcarbamoyl, N-phenylcarbamoyl, N-phenyl-(C₁–C₂)-alkylcarbamoyl, carboxyl, (C₁–C₁₆)-alkoxycarbonyl, (C₂–C₁₆)-alkenyloxycarbonyl, retinyloxycarbonyl, (C₅–C₆)-cycloalkoxycarbonyl, (C₅–C₆)-cycloalkyl-(C₁–C₆)-alkoxycarbonyl or phenyl-(C₁–C₆)-alkoxycarbonyl, wherein the radicals which contain a phenyl radical or moiety may be substituted on the phenyl by 1 or 2 identical or different substituents selected from fluorine, chlorine, cyano, trifluoromethyl, (C₁–C₁₀)-alkyl, (C₁–C₁₀)-alkoxy and (C₂–C₁₀)-alkenyloxy, R³ is hydrogen, (C₁–C₅)-alkoxy or (C₅–C₆)-cycloalkyl-(C₁–C₂)-alkoxy, wherein one of the substituents R¹ and R³ is hydrogen, R⁴ is a (C₁–C₆)-alkyl radical, a 2-phenylethyl radical, or a benzyl radical substituted by 1 or 2 radicals selected from fluorine, chlorine, cyano, trifluoromethyl, $(C_1-C_6)$-alkyl, $(C_1-C_6)$-alkoxy, —O—$[CH_2]_xC_fH_{(2f+1-g)}F_g$, N-$(C_1-C_8)$-alkylcarbamoyl, N,N-di-$(C_1-C_6)$-alkylcarbamoyl, N-$(C_3-C_6)$-cycloalkylcarbamoyl and N-(+)-dehydroabietylaminocarbonyl, f is 1 to 4, g is 0 or 1 to (2f+1), and x is 1.

6. A compound of the formula I or a physiologically active salt thereof according to claim 1, wherein Q is O, X is O, Y is $CR^3$, m is 0, A is a —$CH_2$— group, B is —$CO_2G$ or a carboxyl radical, where G is a $(C_1-C_{16})$-alkyl radical or a benzyl radical, $R^1$ is hydrogen, $R^2$ is hydrogen, N-$(C_1-C_{10})$-alkylcarbamoyl, N-$((C_1-C_{12})$-alkoxy-$(C_1-C_3)$-alkyl)carbamoyl, N-cyclohexylcarbamoyl, N-phenylcarbamoyl, N-(phenyl$(C_1-C_2)$-alkyl)carbamoyl, wherein the carbamoyl radicals which contain a phenyl moiety may be substituted on the phenyl by a fluorine, a $(C_1-C_{10})$-alkyl radical, a $C_1-C_{10}$-alkoxy radical, a carboxyl radical, a $(C_2-C_{16})$-alkoxycarbonyl radical, a $(C_2-C_{16})$-alkenyloxycarbonyl radical, a retinyloxycarbonyl radical, a $C_5-C_6$-cycloalkoxycarbonyl radical or a benzyloxycarbonyl radical, $R^3$ is hydrogen, $(C_1-C_5)$-alkoxy or 2-(cyclohexyl)-ethyloxy, wherein one of the substituents $R^2$ and $R^3$ is hydrogen, $R^4$ is a $(C_1-C_4)$-alkyl radical or a benzyl radical substituted once by fluorine, chlorine, trifluoromethyl, $(C_1-C_4)$-alkyl or $(C_1-C_3)$-alkoxy.

7. A compound of the formula I or a physiologically active salt thereof according to claim 3, wherein said $(C_2-C_{18})$-alkenyl radical defined for G is a geranyl or a farnesyl radical.

8. A compound of the formula I or a physiologically active salt thereof according to claim 1, wherein Q is S, X is O, Y is $CR^3$, m is 0, A is a $CH_2$ group, B is —$CO_2G$ or a carboxyl radical, where G is a $(C_1-C_{16})$-alkyl radical or a benzyl radical, $R^1$ is hydrogen, $R^2$ is hydrogen, N-$(C_1-C_{10})$-alkylcarbamoyl, N-$((C_1-C_{12})$-alkoxy-$(C_1-C_3)$-alkyl)carbamoyl, N-cyclohexylcarbamoyl, N-phenylcarbamoyl, N-(phenyl-$(C_1-C_2)$-alkyl)carbamoyl, wherein the carbamoyl radicals which contain a phenyl moiety may be substituted on the phenyl by fluorine, a $(C_1-C_{10})$-alkyl radical, a $(C_1-C_{10})$-alkoxy radical, a carboxyl radical, a $(C_1-C_{16})$-alkoxycarbonyl radical, a $(C_2-C_{16})$-alkenyloxycarbonyl radical, a retinyloxycarbonyl radical, a $(C_5-C_6)$-cycloalkoxycarbonyl radical or a benzyloxycarbonyl radical, $R^3$ is hydrogen, $(C_1-C_5)$-alkoxy or 2-(cyclohexyl)-ethyloxy, wherein one of the substituents $R^2$ and $R^3$ is hydrogen, $R^4$ is a $(C_1-C_4)$-alkyl radical or a benzyl radical which is substituted once by fluorine, chlorine, trifluoromethyl, $(C_1-C_4)$-alkyl or $(C_1-C_3)$-alkoxy.

9. A compound of the formula I or a physiologically active salt thereof according to claim 1, wherein Q is S, X is O, Y is $CR^3$, m is 0, A is a —$CH_2$-group, B is —$CO_2G$ or a carboxyl radical, where G is a $(C_1-C_{16})$-alkyl radical or a benzyl radical, $R^1$ is hydrogen, $R^2$ is carboxyl or $(C_1-C_{16})$-alkoxycarbonyl, $R^3$ is hydrogen, and $R^4$ is a $(C_1-C_4)$-alkyl radical.

10. A pharmaceutical composition comprising:

a compound of the formula I or a physiologically active salt thereof according to claim 1 and a pharmaceutically acceptable excipient, wherein the proviso set forth in claim 1 does not apply.

11. A method for inhibiting collagen biosynthesis comprising the step of administering to a patient in recognized need thereof an effective amount of a compound of the formula I or a physiologically active salt thereof according to claim 1, wherein the proviso set forth in claim 1 does not apply.

12. A method for fibrosuppression comprising the step of administering to a patient in recognized need thereof an effective amount of a compound of the formula I or a physiologically active salt thereof according to claim 1, wherein the proviso set forth in claim 1 does not apply.

13. A method for treating fibrotic diseases comprising the step of administering to a patient in recognized need thereof an effective amount of a compound of the formula I or a physiologically active salt thereof according to claim 1, wherein the proviso set forth in claim 1 does not apply.

14. A method for treating fibrotic diseases according to claim 13 wherein said fibrotic diseases are diseases of the liver, the lung, or the skin.

15. A compound of the formula (I) as claimed in claim 1, in which

Q is O,

X is O,

Y is $CR^3$, where $R^3$ is hydrogen, m is 0,

A is a —$CH_2$— group,

B is —$CO_2G$, where

G is a $(C_1-C_{16})$-alkyl radical or a benzyl radical, $R^1$ and $R^2$, together with the pyridine carrying them, form an isoquinoline ring with an unsubstituted benzo moiety, and $R^4$ is methyl.

16. A compound of the formula (I) as claimed in claim 1, in which

Q is O,

X is O,

Y is $CR^3$, m is 0,

A is a —$CH_2$— group,

B is —$CO_2G$, where

G is a $(C_1-C_{16})$-alkyl radical or a benzyl radical, $R^1$ is hydrogen, and $R^2$ and $R^3$, together with the pyridine carrying them, form a quinoline ring with an unsubstituted benzo moiety, and $R^4$ is methyl.

* * * * *

UNITED STATES PATENT AND TRADEMARK OFFICE
CERTIFICATE OF CORRECTION

PATENT NO. : 5,658,933
DATED : August 19, 1997
INVENTOR(S) : Weidmann et al.

It is certified that error appears in the above-identified patent and that said Letters Patent is hereby corrected as shown below:

Title page, Item [57], Abstract, line 2; and Claim 1, column 68, lines 26-35, Formula I,

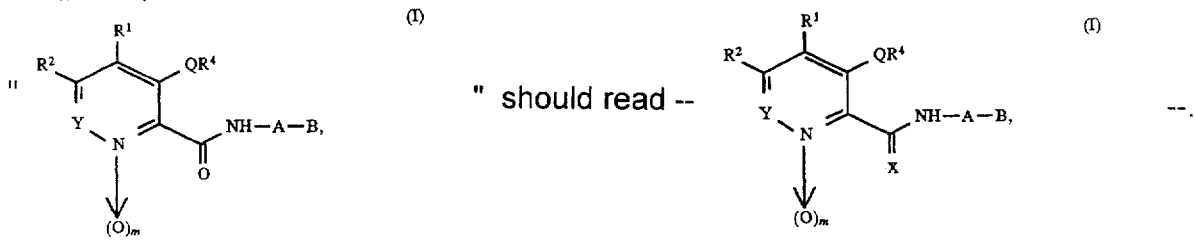

Claim 1, column 68, line 45, "—CH R$^5$—" should read ——CHR$^5$——.
    column 69, line 5, "C$_f$H$_{(2f+1-g)}$(F$_g$" should read --C$_f$H$_{(2f+1-g)}$F$_g$--;
        line 25, "arylcarbamoyl" should read -- -arylcarbamoyl--;
        line 28, and line 29, "carbamoyl" should read -- -carbamoyl--;
        line 33, "alkyl)" should read -- -alkyl)--;
        line 44, and line 47, "carbamoyloxy" should read
        -- -carbamoyloxy--;
        line 65 "N,N-di" should read --N,N-di- --;
        line 66, "(C$_3$–C$_8$)" should read --(C$_3$–C$_8$)- --;
    column 70, line 8, "N-(C$_6$–C$_{12}$)-alkylsulfamoyl" should read
        --N-(C$_6$–C$_{12}$)-arylsulfamoyl--;
        line 22, "(C$_1$ C$_{12}$)alkoxy" should read --(C$_1$–C$_{12}$)alkoxy--;
        line 42 "N,N-di(C$_1$–C$_{12}$)" should read --N,N-di(C$_1$–C$_{12}$)- --;
        lines 48, 49, 50, and 52, "carbamoyl" should read
        -- -carbamoyl--;
        line 66, "carbamoyloxy" should read -- -carbamoyloxy--;

UNITED STATES PATENT AND TRADEMARK OFFICE
CERTIFICATE OF CORRECTION

PATENT NO. : 5,658,933
DATED : August 19, 1997
INVENTOR(S) : Weidmann et al.

It is certified that error appears in the above-identified patent and that said Letters Patent is hereby corrected as shown below:

Claim 1, column 71, line 2, "carbamoyloxy" should read -- -carbamoyloxy--;
line 11, "alkylcarbonylamino" should read --aralkycarbonylamino--;
line 20, "N,N-di" should read --N,N-di- --;
line 36, "$(C_3-C_8)$" should read --$(C_3-C_8)$- --;
line 49, "$(C_6-C_{12})$-alkoxy" should read --$(C_1-C_6)$-alkoxy--;
line 54, "$(C_1\ C_{12}$-" should read --$(C_1-C_{12})$- --;
line 56, "$C_1-C_6)$-" should read --$(C_1-C_6)$- --;

Claim 1, column 72, lines 23-29, Formula (1b)

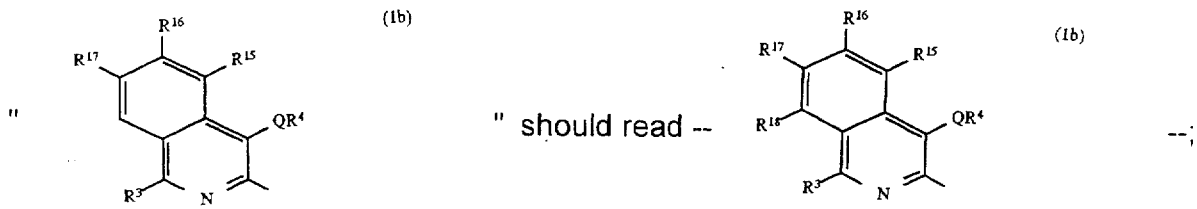

line 34, "$(C-C_3)$" should read --$(C_1-C_3)$- --;
line 40, "$C_1-C_{10})$-alkylmercapto" should read --$(C_1-C_{10})$-alkylmercapto--;
line 65, "$(C_7-C_{12}$-aralkylcarbamoyl" should read --$(C_7-C_{12})$-aralkylcarbamoyl--;

UNITED STATES PATENT AND TRADEMARK OFFICE
CERTIFICATE OF CORRECTION

PATENT NO. : 5,658,933  
DATED : August 19, 1997  
INVENTOR(S) : Weidmann et al.

Page 3 of 4

It is certified that error appears in the above-identified patent and that said Letters Patent is hereby corrected as shown below:

Claim 1, column 73, line 3, "carbamoyl" should read -- -carbamoyl--;
  line 42, "—O—[CH$_2$]$_x$" should read ----O—[CH$_2$]$_x$--;
  line 46, "(C$_1$–C$_8$-" should read --(C$_1$–C$_8$)- --;
 column 74, line 3, "C$_7$–C$_{11}$)-aralkyl" should read --(C$_7$–C$_{11}$)-aralkyl--; and
  line 7, "C$_6$–C$_{12}$)-arylcarbonyl" should read
  --(C$_6$–C$_{12}$)-arylcarbonyl--.
Claim 2, column 75, line 4, "(C$_3$–C$_8$)-aralkylcarbonyloxy" should read
  --(C$_7$–C$_{16}$)-aralkylcarbonyloxy--;
  line 16, "(C$_6$–C$_{12}$-arylamino" should read
  --(C$_6$–C$_{12}$)-arylamino--.
  line 28, "(C$_1$–C$_6$-alkyl" should read --(C$_1$–C$_6$)-alkyl--, and
  "(C$_1$–C$_8$-alkoxy" should read --(C$_1$–C$_8$)-alkoxy--;
  line 42, "N-(C$_3$–C$_8$-" should read --N-(C$_3$–C$_8$)- --; and
  line 46, "(C$_1$–C$_6$-alkylsulfonyl" should read
  --(C$_1$–C$_6$)-alkylsulfonyl--.
Claim 3, column 76, line 13, "(C$_1$–C$_{11}$)" should read --(C$_7$–C$_{11}$)--.
  lines 14 and 15, after "C$_{11}$", insert --)--;
  line 37, "carbamoyl" should read -- -carbamoyl--;and
  line 67, "(C$_3$–C$_8$)" should read --(C$_3$–C$_6$)--.

UNITED STATES PATENT AND TRADEMARK OFFICE
CERTIFICATE OF CORRECTION

PATENT NO. : 5,658,933
DATED : August 19, 1997
INVENTOR(S) : Weidmann et al.

It is certified that error appears in the above-identified patent and that said Letters Patent is hereby corrected as shown below:

Claim 4, column 77, line 66, "carbamoyl" should read -- -carbamoyl--.
Claim 5, column 79, line 2, "N-($C_1$-$C_8$-" should read --N-($C_1$-$C_8$)- --.
Claim 6, column 79, line 24, "$C_1$-$C_{10}$-alkoxy" should read --($C_1$-$C_{10}$)-alkoxy--; and line 27, before "$C_5$", insert --(--.

Signed and Sealed this

Thirtieth Day of May, 2000

Attest:

Q. TODD DICKINSON

*Attesting Officer*          *Director of Patents and Trademarks*